(12) United States Patent
Shaw

(10) Patent No.: US 12,642,486 B2
(45) Date of Patent: Jun. 2, 2026

(54) AURICULAR ELECTROENCEPHALOGRAM (EEG) AND AUTOMATIC REMEDY SYSTEMS FOR NEUROPSYCHIATRIC DISORDERS

(71) Applicant: David C. Shaw, Torrance, CA (US)

(72) Inventor: David C. Shaw, Torrance, CA (US)

( * ) Notice: Subject to any disclaimer, the term of this patent is extended or adjusted under 35 U.S.C. 154(b) by 0 days.

(21) Appl. No.: 19/191,555

(22) Filed: Apr. 28, 2025

(65) Prior Publication Data

US 2026/0083395 A1      Mar. 26, 2026

Related U.S. Application Data

(60) Provisional application No. 63/833,151, filed on Oct. 26, 2024, provisional application No. 63/732,962,
(Continued)

(51) Int. Cl.
| | |
|---|---|
| *A61N 1/04* | (2006.01) |
| *A61B 5/00* | (2006.01) |
| *A61B 5/291* | (2021.01) |
| *A61B 5/372* | (2021.01) |
| *A61N 1/36* | (2006.01) |

(52) U.S. Cl.
CPC ............ *A61B 5/4836* (2013.01); *A61B 5/291* (2021.01); *A61B 5/372* (2021.01); *A61B 5/4094* (2013.01); *A61B 5/6803* (2013.01); *A61B 5/7282* (2013.01); *A61B 5/7405* (2013.01); *A61B 5/7455* (2013.01); *A61B 5/746* (2013.01);
(Continued)

(58) Field of Classification Search
CPC ....... A61B 5/4836; A61B 5/291; A61B 5/372; A61B 5/4094; A61B 5/6803; A61B 5/7282; A61B 5/7405; A61B 5/7455; A61B 5/746; A61B 5/7475; A61B 2560/0468; A61B 2562/164; A61N 1/0456; A61N 1/36025; A61N 1/36053; A61N 1/36075; A61N 1/36132; A61N 1/36135; A61N 1/36031

See application file for complete search history.

(56) References Cited

U.S. PATENT DOCUMENTS

| | | | |
|---|---|---|---|
| 6,230,049 B1 * | 5/2001 | Fischell | A61B 5/372 |
| | | | 600/544 |
| 10,688,274 B1 | 6/2020 | Jovanov | |

(Continued)

*Primary Examiner* — Carl H Layno
*Assistant Examiner* — Anh-Khoa N Dinh
(74) *Attorney, Agent, or Firm* — PATENTFILE, LLC; Bradley C. Fach; Steven R. Kick

(57) ABSTRACT

An auricular electroencephalogram (EEG) monitoring system may include an EEG recording module having a plurality of EEG sensor electrodes, configured to be coupled to a wearer's ear, and a processing unit configured to analyze EEG data recorded by the EEG recording module to detect presence or cessation of neuropsychiatric disorders of the wearer. An automatic detection-remedy system may include an auricular electroencephalogram (EEG) monitoring system and a transcutaneous auricular vagus nerve stimulation (taVNS) unit having a stimulating electrode in contact with vagus innervated auricular skin of the wearer's ear. When the presence of EEG signals suggestive of the neuropsychiatric disorder is detected by the processing unit, the processing unit is configured to immediately send signals to the taVNS unit to automatically start sending pre-determined electric stimuli to the vagus innervated auricular skin of the wearer's ear.

29 Claims, 23 Drawing Sheets

Related U.S. Application Data filed on Oct. 12, 2024, provisional application No. 63/732,819, filed on Sep. 25, 2024.

(52) U.S. Cl.
CPC .......... *A61B 5/7475* (2013.01); *A61N 1/0456* (2013.01); *A61N 1/36025* (2013.01); *A61N 1/36031* (2017.08); *A61B 2560/0468* (2013.01); *A61B 2562/164* (2013.01)

(56) References Cited

U.S. PATENT DOCUMENTS

| | | | |
|---|---|---|---|
| 11,253,674 B2 | 2/2022 | Le Van Quyen et al. | |
| 11,623,079 B2 | 4/2023 | Simon et al. | |
| 11,931,175 B2 | 3/2024 | Pintat et al. | |
| 2003/0195588 A1* | 10/2003 | Fischell | A61N 2/02 |
| | | | 607/55 |
| 2004/0138536 A1* | 7/2004 | Frei | A61N 1/36082 |
| | | | 600/300 |
| 2009/0264956 A1* | 10/2009 | Rise | A61B 5/165 |
| | | | 607/45 |
| 2014/0081348 A1* | 3/2014 | Fischell | A61N 1/36071 |
| | | | 607/45 |
| 2014/0206945 A1 | 7/2014 | Liao | |
| 2018/0021564 A1* | 1/2018 | Goodall | A61N 2/002 |
| | | | 600/379 |
| 2019/0333480 A1 | 10/2019 | Lang | |
| 2020/0390997 A1* | 12/2020 | Jovanov | A61B 5/16 |
| 2024/0008800 A1 | 1/2024 | Ahmed et al. | |
| 2024/0189594 A1 | 6/2024 | Hamner | |
| 2024/0198086 A1 | 6/2024 | Simon et al. | |

* cited by examiner

AURICULAR ELECTROENCEPHALOGRAM (EEG) AND AUTOMATIC REMEDY SYSTEMS FOR NEUROPSYCHIATRIC DISORDERS

CROSS REFERENCE TO RELATED APPLICATIONS

This application claims priority to and the benefit of the filing date of U.S. Provisional Application No. 63/732,819 filed on Sep. 25, 2024, entitled "Automatic auricular anti-seizure device", which is hereby incorporated by reference in its entirety. This application also claims priority to and the benefit of the filing date of U.S. Provisional Application No. 63/732,962, filed on Oct. 12, 2024, entitled "Automatic auricular detection-remedy system", which is hereby incorporated by reference in its entirety. This application further claims priority to and the benefit of the filing date of U.S. Provisional Application No. 63/833,151, filed on Oct. 26, 2024, entitled "Automatic auricular detection-remedy system for neuropsychiatric disorders", which is hereby incorporated by reference in its entirety.

FIELD OF THE INVENTION

This patent specification relates to the field of neuropsychiatric disorders, electroencephalogram (EEG) and automatic EEG analysis and the field of transcutaneous auricular vagus nerve stimulation (taVNS or tVNS). More specifically, the present invention relates to the field of wearable electroencephalogram systems and transcutaneous auricular vagus nerve stimulation which may be used for the treatment of neuropsychiatric disorders.

BACKGROUND

There are various types of wearable health tracking devices available, including various smart watches and health tracker devices. Several health conditions can be monitored or recorded by these devices, including blood oxygen, heart rate, breathing rate, sleep, exercise, steps count, electrocardiogram (ECG) and blood pressure etc. (Apple watch series 4-10 or Samsung Galaxy Watch 4-7 can record ECG). However, none of the smart watches or health tracking devices can do electroencephalogram (EEG) or monitor the brain activities. Besides sending notification or warning to the person wearing them, these devices cannot take any therapeutic actions. If therapeutic actions can be initiated automatically, it would be very beneficial to the person wearing these devices.

The human external ear is a commonly disregarded location for health monitoring. The ear is very close to the brain and recent studies have shown that electrodes placed in the external ear canal can do electroencephalogram (EEG). Traditional EEG is done with multiple (mostly 21) electrodes and wires being attached to the scalp. It is very cumbersome and hard for wearer to move around. In traditional EEG, the electrodes are attached or glued to the scalp. Traditional EEG is usually for short-term use only (half an hour to a couple days) because the electrodes often become detached after a short time. Thus, there exists a great need to have a miniature nice-looking device which can record EEG on a long-term (weeks or months or years) basis. Traditionally, EEG has been used primarily in the medical field or biomedical research field. Nowadays, in the artificial intelligence and robotics era, EEG or modified EEG is also heavily used in the brain-computer interface (BCI).

Advancement in electronics technology, miniaturization trend, and dry electrode technology, together with sophisticated EEG interpretation algorithms, have enormously widened the potential usefulness of EEG in various medical fields.

The external ear is the only location where the vagus nerve reaches the body surface (the skin), through auricular branch of vagus nerve. The vagus nerve innervated auricular skin includes tragus, cymba-concha, cavum-concha, the external ear canal and small adjacent regions of the external ear. Thus, transcutaneous auricular vagus nerve stimulation (taVNS) can be placed on the vagus innervated auricular skin to stimulate the vagus nerve. The vagus nerve has huge influence on various human body functions, including brain, heart, breathing, emotions, blood pressure, GI system and metabolism etc.

In recent years, wireless in-ear EEG had been reported. For example, as published on Aug. 2, 2024, in Nature Communications, Ryan Kaveh et al reported using wireless miniature dry ear electrodes for in-ear EEG, with wireless electronics and offline classification algorithms, to monitor drowsiness of pilots and drivers. They described the design of earpieces for EEG, the neural recording hardware, the electrode materials and multi-sensor array. The recorded EEG data are digitized and transmitted to a processing unit for offline processing. They also describe manufacturing methods for in-ear EEG sensors. Two contralaterally worn earpieces can provide up to 11 channels with a common reference. Either right or left cymba concha electrode can be used as a reference. Prior to this report, earpieces with wet (hydrogel coated) electrodes were often used for EEG. These in-ear EEGs have been shown to successfully monitor drowsiness, seizure and sleep etc.

The currently available smart watches and health trackers can track sleep and provide duration of various sleep stages. For example, Apple watch Series 9 can monitor sleep and divide into 4 sleep stages: Awake, Rapid eye movement (REM) sleep, Core sleep and Deep sleep. These sleep stages were "guessed" by monitoring the person's heart rate, breathing, movement, blood oxygen etc. The most accurate sleep monitoring may be through electroencephalogram (EEG). Since these devices cannot do EEG, their sleep monitoring is not very accurate.

Various EEG algorithms for decoding and processing of EEG data have been developed and described in many studies. With these EEG analysis algorithms and long-term EEG monitoring, they were able to accurately detect seizure (seizure also called epilepsy), migraine, cluster headache, depression, bipolar disease and other neurological or psychiatric conditions. They also found changes of EEG patterns suggestive of impending seizure, migraine, cluster headache, depression, bipolar disease and other neurological or psychiatric conditions. Artificial intelligence, including machine learning (ML) and deep learning (DL) algorithms were applied to EEG data for processing. Several different methods with very high accuracy for seizure detection were described by Maham Saeidi, et al, in a published article in Brain Science on Nov. 18, 2021.

Besides seizure, many neuro-psychiatric disorders or conditions can be detected with EEG, including migraine, cluster headache, major depressive disorder, bipolar disease, autism, schizophrenia, tinnitus, dyslexia, stroke, etc. In 2023 Hao Zhang et al published a review article regarding principles of EEG analysis methods in neuroscience and clinical neurology. As reported by Maham Saeidi et al and Hao Zhang et al, these researches in EEG data analysis have leaded to detection of stroke, autism, dyslexia and tasks including emotion recognition, mental workload, motor imagery, neurodegenerative diseases, sleep stages scoring and seizure detection, etc.

Migraine headache affects millions of people in the USA. There are many medicines which can help migraine. The triptans are one of the mainstream medicines being used for migraine. Triptans can be taken orally, or intranasally or by subcutaneous injection. There are also several prophylactic medicines available. Even with all of these, migraine headaches still produce major impact on the patients' lives and huge economic loss. Migraine can occur suddenly. A reliable method for pre-migraine management is in great need. Previously, migraine attacks were considered unpredictable making preemptive interventions not feasible. However, it was found that there are neurophysiological changes 24-48 hours before migraine attacks. These neurophysiological changes can be detected using long-term EEG monitoring. In 2020, Isabel Martin et al reported using EEG to predict future migraine attacks. They found that 24 hours before migraine onset, there was a statistically significant modulation of the EEG, with decrease of relative power in the delta waves and increase of beta wave frequency bands, at rest. There was also a notable reduction of the amplitude and coherence measures of an attention event-related brain potential (P300). There were other studies regarding migraine and cluster headache with EEG changes. In 2016 Cao Z. et al reported that resting-state EEG power and coherence vary between migraine phases. In 2023, Ning Zhang et al reported a review of using modern EEG data processing and analysis for EEG-based migraine analysis. It would be very valuable if patients can be notified of impending migraine or cluster headache and can start taking prophylactic measures preemptively.

In 2024, Thomas Van den Hoek reported another review article regarding EEG and migraine. Traditional EEG did not help much in the management or prediction of migraine headache. One of the most important reasons is due to the fact that traditional EEG was mostly done only short-term on cross-sectional basis. Recently, it was found that a more long-term longitudinal EEG can make subtle changes in EEG much more detectable. Advancement in data processing and analysis also help to find EEG changes during migraine. Furthermore, it was also found that EEG changes can be detected even before onset of acute migraine attack. Longitudinal studies have been able to identify some pre-ictal changes in spontaneous EEG features compared to the inter-ictal phase, and also between migraine patients and controls. These differences include EEG slowing, alpha and theta band asymmetry, enhanced EEG spectral power, and coherence. The observation that EEG power and coherence were reduced during the acute migraine as compared to the before migraine period could be used to predict migraine before an attack. Raghuraman L. and Joshi S. reported in 2024 one more review article regarding EEG and migraine. They reported EEG changes in migraine, including cortical hyperexcitability and habituation deficit to sensory stimuli and alpha oscillations. Spectral analysis of EEG waves often showed more reliable and consistent results than features read off the EEG directly. EEG microstate was found to be the most promising method showing characteristic identifiable features for diagnosis of migraine.

Cluster headache is another type of headache which affects millions of people in USA. It is also called trigeminal autonomic cephalgia. Cluster headache is usually shorter (15-180 minutes) than migraine, but is much more intense and can occur more often (up to 8 times a day). The pain with cluster headache is so severe that patients are often incapacitated during the attack. It can keep recurring for weeks or even months. In 2022, Padmarathy N. et al reported using EEG to identify cluster headache and migraine.

Transcutaneous vagus nerve stimulation has been found to help in management of migraine headaches and cluster headaches. In 2021, Straube A. and Eren O. reported that transcutaneous auricular vagus nerve stimulation (taVNS) helps in treatment of acute migraine headache and cluster headache. The taVNS also helps in prevention or prophylaxis of migraine and cluster headaches. In 2022, Ana de Carvalho published a review article regarding the effect of transcutaneous auricular vagus nerve stimulation (taVNS) and transcutaneous cervical vagus nerve stimulation (tcVNS) for migraine headache. The VNS stimulation settings or parameters (waveform, frequency, intensity, cycle, and current) were discussed. In 2016 Silberstein S D et al reported success in using non-invasive (transcutaneous) vagus nerve stimulation for treatment of cluster headaches. Similarly, in 2017, Peter Goadsby et al reported using non-invasive vagus nerve stimulation for cluster headaches.

The advancement in EEG technology and EEG analysis with machine learning have also helped EEG in detection of major depressive disorder. As reported by C. Wu et al in 2021, four common EEG features were studied, including: band power (BP), coherence, Higuchi's fractal dimension, and Katz's fractal dimension. They found that coherence-based connectivity is a reliable feature to detect major depressive disorder with high accuracy. Sara Yasin et al reported in 2021, using EEG for detection of major depressive disorder and bipolar disorder. They reviewed recent researches using artificial neural networks (shallow and deep learning-based) approaches and was able to successfully detect major depressive disorder and bipolar disorder using EEG.

Vagus nerve stimulation (VNS) has been approved by US Food and Drug Administration (FDA) for treatment of drug-resistant depression. In 2018, C. Wu et al reported that transcutaneous auricular vagus nerve stimulation (taVNS) was effective for treatment of major depressive disorder. In 2020, Yonathan Yap reported that taVNS can provide therapeutic effect similar to that of VNS. The taVNS treatment is effective for bipolar disorder, schizophrenia, major depressive disorder etc. In this review article, they also discussed the stimulation parameters, stimulation sites, and available devices.

In 2023 Ashraf Gerges reported an article reviewing the application of taVNS to various types of neuropsychiatric diseases. They also reported the various electric stimulation parameters. The stimulation parameters include pulse frequency, pulse width, pulse-pause ratio (on/off timing), electrode type, device used, electric current type, electrode location etc. These data were reported in their figures and tables. For example, in 68% of the studies, the taVNS stimuli intensity was set at a level above the individual's sensory threshold and below the pain threshold. The Intensity values ranged from 0.5 to 50 mA. The electrode size ranged from 2-200 mm. Pulse frequency of either 20 Hz or 25 Hz was used in 74% of the studies. The most common pulse width ranged from 0.05 to 1.0 ms, with either 0.20, or 0.25 ms, being the most commonly used. In their review, 62% of the studies stimulated only the left auricular branch of vagus nerve, while bilateral vagus nerve stimulation was done in 27% of the studies.

For migraine, Ashraf Gerges et al reported using maximally tolerable stimulus ranging from 0.1 to 5 mA, delivered to concha. Pulse width ranged from 0.05 to 0.25 ms, and pulse frequency ranged from 1 to 25 Hz. The treatment sessions ranged from 30 to 240 minutes, delivered daily or only 3 times per week, and the total treatment duration ranged from 4 to 12 weeks.

For depression, Ashraf Gerges reported significantly favorable result with bilateral or unilateral vagus nerve stimulation with intensity at non-painful level (above sensory threshold). The other parameters include: intensity ranging from 0.5-6 mA, pulse frequency ranging from 20-25 Hz and pulse width ranging from 0.2-1 ms. Treatment timing ranged from 60-240 min/day, delivered 5-7 days/week for 4-12 weeks. They also disclosed the stimulation parameters for other neuro-psychiatric conditions.

In 2021, Y. Ech-Choudany et al described a method for seizure detection from EEG using dissimilarity-based time-frequency distribution for seizure detection. They reported 98% accuracy. In 2020, M. Savadkoohi et al described another method with machine learning approach for seizure detection from EEG. They reported 100% accuracy. In 2024, Ayda Gokturk and Jacklyn Luu described utilizing machine learning on EEG data for seizure detection. They compared 5 machine learning models—Logistic Regression, K Nearest Neighbors (kNN), Random Forest, Neural Network, and Support Vector Machine (SVM). They found that the SVM model outperforms the other 4 models, achieving an accuracy of 96.77%, precision of 94.27%, and recall of 88.87%. In 2002, Joyce Wu et al described using interictal epileptiform discharges (sharp waves and spikes) to successfully predict impending seizures in tuberous sclerosis patients.

The mainstream treatment for epilepsy is with anti-epileptic medications. However, there are substantial percentage (some estimate: up to 30%) of epilepsy patients who do not respond adequately to medications (They are called refractory or drug-resistant epilepsy patients). Some of these refractory epilepsy patients require surgery; others might consider adjunct seizure therapies. The adjunct seizure therapy options include vagus nerve stimulation, sounds or music therapy, electromagnetic modulation and others. The anti-epileptic medications can be given on a fixed schedule. Additional medications or extra dose of medications can also be given on an as needed basis when patients have epilepsy or break-through epilepsy. Self-administration of as needed medications to be given orally immediately at onset of acute seizures is often impractical because the patients might not be able to recognize having seizure, or seizure occurring during sleep, or unable to swallow medicines, or unable to reach medicines. As needed medications can be given by injections in ambulances, emergency rooms, hospitals or clinics. However, there would be substantial delay before the seizure is recognized and before ambulance arrives. During acute seizures, treatment should be started as soon as possible because prolonged seizures could be very detrimental to human health and could be even life-threatening. Thus, there exists a great need to have seizures detected immediately and automatic treatment or therapy started instantly at onset of seizures. It is also very important if prophylactic therapy can be started during period of impending epilepsy.

The US Food and Drug Administration (FDA) approved vagus nerve stimulation only for left vagus nerve when stimulated at neck region, due to concern of possible bradycardia when right vagus nerve is stimulated. The practice of using transcutaneous auricular vagus nerve stimulation to treat seizures was reviewed by Yu Wang et al in 2020. They reviewed other studies and found that bilateral auricular vagus nerve stimulation is safe with no increase of side effects as compared with right-sided stimulation. They also stated that bilateral stimulation is more effective. From review of many studies, they found that the stimulation parameters for seizures have a large range of variation. The most common stimulation frequency is 20 Hz or 25 Hz (range 0.5-120 Hz). The common stimulation pulse width is 1 ms or 0.25 ms (range 0.02-1 ms). They did find that pulse width of 500 microsecond is the most biological active. They reported that the stimulation intensity is often adjusted by the patients according to their tolerance.

It has been observed that during seizure the heart rate often increases above the baseline-a phenomenon called ictal tachycardia. It was reported that about 64% of generalized seizures and about 71% of partial onset seizures were associated with significant heart rate changes. Since high percentage of people with epilepsy experience increased heart rate during seizures, a tachycardia-based seizure detection algorithm was developed. A company, LivaNova (one of the leading VNS manufacturers) developed a VNS therapy system called "AutoStim" that can automatically stimulate the vagus nerve when tachycardia is detected. However, this approach of using heart rate as surrogate marker for seizures has significant disadvantage. The outcome depends on how the threshold is elected. In one report, the ictal tachycardia was arbitrarily defined as a heart rate of >100 beats per minute (BPM) during a seizure, with at least a 55% increase or 35 bpm increase from baseline heart rate. In another report, a threshold of 20% increase of heart rate is associated with the highest sensitivity-capturing about 80% of seizures. However, the 20% threshold will have high false positive rate of about 7 non-seizure-related stimuli per hour. When AutoStim threshold increases, the sensitivity decreases and false positives also decreases. Heart rate increase due to exercise or other activities often cannot be reliably differentiated from ictal tachycardia. Due to all these limitations, it is clear that using heart rate monitoring to "guess" presence of seizure would inevitably has a lot of false positive (unnecessary stimuli being given) and false negative (patients with seizures not identified). The practice of using vagus nerve stimulation for epilepsy treatment were reviewed by Herman Gonzales et al in 2019 and by Breanne Fisher et al in 2021. Herman Gonzales et al also reviewed the AutoStim system sold by LivaNova company.

Vagus nerve stimulation (VNS) therapy has been approved by US Food and Drug Administration (FDA) as an adjunct treatment for drug-resistant epilepsy. The placement of a traditional VNS device requires a surgery. The VNS device is usually placed under the skin in the chest with a wire going to the neck to wrap around or attach to the left vagus nerve in the neck. The VNS can give electrical stimuli to the vagus nerve. Various settings of stimulating patterns, strength, duration, frequency and intervals have been studied. For example, a setting with stimuli given in cycles of 30 seconds on and 5 minutes off is commonly used. The stimulation could be given 3-4 times per day and each time 1-4 hours. The stimulation strength varies from low (around 0.25 mA) to high (around 1.75 mA). In some studies, patients were allowed to adjust the stimulation strength to maximum tolerable strength. The VNS has been shown to help prevent impending seizures before they start and help to stop or shorten them if they do. It also helps to decrease symptoms in the post-ictal phase. The VNS decreases seizures by sending regular mild pulse of electrical stimuli to the vagus nerve. If a person is aware of a seizure happening, the person can swipe a magnet on the VNS to send extra burst of electric stimuli and this often helps to stop the seizure or decrease the severity of seizure. Similarly, various settings of stimulating patterns, strength, duration, frequency and intervals of the extra burst of electric stimuli have been studied to find the most effective stimulating setting. However, there is a problem that the person might not be aware of occurrence of a breakthrough seizure, or might be unable to respond to it or too late to respond to it, or seizure occurring during sleep.

Similar to VNS, many studies had shown effectiveness of using transcutaneous auricular vagus nerve stimulation (taVNS) for seizures. In 2000, Ventureya proposed using taVNS for seizures therapy. Since then, more studies have shown that taVNS can help to decrease seizure frequency, duration and severity, similar to that with VNS. In 2021 Breanne Fisher et al published another review article showing effectiveness of using vagus nerve stimulation to treat drug-resistant epilepsy. The practice of using transcutaneous auricular vagus nerve stimulation for seizures was also reviewed by Marios Lampros et al in 2021. They reported mean seizure frequency reduction varied from 30-65% with only mild adverse effects.

Therefore, a need exists for novel health tracking devices that can perform long-term electroencephalogram (EEG) monitoring of the brain activities for detection of neuropsychiatric disorders. A need also exists for a novel wearable convenient device that can provide therapeutic actions automatically and instantly in response to the EEG detection of neuropsychiatric disorders.

BRIEF SUMMARY OF THE INVENTION

According to one aspect consistent with the principles of the invention, an auricular electroencephalogram (EEG) monitoring system is provided. In some embodiments, an auricular electroencephalogram (EEG) monitoring system may include an auricular EEG recording module configured to be coupled to a wearer's first ear or the peri-auricular area around the first ear, and the EEG recording module may include a plurality of (at least two, but preferably more than two) EEG sensor electrodes. These EEG sensor electrodes are configured to contact separate areas of the wearer's first ear or the peri-auricular area around the wearer's first ear. The areas of the ear or the peri-auricular area that the EEG sensor electrodes are configured to contact may be selected from at least one of the following: an external portion of the wearer's first ear, an external ear canal of the wearer's first ear, and peri-auricular area around the wearer's first ear. The peri-auricular area refers to a portion of the head around the auricle (pinna) and this portion of the head is typically hairless. The peri-auricular area includes a portion of the head in front of the auricle (pre-auricular area) and a portion of the head above and behind the auricle (post-auricular area). The pre-auricular area is small, about one inch wide and about two inches long and curved along the anterior edge of the auricle. The post-auricular area is also small, approximately one inch wide and about three inches long and curved along the superior and posterior edges of the auricle (pinna). The post-auricular area is where a behind-the-ear hearing aid is usually located. These small pre-auricular area and post-auricular area together will be called "peri-auricle area" hereinafter. (Anterior, posterior, superior, in front of and behind etc. all refer to the directions relative to the wearer's head when the wearer is in an upright position.) The auricular EEG recording module may be configured to record EEG data of the wearer. The auricular electroencephalogram (EEG) monitoring system may include a network interface which may be configured to generate a notification to a client device. A processing unit may be in electronic communication with the auricular EEG recording module and the network interface, and the processing unit may be configured to analyze the EEG data recorded by the auricular EEG recording module to detect presence or cessation of EEG signals suggestive of one or more neuropsychiatric disorders. When the presence of EEG signals suggestive of the one or more neuropsychiatric disorders is detected, the processing unit may be further configured to immediately send signals to the network interface to generate a notification to the client device.

According to another aspect consistent with the principles of the invention, an automatic detection-remedy system is disclosed. In some embodiments, an automatic detection-remedy system may include an auricular electroencephalogram (EEG) monitoring system, having an auricular EEG recording module configured to be coupled to a wearer's first ear or the peri-auricular area around the wearer's first ear, and the EEG recording module may include a plurality of (at least two, but preferably more than two) EEG sensor electrodes. These EEG sensor electrodes are configured to contact separate areas of the wearer's first ear or peri-auricular area around the wearer's first ear. The areas that the EEG sensor electrodes are configured to contact may be selected from at least one of the following: an external portion of the wearer's first ear, an external ear canal of the wearer's first ear, and a peri-auricular area around the wearer's first ear, and the auricular EEG recording module may be configured to record EEG data of the wearer. The automatic detection-remedy system may further include a transcutaneous auricular vagus nerve stimulation unit (first taVNS unit) having a first stimulating electrode configured to contact vagus innervated auricular skin of the wearer's first ear. The vagus innervated auricular skin includes external ear canal, tragus, cymba-concha, cavum-concha and small adjacent areas. The vagus innervated auricular skin that the stimulating electrode is configured to contact may be selected from at least one of the following: tragus, cymba-concha, cavum-concha and the external ear canal of the wearer's first ear. A processing unit may be in electronic communication with the auricular EEG recording module and in electronic communication with the taVNS unit, and the processing unit may be configured to analyze EEG data recorded by the EEG monitoring system to detect the presence or cessation of EEG signals suggestive of one or more neuropsychiatric disorders. When the presence of EEG signals suggestive of a neuropsychiatric disorder is detected by the processing unit, the processing unit may be configured to immediately send signals to the first taVNS unit to automatically start sending pre-determined electric stimuli to the vagus innervated auricular skin of the wearer's first ear to which the first stimulating electrode is in contact with. When cessation of EEG signals suggestive of the neuropsychiatric disorder is detected by the processing unit, the processing unit may be further configured to immediately send signals to the first taVNS unit to automatically stop sending pre-determined electric stimuli to the vagus innervated auricular skin of the wearer's first ear to which the first stimulating electrode is in contact with. The processing unit may be further configured to analyze the EEG date recorded by the EEG monitoring system to detect presence or cessation of EEG signals suggestive of one or more impending neuropsychiatric disorders. When the presence of EEG signals suggestive of an impending neuropsychiatric disorder is detected by the processing unit, the processing unit may be configured to immediately send signals to the first taVNS unit to automatically start sending pre-determined electric stimuli to the vagus innervated auricular skin of the wearer's first ear to which the first stimulating electrode is in contact with. When cessation of EEG signals suggestive of the impending neuropsychiatric disorder is detected by the processing unit, the processing unit may be further configured to immediately send signals to the first taVNS unit to automatically stop sending pre-determined electric stimuli to the vagus innervated auricular skin of the wearer's first ear to which the first stimulating electrode is in contact with.

BRIEF DESCRIPTION OF THE DRAWINGS

Some embodiments of the present invention are illustrated as an example and are not limited by the figures of the accompanying drawings, in which like references may indicate similar elements and in which.

DETAILED DESCRIPTION OF THE INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, may be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims may be read with the understanding that such combinations are entirely within the scope of the invention and the claims.

Figure 1:
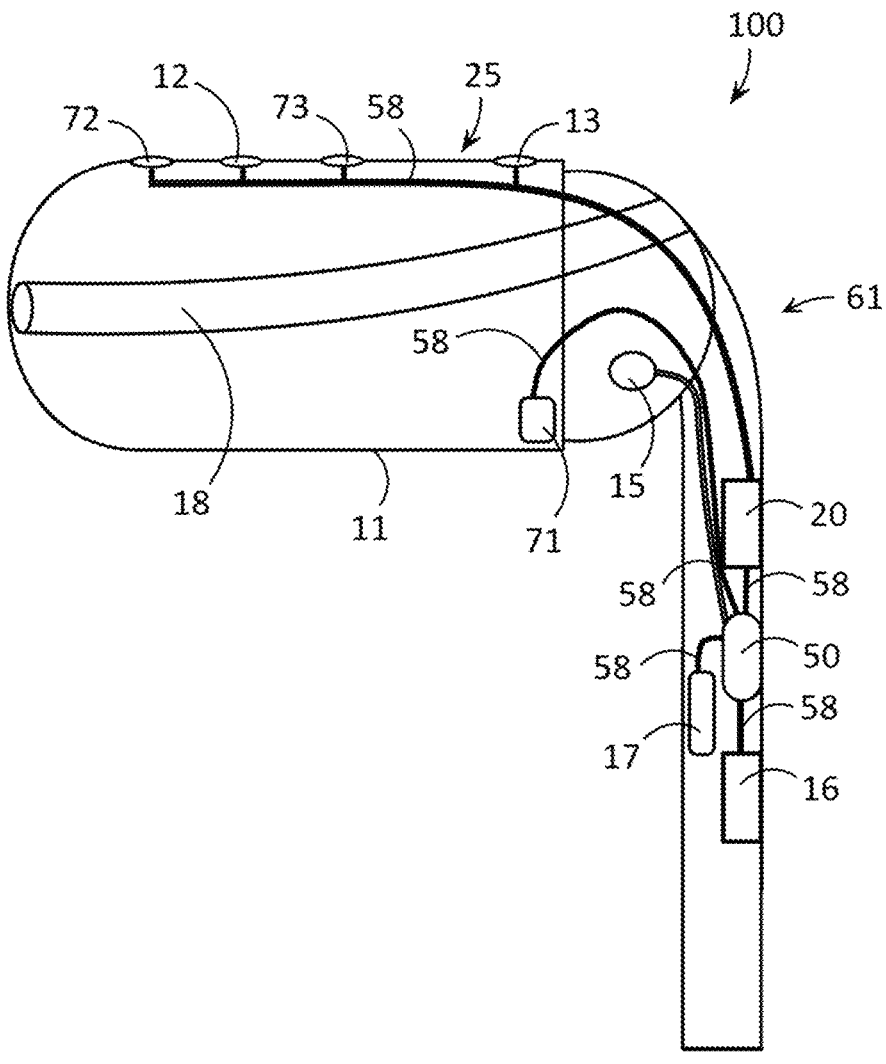
FIG. 1—FIG. 1 depicts a diagram of an example of an auricular electroencephalogram (EEG) monitoring system according to various embodiments described herein.

For purposes of description herein, the terms "upper", "lower", "left", "right", "rear", "front", "side", "vertical", "horizontal", and derivatives thereof shall relate to the invention as oriented in FIG. 1. However, one will understand that the invention may assume various alternative orientations and step sequences, except where expressly specified to the contrary. Therefore, the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The term "client device" as used herein is a type of computer or computing device comprising circuitry and configured to generally perform functions such as recording audio, photos, and videos; displaying or reproducing audio, photos, and videos; storing, retrieving, or manipulation of electronic data; providing electrical communications and network connectivity; or any other similar function. Non-limiting examples of client devices include: personal computers (PCs), workstations, servers, laptops, tablet PCs including the iPad, cell phones including iOS phones made by Apple Inc., Android OS phones, Microsoft OS phones, Blackberry phones, Apple iPads, Anota digital pens, smart watches (e.g., Apple Watch, Samsung Galaxy Watch, etc.), digital music players, or any electronic device capable of running computer software and displaying information to a user, memory cards, other memory storage devices, digital cameras, external battery packs, external charging devices, and the like. Certain types of electronic devices which are portable and easily carried by a person from one location to another may sometimes be referred to as a "portable electronic device" or "portable device". Some non-limiting examples of portable devices include: cell phones, smartphones, tablet computers, laptop computers, tablets, digital pens, wearable computers such as Apple Watch, other smartwatches, Fitbit, other wearable fitness trackers, Google Glasses, and the like.

As used herein the term "data network" or "network" shall mean an infrastructure capable of connecting two or more computers such as client devices either using wires or wirelessly allowing them to transmit and receive data. Non-limiting examples of data networks may include the internet or wireless networks or (i.e., a "wireless network") which may include BLE (Bluetooth), LoRa and LoRaWAN (and other low-power, wide-area (LPWA) networking protocols), Wi-Fi, and cellular networks. For example, a network may include a local area network (LAN), a wide area network (WAN) (e.g., the Internet), a mobile relay network, a metropolitan area network (MAN), an ad hoc network, a telephone network (e.g., a Public Switched Telephone Network (PSTN)), a cellular network, a Zigbee network, or a voice-over-IP (VOIP) network.

Although the terms "first", "second", etc. are used herein to describe various elements, these elements may not be limited by these terms. These terms are only used to distinguish one element from another element. For example, the first element may be designated as the second element, and the second element may be likewise designated as the first element without departing from the scope of the invention.

As used in this application, the term "about" or "approximately" refers to a range of values within plus or minus 15% of the specified number. Additionally, as used in this application, the term "substantially" means that the actual value is within about 10% of the actual desired value, particularly within about 5% of the actual desired value and especially within about 1% of the actual desired value of any variable, element or limit set forth herein.

A new auricular electroencephalogram (EEG) monitoring system and an automatic detection-remedy system are discussed herein. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the figures or description below.

The present invention will now be described by example and through referencing the appended figures representing preferred and alternative embodiments.

According to one embodiment consistent with the principles of the present invention, an auricular electroencephalogram (EEG) monitoring system ("the auricular EEG monitoring system") 100 is disclosed (FIGS. 1, 8-10, and 18). In some embodiments, the auricular EEG monitoring system 100 may comprise one or more auricular EEG recording modules 20 which may be configured to be coupled or engaged (e.g., frictionally coupled, engaged, retained, etc.) to the ear 902 or the peri-auricular area 903 of the wearer 900 (sometimes called "user 900"). Each auricular EEG recording module 20 may have a plurality of (at least two, but preferably more than two) EEG sensor electrodes 12, 13, 72, 73, 82, 83. These EEG sensor electrodes 12, 13, 72, 73, 82, 83, are configured to contact separate areas of the wearer's ear 902 or peri-auricular area 903. The areas that the EEG sensor electrodes 12, 13, 72, 73, 82, 83, are configured to contact are selected from at least one of the following: the external ear 902, external ear canal 904, and peri-auricular area 903. The peri-auricular area 903 refers to the portion of the head around the auricle (pinna). The peri-auricular area 903 is typically hairless. The peri-auricular area includes a portion of the head in front of the auricle (pre-auricular area) and a portion of the head above and behind the auricle (post-auricular area). The pre-auricular area is small, about one inch wide and about two inches long and curved along the anterior edge of the auricle. The post-auricular area is also small and is about one inch wide and about three inches long and curved along the superior and posterior edges of the auricle (pinna). The post-auricular area is where a behind-the-ear hearing aid is usually attached to. The pre-auricular area and the post-auricular area together is called "peri-auricular area" herein. (Anterior, posterior, superior, in front of and behind etc. all refer to the directions relative to the wearer's head when the wearer is in an upright position.) The auricular EEG recording module 20 may be configured to record EEG data of the wearer 900 via electrical activities detected by the EEG sensor electrodes 12, 13 72, 73, 82, 83. A network interface 53, 406, may be configured to generate a notification to a client device 400. A processing unit 50, 401, may be in electronic communication with the first auricular EEG recording module 20 and with the network interface 53. Preferably, the processing unit 50, 401, may be configured to analyze the EEG data recorded by the auricular EEG recording module 20 to detect presence or cessation of EEG signals suggestive of one or more neuropsychiatric disorders, and when the presence or cessation of EEG signals suggestive of one or more neuropsychiatric disorders is detected, the processing unit 50, 401, may be further configured to immediately send signals to the network interface 53 to generate a notification to the client device 400, such as to a client device 400 of a wearer 900 or a client device 400 of the wearer's healthcare provider 950.

The auricular EEG recording module 20 may be configured to record EEG data of the wearer 900 via miniature EEG sensor electrodes 12, 13, 72, 73, 82, 83, e.g., wired or wireless miniature dry EEG electrodes (wired and wireless miniature dry EEG electrodes as known in the art). The recorded EEG data may be transmitted or otherwise electronically communicated to a processing unit 50, 401. With the help of various EEG analysis algorithms (as known in the art), the processing unit 50, 401, may be configured to analyze the EEG data to detect presence or cessation of EEG signals suggestive of neuro-psychiatric disorders. The processing unit 50, 401, may also be configured to analyze the EEG data to detect presence or cessation of EEG signals suggestive of impending neuro-psychiatric disorders. These neuropsychiatric disorders include seizure, migraine, cluster headache, major depressive disorder, schizophrenia, bipolar disorder, etc.

In some embodiments, a processing unit 50, 401, of the auricular EEG monitoring system 100 may be configured to analyze the EEG data recorded by the auricular EEG recording module 20 to detect presence or cessation of EEG signals suggestive of one or more neuropsychiatric disorders which may include: seizure, migraine, cluster headache, major depressive disorder and bipolar disorder. When presence of EEG signals suggestive of one or more neuropsychiatric disorders is detected, the processing unit 50, 401, may be further configured to immediately send signals to the network interface 53 to generate a notification to a client device 400, such as to a client device 400 of a wearer 900 or a client device 400 of the wearer's healthcare provider 950. In further embodiments, the processing unit 50, 401, may be configured to analyze the EEG data recorded by the auricular EEG recording module 20 to detect presence or cessation of EEG signals suggestive of one or more impending neuropsychiatric disorders, and when the presence of EEG signals suggestive of one or more impending neuropsychiatric disorders is detected, the processing unit 50, 401, may be further configured to immediately send signals to the network interface 53 to generate a notification to the client device 400, such as to a client device 400 of a wearer 900 or a client device 400 of the wearer's healthcare provider 950.

Figure 18:
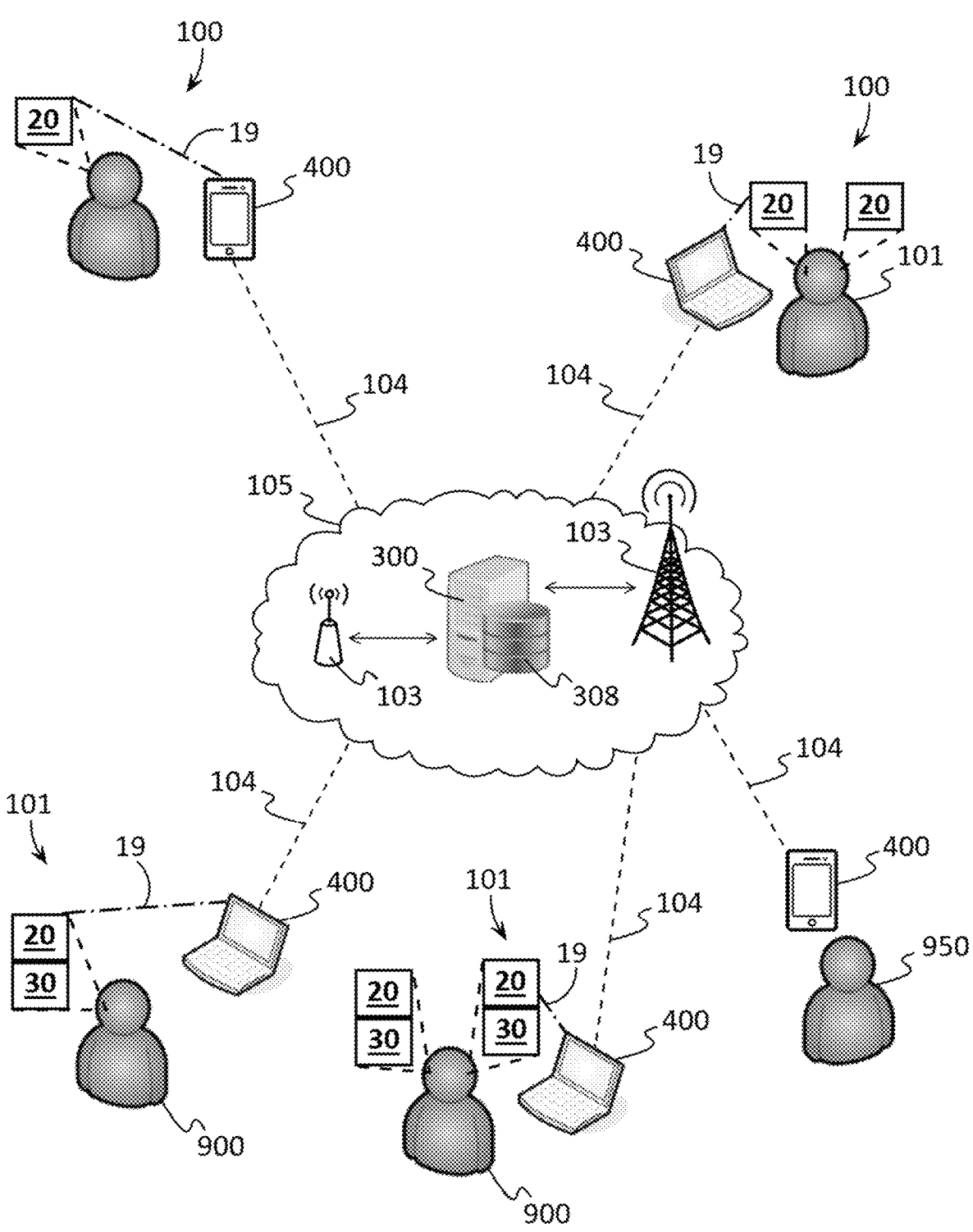
FIG. 18—FIG. 18 illustrates a schematic diagram illustrating some exemplary components of auricular EEG monitoring system and some exemplary components of an automatic detection-remedy system according to various embodiments described herein.

It should be understood that the auricular EEG monitoring system 100 may comprise one or more auricular EEG recording modules 20 as shown in FIG. 18. For example, the auricular EEG monitoring system 100 may comprise a first auricular EEG recording module 20 that may be coupled to the wearer's 900 right ear 902 or right peri-auricular area 903 and a second auricular EEG recording module 20 that may be coupled to the wearer's 900 left ear 902 or left peri-auricular area 903. The first auricular EEG recording module 20 may include a plurality of (at least two, but preferably more than two) EEG sensor electrodes, 12, 13, 72, 73, 82, 83. These EEG sensor electrodes are configured to contact separate areas of the wearer's right ear 902 or right peri-auricular area 903. The areas that the EEG sensor electrodes 12, 13, 72, 73, 82, 83, may be configured to contact are selected from at least one of the following: the right external ear 902, right external ear canal 904, and right peri-auricular area 903. Likewise, the second auricular EEG recording module 20 may include a plurality of (at least two, but preferably more than two) EEG sensor electrodes 12, 13, 72, 73, 82, 83. These EEG sensor electrodes 12, 13, 72, 73, 82, 83 may be configured to contact separate areas of the wearer's left ear 902 or left peri-auricular area 903. The areas that the EEG sensor electrodes 12, 13, 72, 73, 82, 83 may be configured to contact may be selected from at least one of the following: the left external ear 902, left external ear canal 904, and left peri-auricular area 903. The second auricular EEG recording module 20 may also be configured to record EEG data of the wearer 900, and the second EEG recording module 20 may also be in electronic communication with the processing unit 50 so that the processing unit 50 may use EEG data from the first auricular EEG recording module 20 and the second auricular EEG recording module 20 to detect the presence or cessation of EEG signals suggestive of one or more neuropsychiatric disorders and/or to detect the presence or cessation of EEG signals suggestive of one or more impending neuropsychiatric disorders.

In preferred embodiments, the auricular EEG monitoring system 100 may comprise a miniature auricular EEG recording module 20 that may include a plurality of miniature EEG sensor electrodes 12, 13. 72, 73, 82, 83, that may be coupled to or contained in an EEG recording housing 11. An EEG recording housing 11 may be attached to the head 901, preferably to the external ear canal 904 or external ear 902 (such as the skin of the cavum-concha 907, cymba-concha 906,) or the peri-auricular area 903. All of the EEG sensor electrodes 12, 13, 72, 73, 82, 83, are configured to contact separate areas selected from at least one of the following: the external ear canal 904, external ear 902 and peri-auricular area 903. The locations for the EEG sensor electrodes to contact are separate from each other. (As referred to herein, the external ear canal 904 refers to the part of the ear 902 that connects the visible outer ear (pinna) to the middle ear, essentially the tube that carries sound waves to the eardrum). The anatomy of human external ear 902 and head 901 proximate to the ear 902 is shown in FIG. 3.

Figure 2:
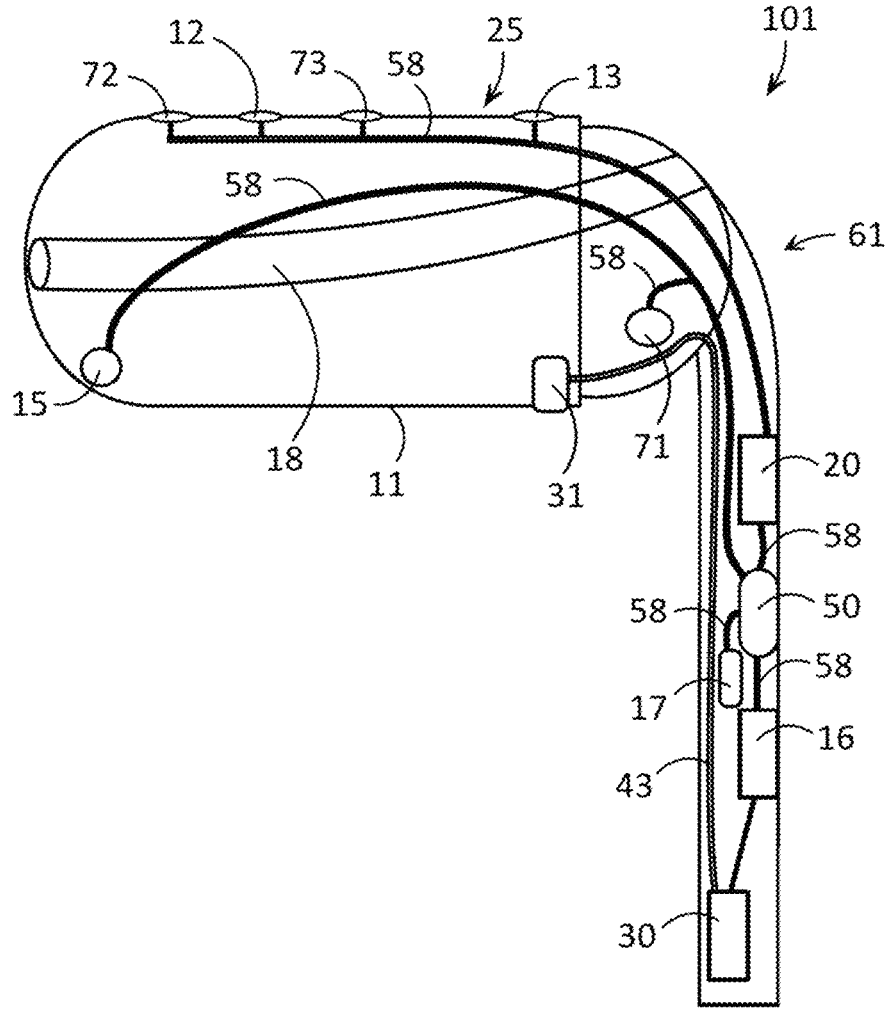
FIG. 2—FIG. 2 illustrates a diagram of an example of an automatic detection-remedy system according to various embodiments described herein.

In some embodiments, an EEG recording housing 11 of an auricular EEG monitoring system 100 and/or an automatic detection-remedy system 101 may be configured in any size and shape that may be suitable for being attached and/or frictionally coupled to the external ear 902, in the external ear canal 904 or peri-auricular area 903. In some embodiments, an EEG recording housing 11 may comprise a sound conduit 18 which may extend through the EEG recording housing 11 (such as shown in FIGS. 1 and 2) and which may facilitate the ability of sound to enter the ear 902. A sound conduit 18 may comprise an opening, channel, conduit, etc., which may extend through a portion of the EEG recording housing 11 so that sound waves may pass through the sound conduit 18 to facilitate or enable the wearer 900 to hear sounds in the environment.

Figure 3:
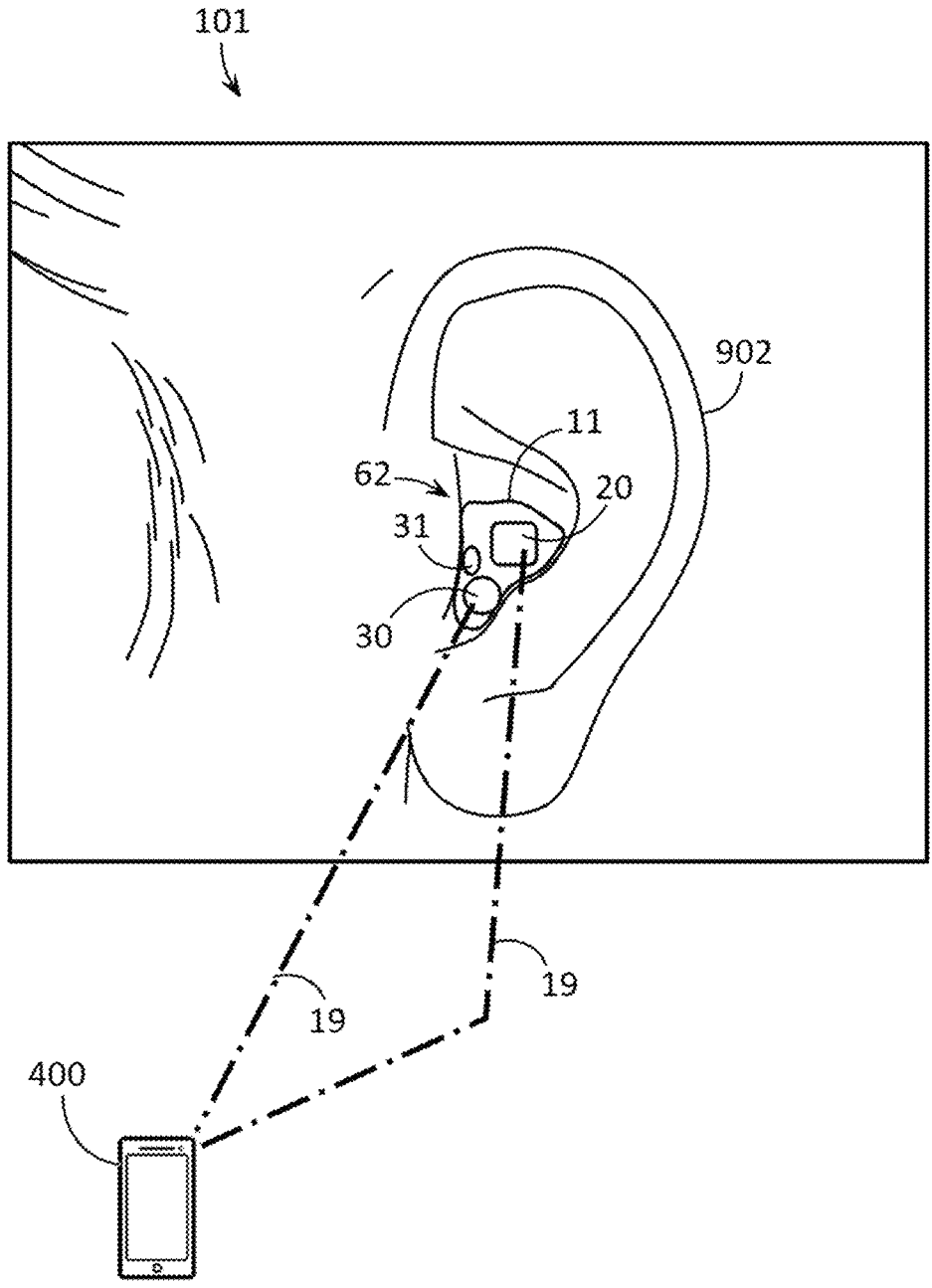
FIG. 3—FIG. 3 depicts a diagram of another example of an automatic detection-remedy system according to various embodiments described herein.
Figure 9:
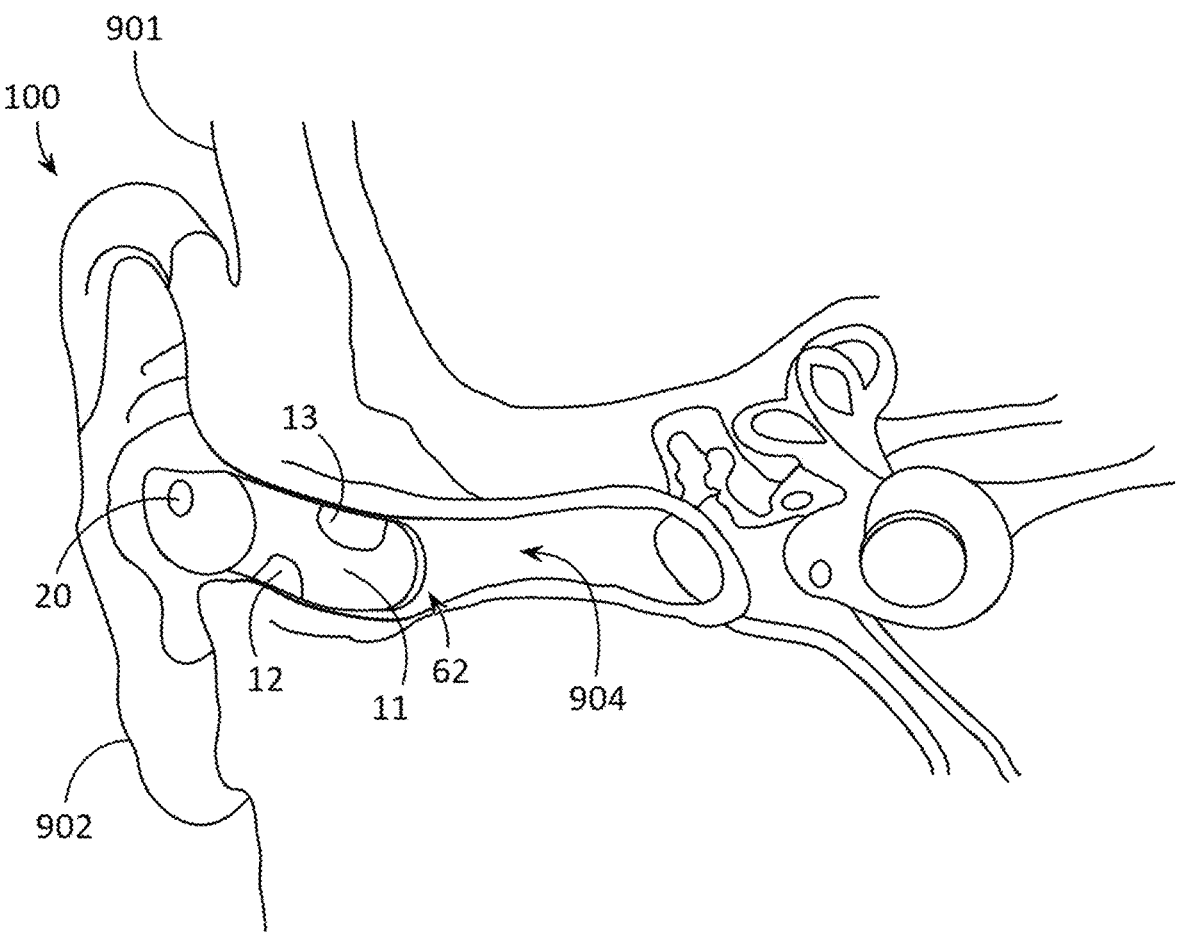
FIG. 9—FIG. 9 depicts a diagram of an example of an auricular electroencephalogram (EEG) monitoring system having an in-the-ear structure engaged or coupled to the ear of a wearer according to various embodiments described herein.
Figure 12:
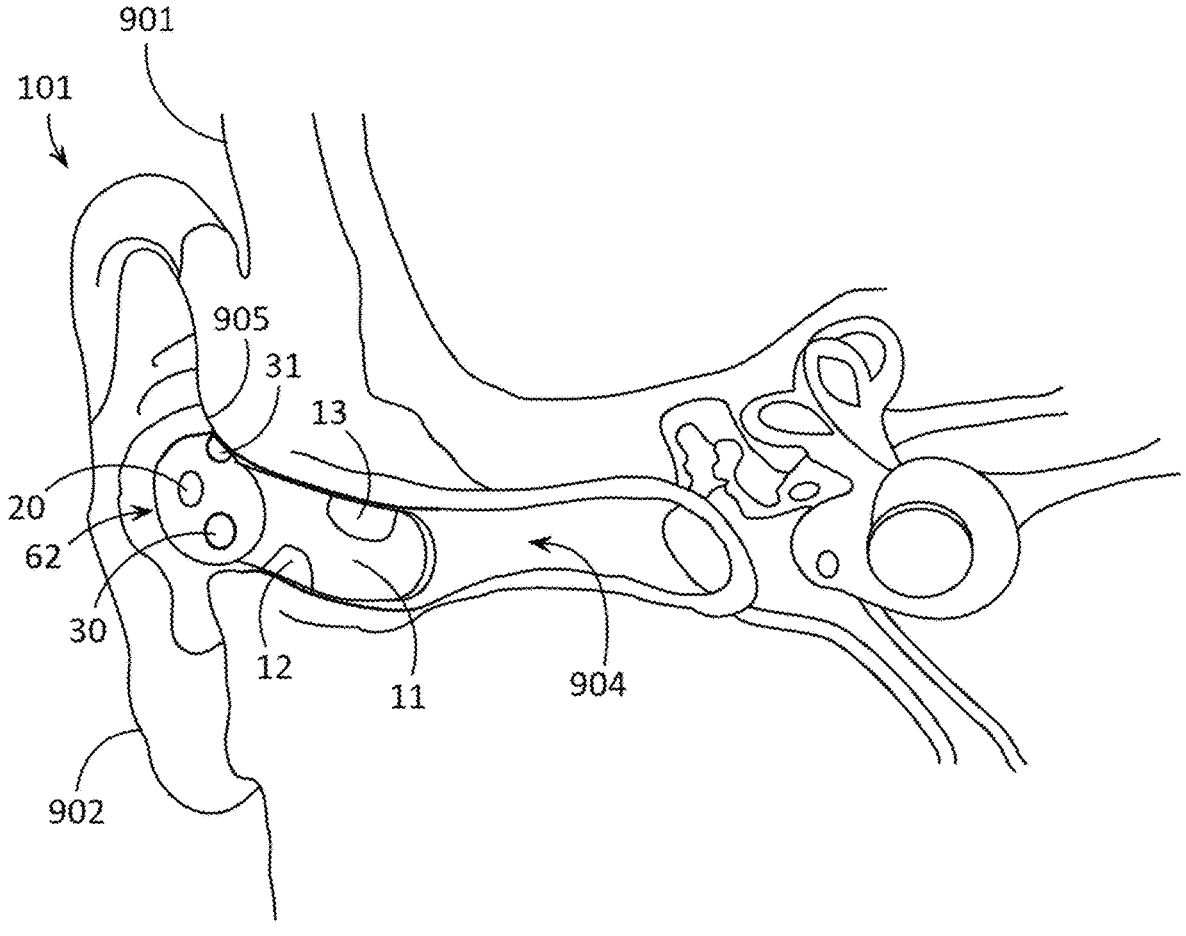
FIG. 12—FIG. 12 illustrates a diagram of an example of an automatic detection-remedy system having an in-the-ear structure engaged or coupled to the ear of a wearer according to various embodiments described herein FIG. 13

In some embodiments, an EEG recording housing 11 of an auricular EEG monitoring system 100 and/or an automatic detection-remedy system 101 may be shaped or configured as an in-the-ear structure 62 so that all or a majority of the EEG recording housing 11 may be inserted into a portion of the external ear canal 904, such as shown in FIGS. 3, 9, and 12. Example in-the-ear structures 62 include: in-the-ear (ITE) hearing aids, in-the-canal (ITC), and the like.

Figure 8:
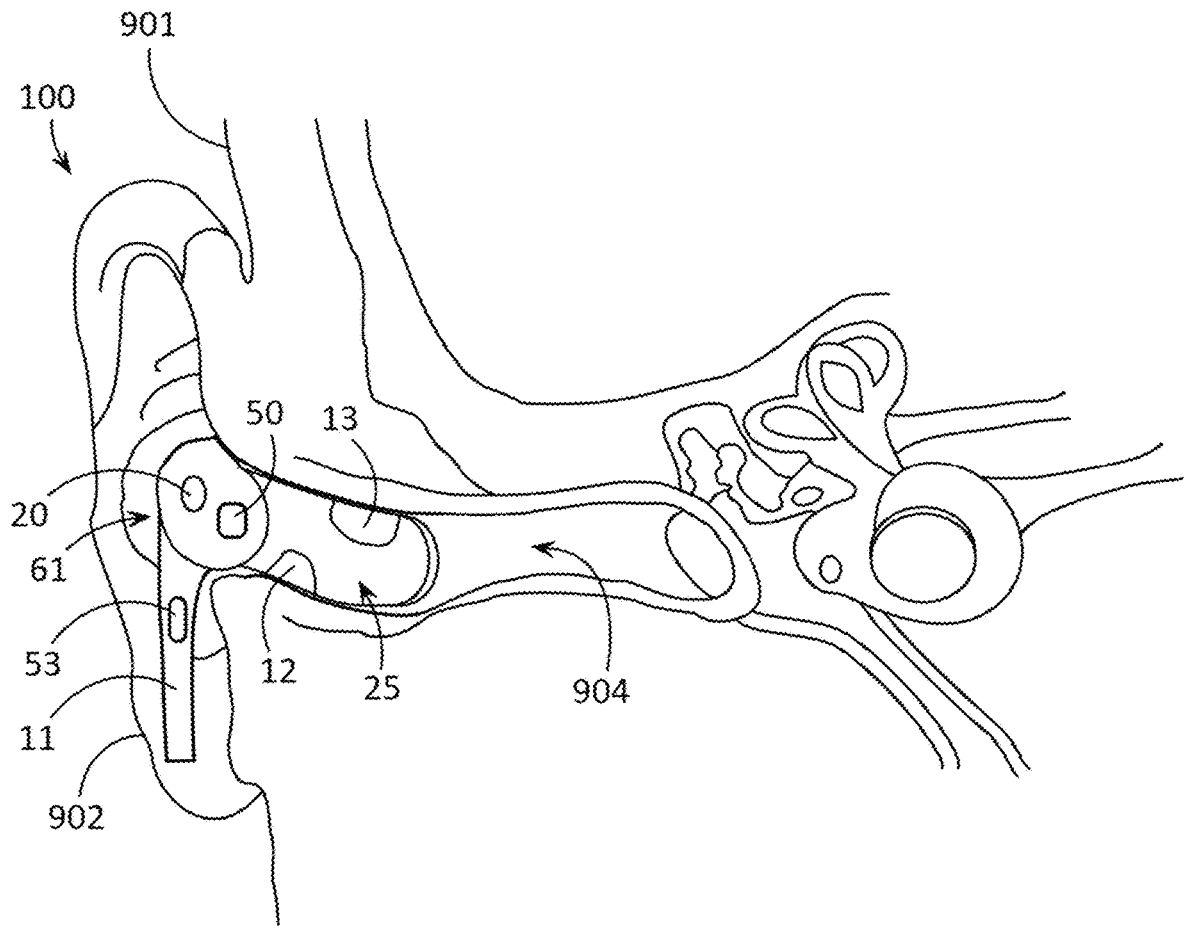
FIG. 8—FIG. 8 shows a diagram of an example of an auricular electroencephalogram (EEG) monitoring system having an earbud style structure engaged or coupled to the ear of a wearer according to various embodiments described herein.
Figure 11:
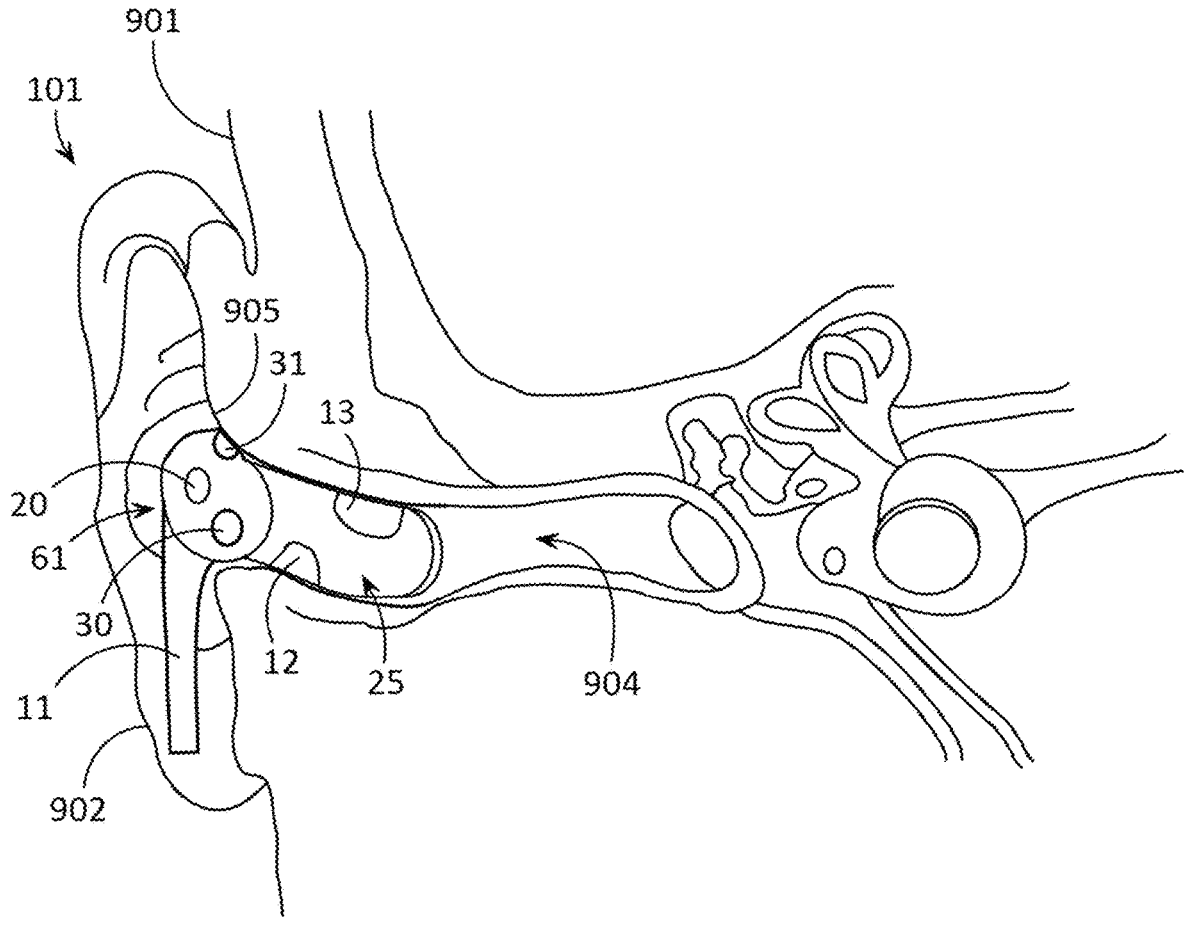
FIG. 11—FIG. 11 shows a diagram of an example of an automatic detection-remedy system having an earbud style structure engaged or coupled to the ear of a wearer according to various embodiments described herein.

In some embodiments, an EEG recording housing 11 of an auricular EEG monitoring system 100 and/or an automatic detection-remedy system 101 may be shaped or configured as an earbud style structure 61. Optionally, an earbud style structure 61 may be shaped and sized so that a horizontal portion 25 of the EEG recording housing 11 may be inserted into a portion of the external ear canal 904 and ear 902 such as shown in FIGS. 8 and 11. Example, earbud style structures 61 include: earbuds, ear phones, Apple AirPods®, and the like.

Figure 19:
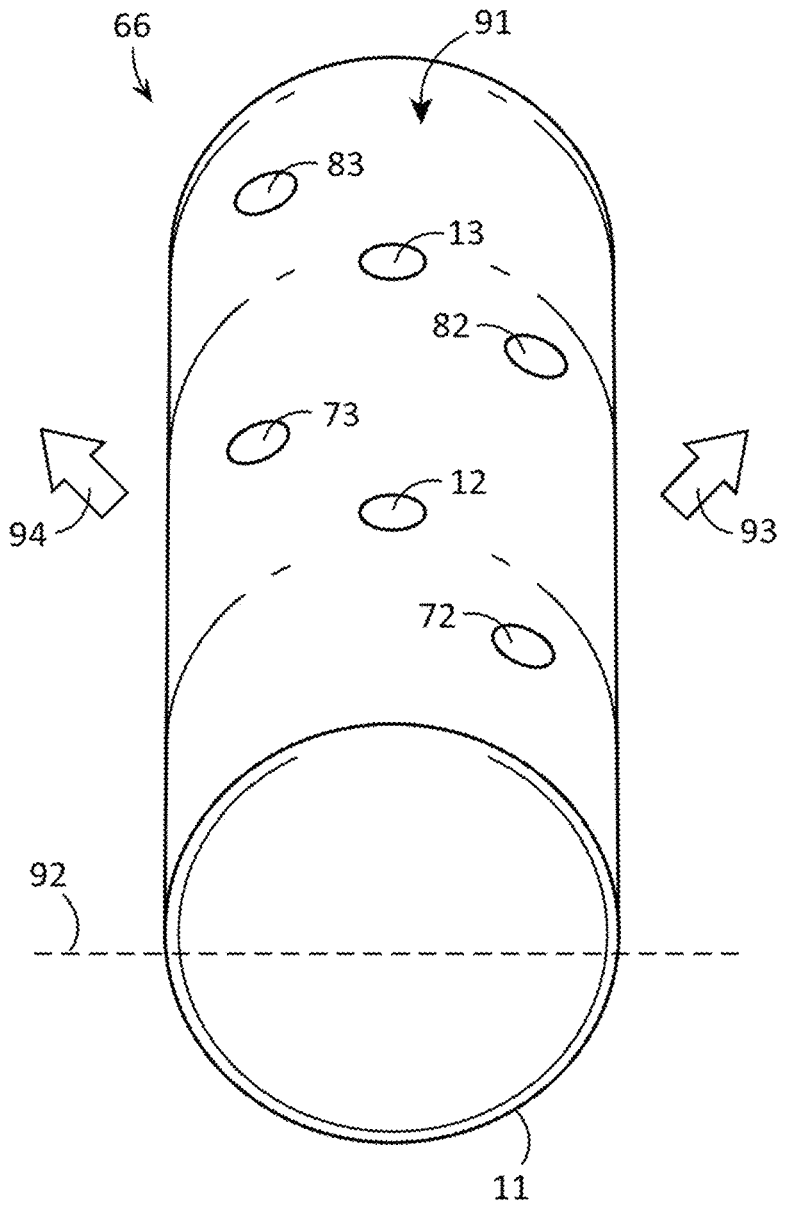
FIG. 19—FIG. 19 illustrates a perspective diagram of an example of a tubular-shaped structure for housing of the EEG sensor electrodes and some exemplary locations for the EEG sensor electrodes according to various embodiments described herein.
Figure 20:
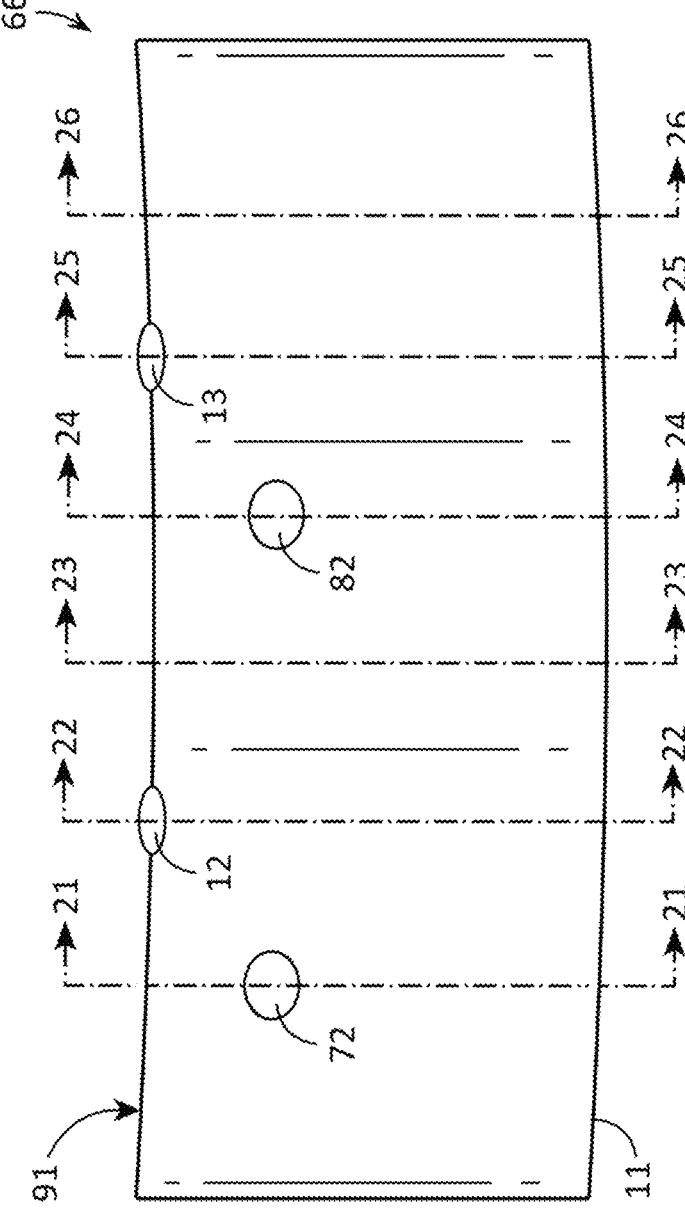
FIG. 20—FIG. 20 illustrates a side elevation diagram of an example of a tubular-shaped structure for housing of the EEG sensor electrodes and some exemplary locations for the EEG sensor electrodes according to various embodiments described herein.
Figure 21:
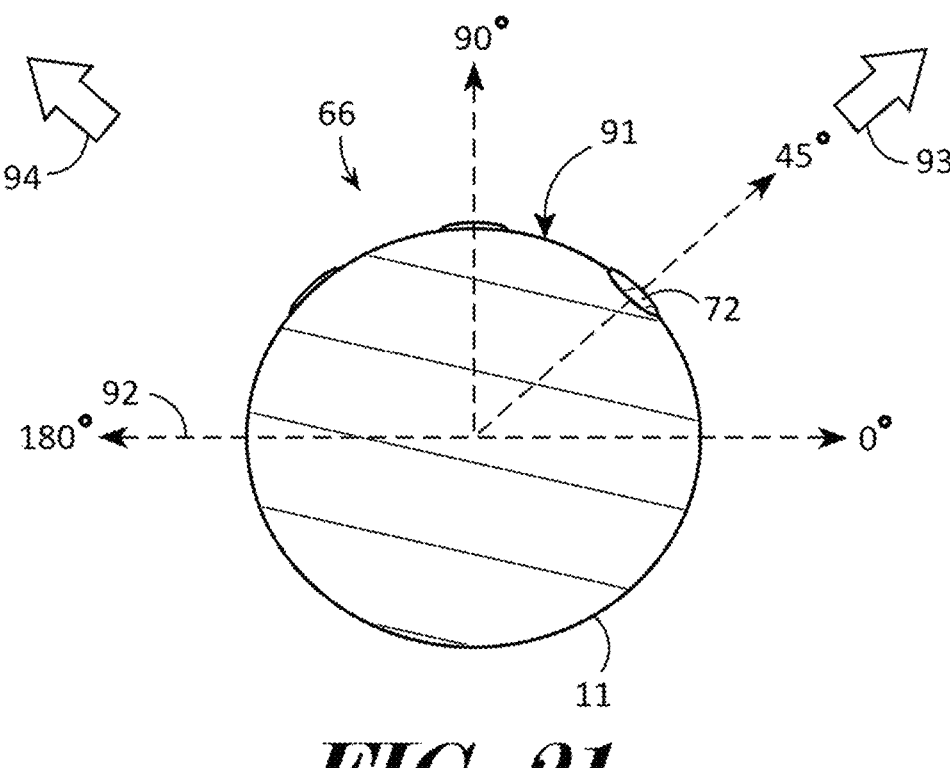
FIG. 21—FIG. 21 shows a sectional, through line 21-21 shown in FIG. 20, elevation view of an example of a tubular-shaped structure for housing of the EEG sensor electrodes and some exemplary locations for the EEG sensor electrodes according to various embodiments described herein.
Figure 22:
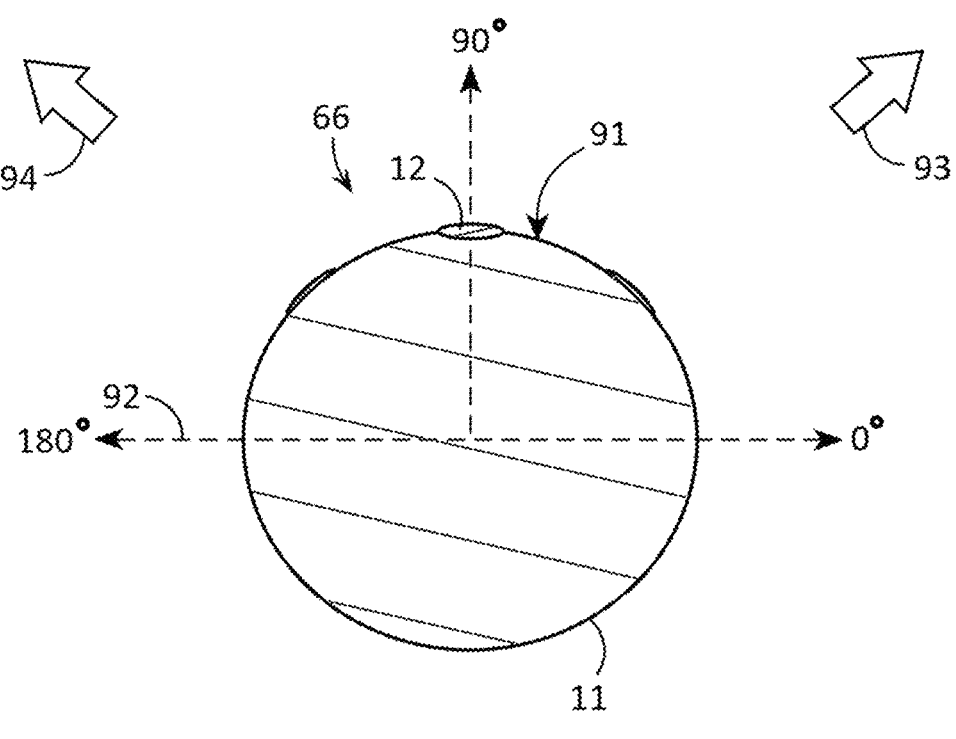
FIG. 22—FIG. 22 depicts a sectional, through line 22-22 shown in FIG. 20, elevation view of an example of a tubular-shaped structure for housing of the EEG sensor electrodes and some exemplary locations for the EEG sensor electrodes according to various embodiments described herein.
Figure 23:
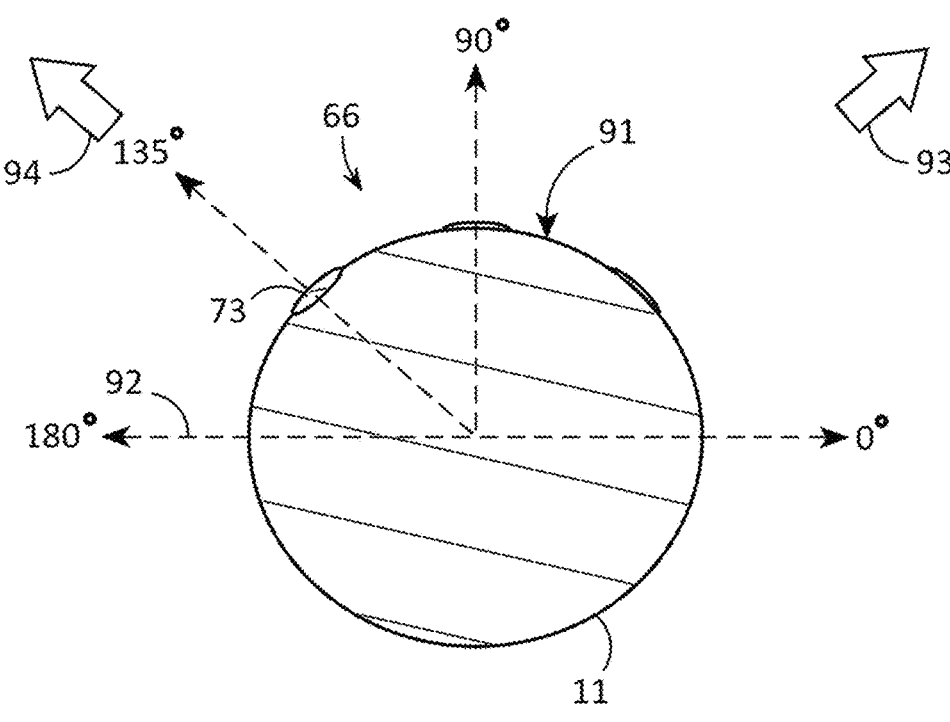
FIG. 23—FIG. 23 shows a sectional, through line 23-23 shown in FIG. 20, elevation view of an example of a tubular-shaped structure for housing of the EEG sensor electrodes and some exemplary locations for the EEG sensor electrodes according to various embodiments described herein.
Figure 24:
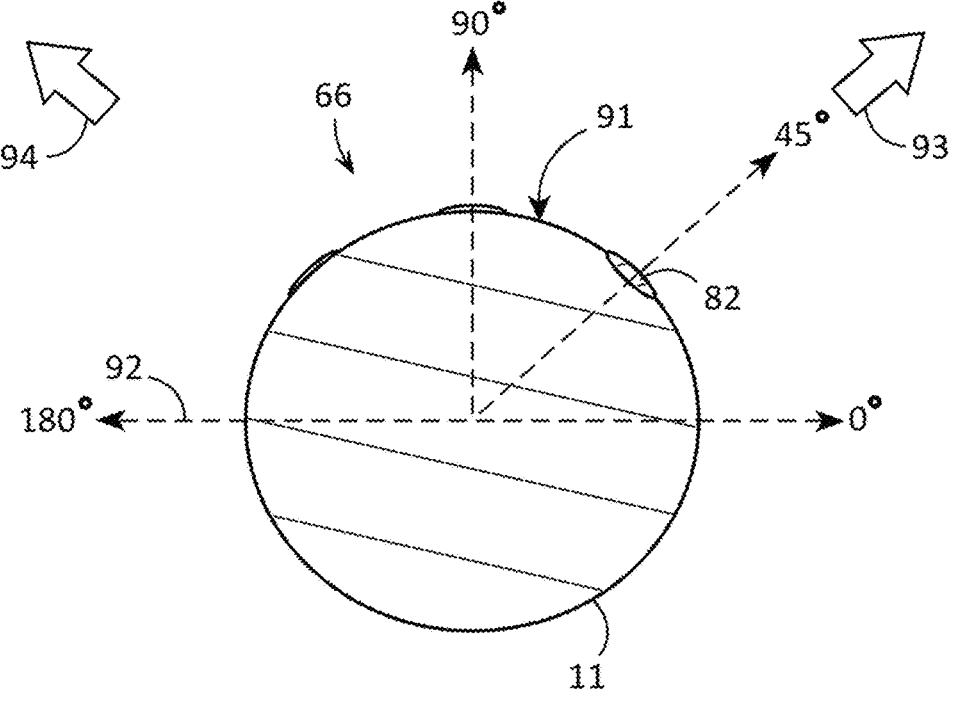
FIG. 24—FIG. 24 illustrates a sectional, through line 24-24 shown in FIG. 20, elevation view of an example of a tubular-shaped structure for housing of the EEG sensor electrodes and some exemplary locations for the EEG sensor electrodes according to various embodiments described herein.
Figure 25:
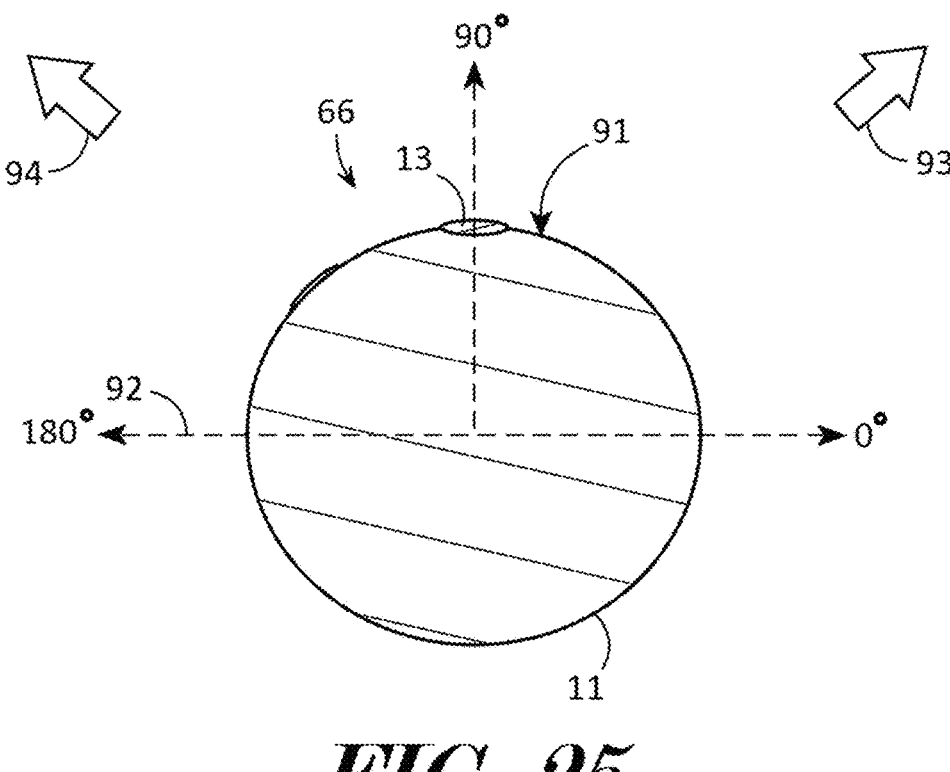
FIG. 25—FIG. 25 depicts a sectional, through line 25-25 shown in FIG. 20, elevation view of an example of a tubular-shaped structure for housing of the EEG sensor electrodes and some exemplary locations for the EEG sensor electrodes according to various embodiments described herein.
Figure 26:
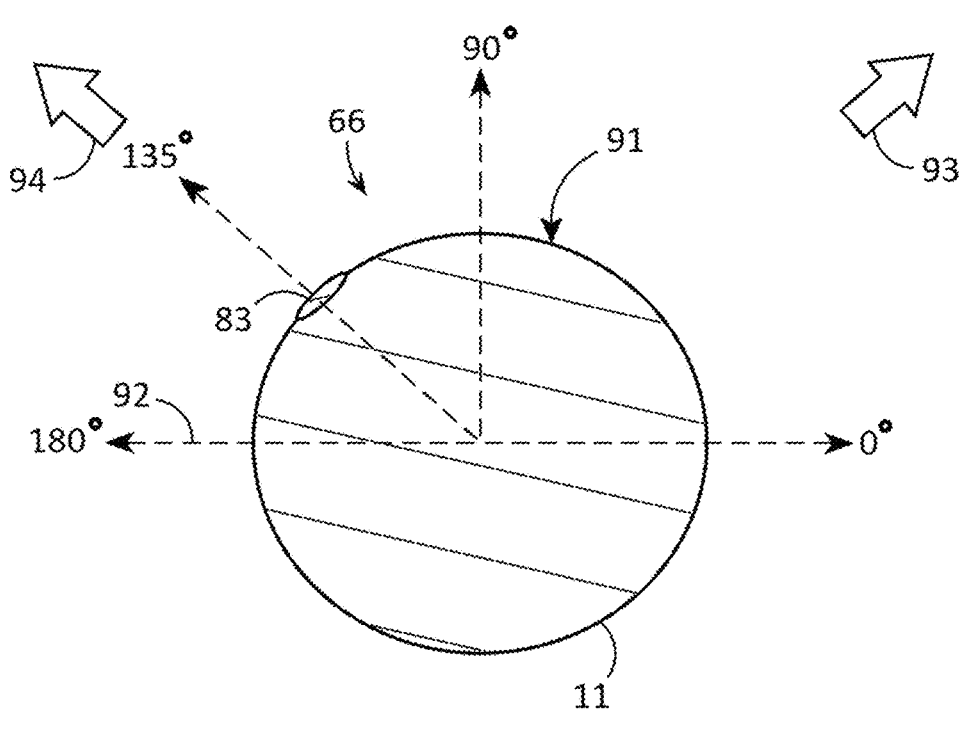
FIG. 26—FIG. 26 shows a sectional, through line 26-26 shown in FIG. 20, elevation view of an example of a tubular-shaped structure for housing of the EEG sensor electrodes and some exemplary locations for the EEG sensor electrodes according to various embodiments described herein.

In some embodiments, an EEG recording housing 11 of an auricular EEG monitoring system 100 and/or an automatic detection-remedy system 101 may be shaped or configured as a tubular-shaped structure 66 and all of the EEG sensor electrodes 12, 13, 72, 73, 82, 83 are configured to be located at the surface 91 of the tubular-shaped structure 66 and so that all of the EEG sensor electrodes 12, 13, 72, 73, 82, 83 are housed in the tubular-shaped structure 66. In preferred embodiments, one or more of the EEG sensor electrodes 12, 13, 72, 73, 82, 83 is/are configured to be located at the upper surface 91 (upper surface at approximately 90 degrees above horizontal level 92, as shown by electrodes 12, 13, in FIGS. 19, 22, 25) of the tubular-shaped structure 66. In preferred embodiments, one or more of the EEG sensor electrodes is/are configured to be located at between 0 and 90 degrees, and more preferably at approximately 45 degrees (plus or minus fifteen degrees) above horizontal level 92 of the tubular structure 66 and is/are configured to face forward-upward direction 93 (e.g., as shown by electrodes 72, 82, in FIGS. 19, 21, 24). In preferred embodiments, one or more of the EEG sensor electrodes is/are configured to be located at between 90 and 180 degrees, and more preferably at approximately 135 degrees (plus or minus fifteen degrees) above the horizontal level 92 of the tubular structure 66 and is/are configured to face backward-upward direction 94 (e.g., as shown by electrodes 73, 83, in FIGS. 19, 23, 26). (Upper surface, horizontal level, forward, backward and upward all refer to directions relative to the head 901 of the wearer 900 with the wearer in upright position after the tubular-shaped structure 66 has been inserted into the wearer's external ear canal 904.)

In some embodiments of an auricular EEG monitoring system 100, an EEG recording module 20, a processing unit 50, and a network interface 53 may be housed or contained in an earbud style structure 61 (FIGS. 1 and 8), and all of the EEG sensor electrodes 12, 13, 72, 73, 82, 83, may be located on the surface of the horizontal portion 25 of the earbud-style structure 61. Preferably, the horizontal portion 25 of the earbud-style structure 61 may comprise or may be made from an elastic flexible and adaptable material. The material of the horizontal portion 25 of the earbud-style structure is configured to have appropriate elasticity flexibility and adaptability such that all of the EEG sensor electrodes 12, 13, 72, 73, 82, 83, of the EEG recording module 20 are naturally in close contact (provided by the elastic, flexible, and adaptable characteristics of the material so that it can conform to the contours of the external ear canal 904 and snugly fill the interior of the external ear canal 904.) with the skin of the external ear canal 904 of the wearer's ear 902 when the horizontal portion 25 of the earbud-style structure 61 is inserted into the external ear canal 904 of the wearer's ear 902.

In some embodiments of an automatic detection-remedy system 101, an EEG recording module 20, a processing unit 50, a taVNS unit 30, and a network interface 53 may be housed or contained in an earbud style structure 61 (FIGS. 2, 7, and 11), and all of the EEG sensor electrodes 12, 13, 72, 73, 82, 83, and the stimulating electrode 31 may be located on the surface of the horizontal portion 25 of the earbud-style structure 61. Preferably, the earbud-style structure 61 may comprise or may be made from an elastic flexible and adaptable material. The material for the earbud-style structure is configured to have appropriate elasticity flexibility and adaptability such that the stimulating electrode 31 and all of the EEG sensor electrodes 12, 13, 72, 73, 82, 83, of the EEG recording module 20 are naturally in close contact (provided by the elastic, flexible, and adaptable characteristics of the material so that it can conform to the contours of the external ear canal 904 and snugly fill the interior of the external ear canal 904) with the skin of the external ear canal 904 of the wearer's ear 902 when the earbud-style structure 61 is inserted into the external ear canal 904 of the wearer's ear 902 (FIG. 11). Attaching and removing all of the EEG sensor electrodes 12, 13, 72, 73, 82, 83, and the stimulating electrode 31 will be as easy as inserting and removing the earbud style structure 61 from the wearer's external ear canal 904.

Figure 5:
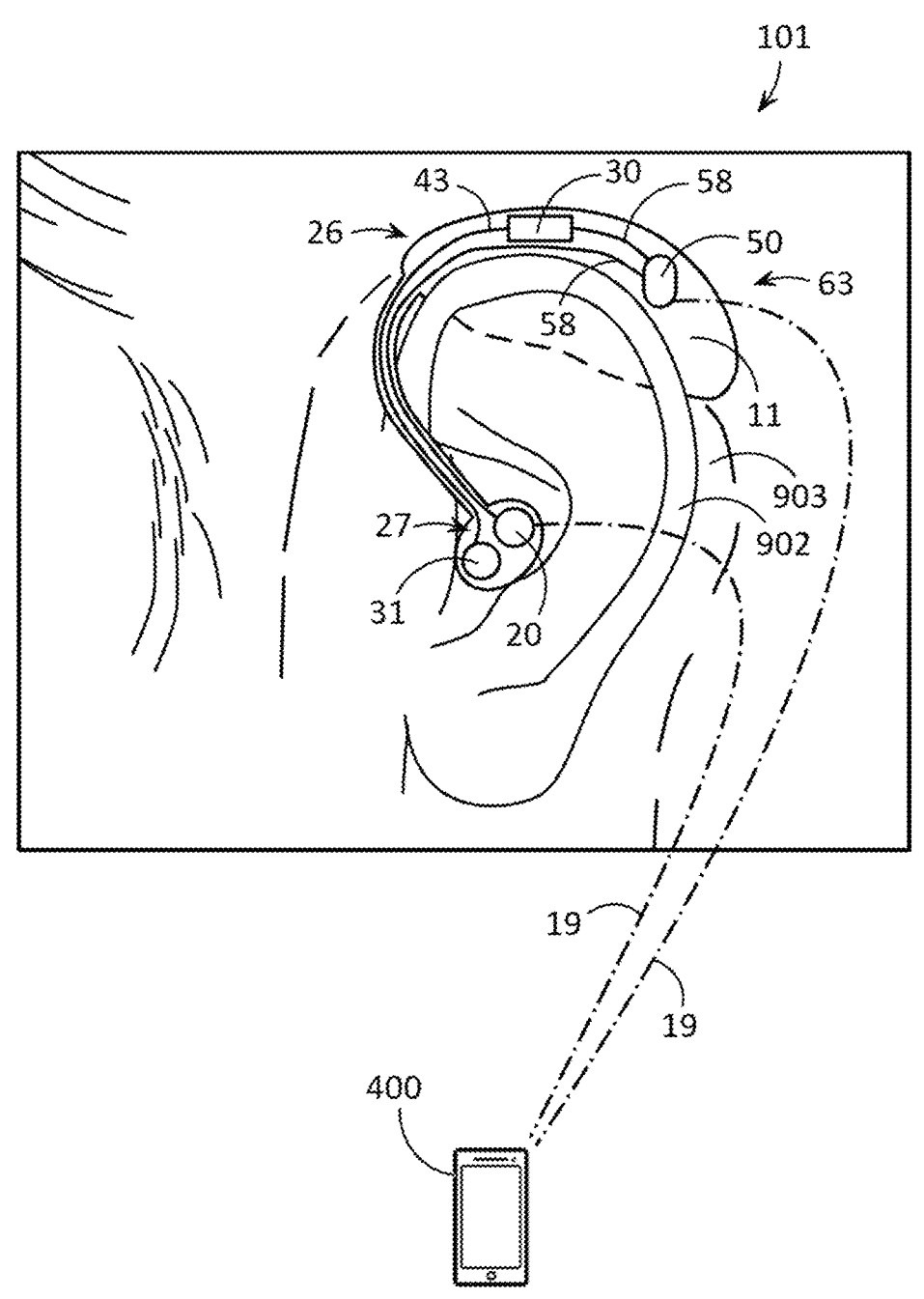
FIG. 5—FIG. 5 shows a diagram of a further example of an automatic detection-remedy system according to various embodiments described herein.
Figure 10:
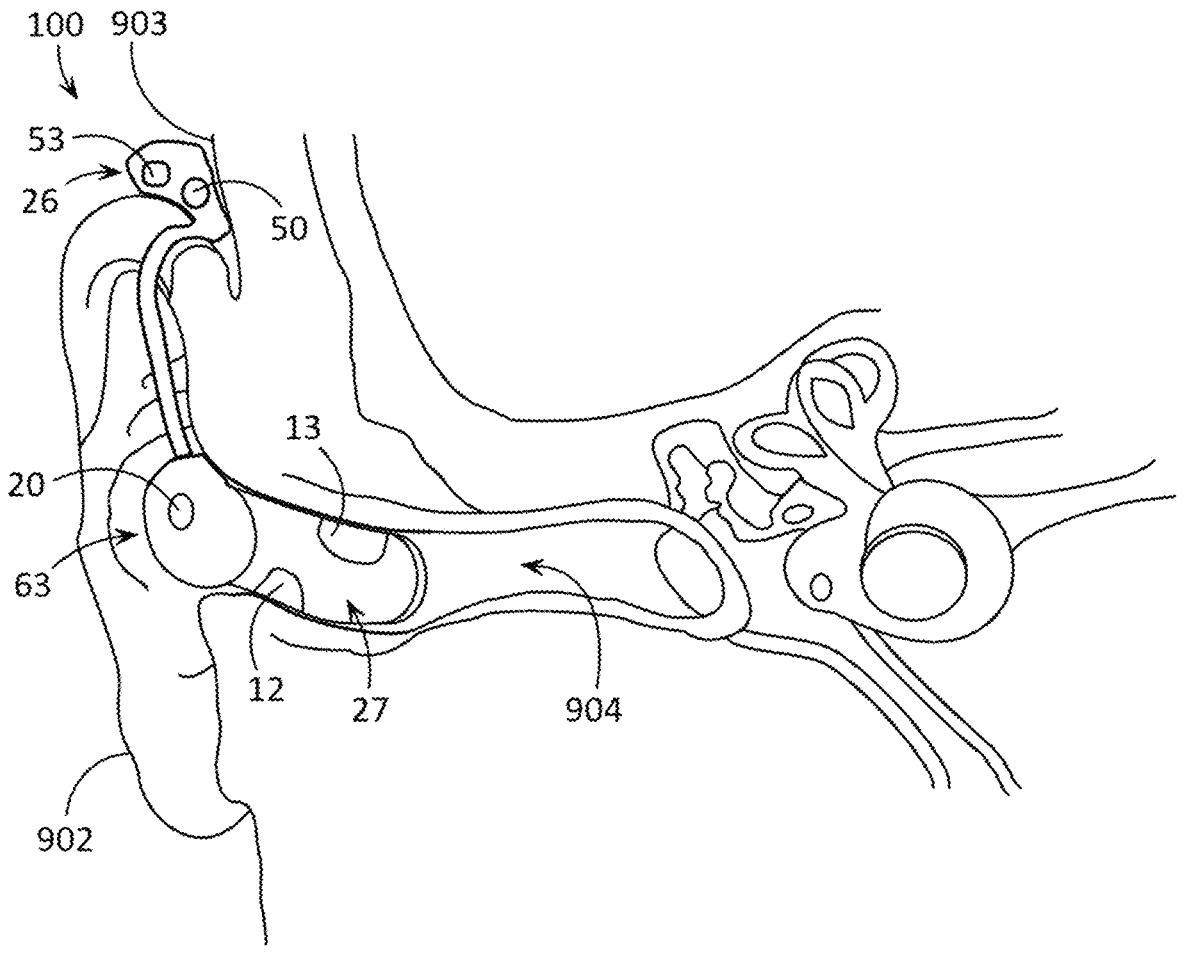
FIG. 10—FIG. 10 illustrates a diagram of an example of an auricular electroencephalogram (EEG) monitoring system having a behind-the-ear structure engaged or coupled to the ear of a wearer according to various embodiments described herein.
Figure 13:
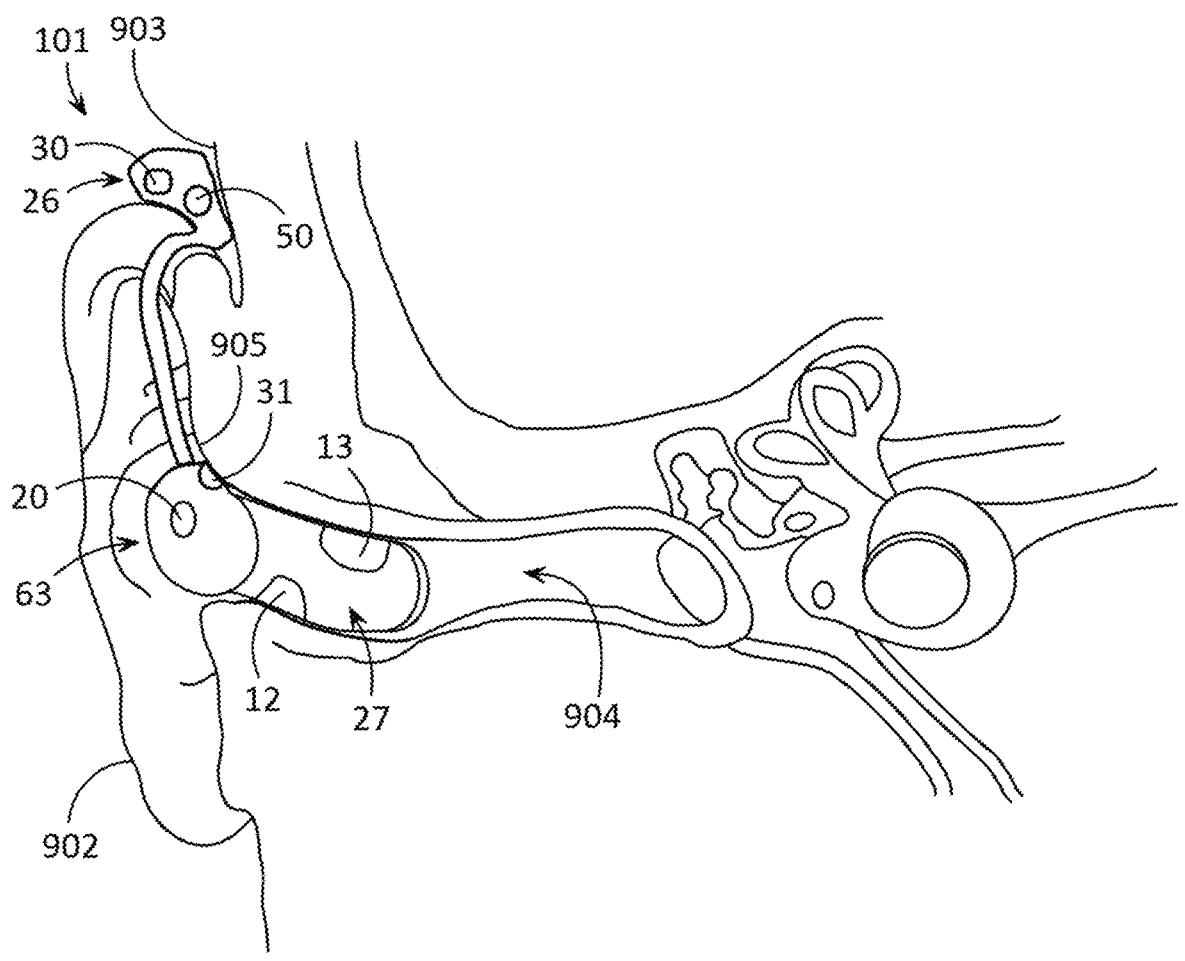
—FIG. 13 depicts a diagram of an example of an automatic detection-remedy system having a behind-the-ear structure engaged or coupled to the ear of a wearer according to various embodiments described herein FIG. 14
Figure 14:
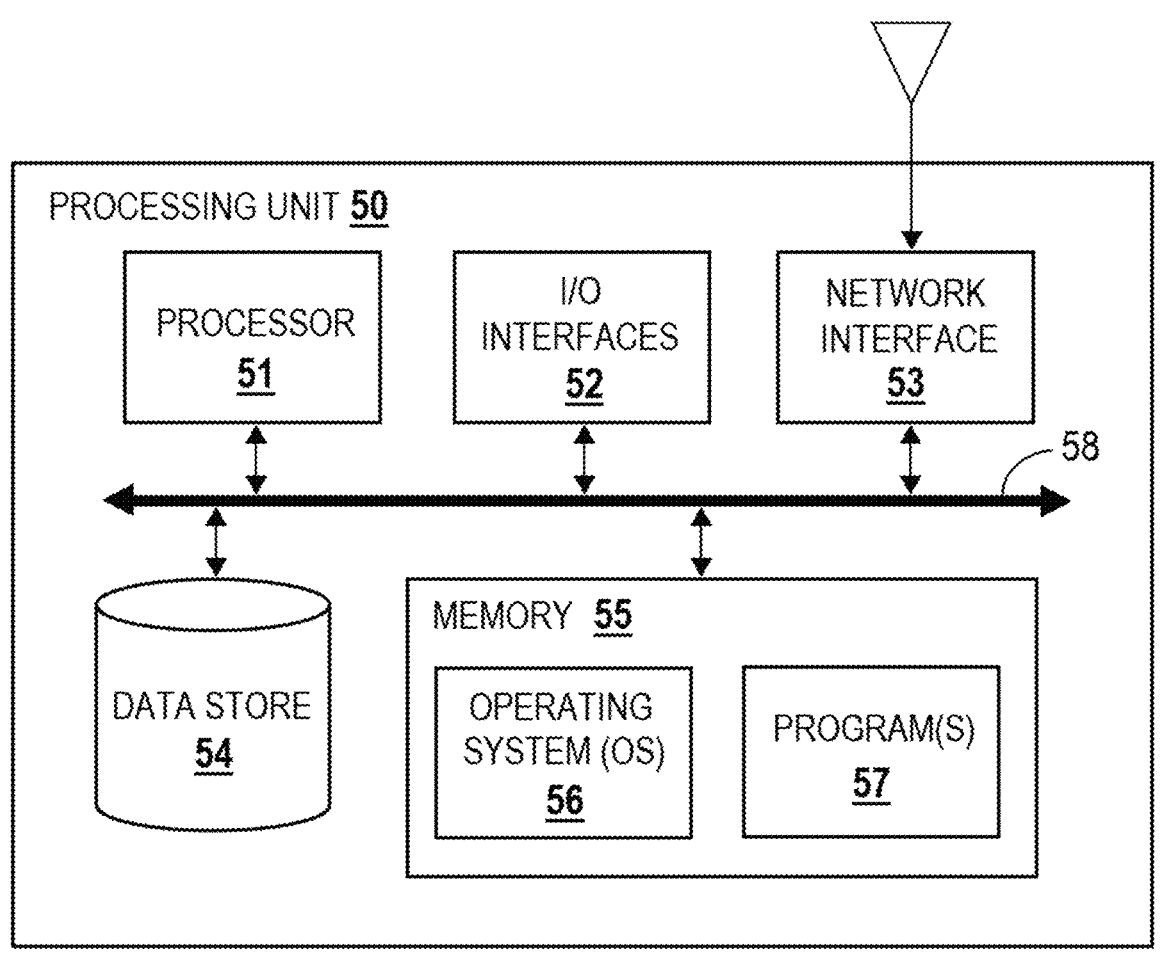
—FIG. 14 illustrates a block diagram showing some exemplary components of an example of a processing unit for an EEG monitoring system according to various embodiments described herein.
Figure 15:
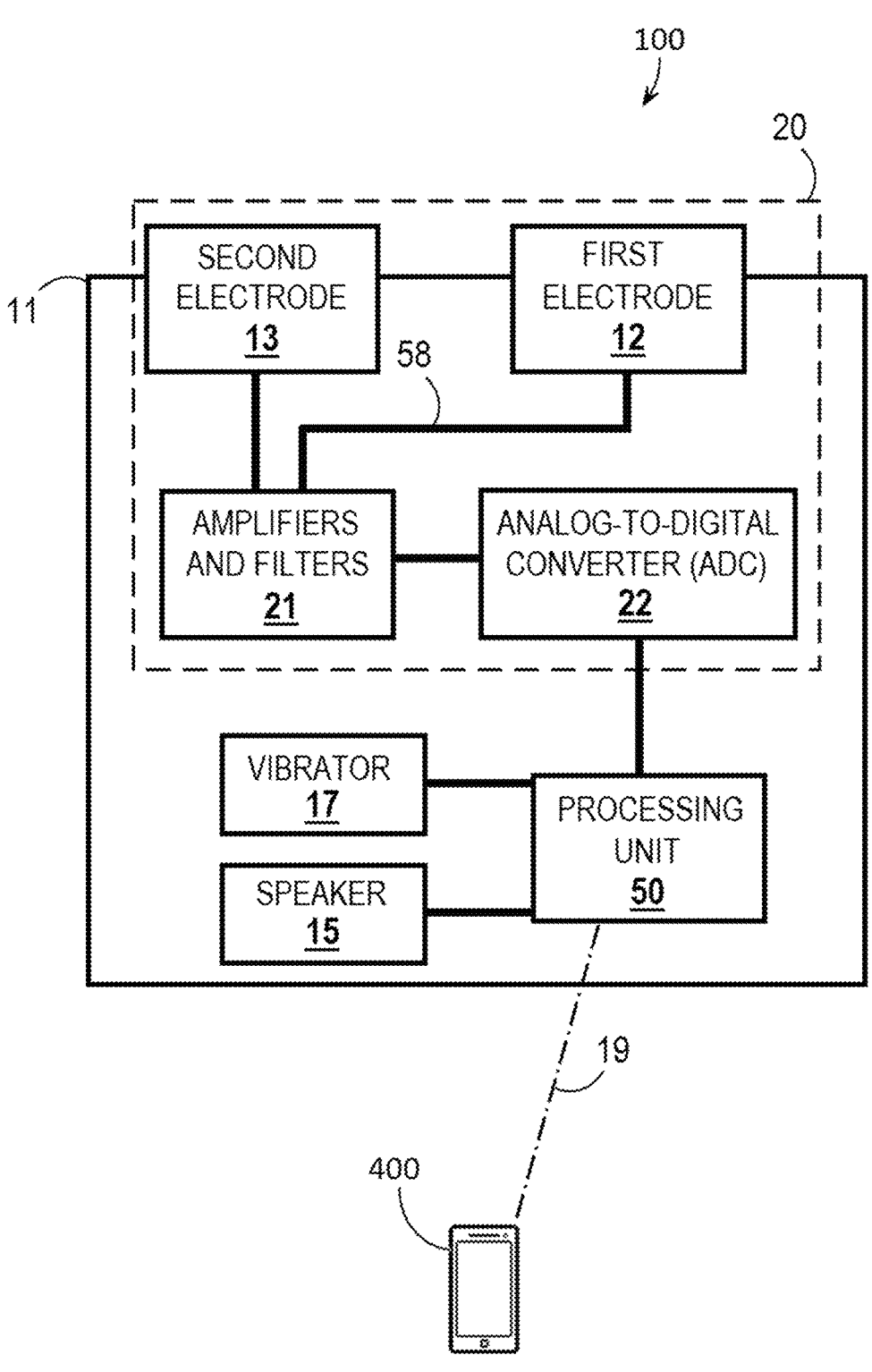
FIG. 15—FIG. 15 shows a block diagram showing some exemplary components of an example of an auricular EEG monitoring system according to various embodiments described herein.

In some embodiments, an EEG recording housing 11 of an auricular EEG monitoring system 100 and/or an automatic detection-remedy system 101 may be shaped or configured as a behind-the-ear structure 63 (e.g. a behind-the-ear-hearing-aid structure) as shown in FIGS. 5, 10, and 13. The behind-the-ear structure 63 may comprise a behind-the-ear portion 26 and an in-the-ear portion 27. Generally, a behind-the-ear structure 63 may be shaped and sized so that all or a majority of the behind-the-ear portion 26 may be positioned behind the ear 902, such as to contact the post-auricular part of the peri-auricular area 903, as shown in FIGS. 5, 10, and 13, while an in-the-ear portion 27 may be sized and shaped to be inserted into the ear 902, such as into the external ear canal 904. Example behind-the-ear structures 63 include behind-the-ear (BTE) receiver-in-the-ear (RITE), CROS/BiCROS (CROS stands for "Contralateral Routing of Signals" and BiCROS stands for "Bilateral Contralateral Routing of Signals"), and the like.

In some embodiments of an auricular EEG monitoring system 100, an EEG recording module 20, a processing unit 50, and a network interface 53 may be housed or contained in a behind-the-ear structure 63, and all of the EEG sensor electrodes 12, 13, 72, 73, 82, 83, may be located on the surface of the in-the-ear portion 27 of the behind-the-ear structure 63. Preferably, the in-the-ear portion 27 may comprise or may be made from an elastic flexible and adaptable material. The material for the in-the-ear portion is configured to have appropriate elasticity flexibility and adaptability such that all of the EEG sensor electrodes 12, 13, 72, 73, 82, 83, of the EEG recording module 20 are naturally in close contact (provided by the elastic, flexible, and adaptable characteristics of the resilient material so that it can conform to the contours of the external ear canal 904 and snugly fill the interior of the external ear canal 904) with the skin of the external ear canal 904 of the wearer's ear 901 when the in-the-ear portion 27 is inserted into the external ear canal 904 of the wearer's ear 901 (FIG. 10).

In some embodiments of an automatic detection-remedy system 101, an EEG recording module 20, a taVNS unit 30, a processing unit 50, and a network interface 53 may be housed or contained in a behind-the-ear structure 63, and all of the EEG sensor electrodes 12, 13, 72, 73, 82, 83, and stimulating electrode 31 may be located on the surface of the in-the-ear portion 27 of the behind-the-ear structure 63. Preferably, the in-the-ear portion 27 may comprise or may be made from an elastic flexible and adaptable material. The elastic flexible and adaptable material of the in-the-ear portion 27 is configured to have appropriate elasticity, flexibility, and adaptability such that all of the EEG sensor electrodes 12, 13, 72, 73, 82, 83, and the stimulating electrode 31 are naturally in close contact (provided by the elastic, flexible, and adaptable characteristics of the resilient material so that it can conform to the contours of the external ear canal 904 and snugly fill the interior of the external ear canal 904) with the skin of the external ear canal 904 of the wearer's ear 902 when the in-the-ear portion 27 is inserted into the external ear canal 904 of the wearer's ear 902 (FIG. 13). Attaching and removing all of the EEG sensor electrodes 12, 13, 72, 73, 82, 83, and the stimulating electrode 31 will be as easy as inserting and removing the in-the-ear portion 27 from the wearer's external ear canal 904.

Generally, an elastic flexible and adaptable material may be flexible to allow slight deformation and optionally resilient so as to return to its original shape after deformation. In preferred embodiments, all or portions of an earbud style structure 61 (e.g., a horizontal portion 25), all or portions of an in-the-ear structure 62, all or portions of a behind-the-ear structure 63 (e.g., in-the-ear portion 27), all or portions of the tubular-shaped structure 66 may be made from or comprise an elastic flexible and adaptable material such as natural and/or synthetic rubber material such as latex rubber, silicone foam, silicone rubber or polysiloxanes, rubber foam, urethane foam, plastic foam, neoprene foam, latex foam rubber, polyurethane foam rubber, forms of the organic compound isoprene, Polyacrylate Rubber, Ethylene-acrylate Rubber, Polyester Urethane, flexible plastics, such as high-density polyethylene (HDPE), polyvinyl chloride (PVC), polypropylene (PP), Polystyrene (PS), Polycarbonate (PC), low density polyethylene (LDPE), or any other flexible material including combinations of materials.

In some embodiments, the EEG recording housing 11 may house one or more components, such as a processing unit 50, an EEG recording module 20, EEG sensor electrodes 12, 13, 72, 73, 82, 83, a speaker 15, a power source 16, vibrator 17, etc., which may be communicatively coupled via a local interface 58. The local interface 58 can be, for example but not limited to, one or more buses, circuit boards, wiring harnesses, or other wired connections or wireless connections, as is known in the art. The local interface 58 can have additional elements, which are omitted for simplicity, such as controllers, buffers (caches), drivers, repeaters, and receivers, among many others, to enable communications. Further, the local interface 58 may include address, control, and/or data connections to enable appropriate communications among the aforementioned components.

In some embodiments, an auricular EEG monitoring system 100 may comprise a processing unit 50 which may be contained in the EEG recording housing 11. A processing unit 50 may include a processor 51 that may comprise a hardware device for executing software instructions. The processor 51 can be any custom made or commercially available processor, a central processing unit (CPU), an auxiliary processor among several processors associated with the processing unit 50, a semiconductor-based microprocessor (in the form of a microchip or chip set), or generally any device for executing software instructions. Optionally, when the processing unit 50 is in operation, the processor 51 may be configured to execute software stored within a memory 55, to communicate data to and from the memory 55, and to generally control one or more operations of the auricular EEG monitoring system 100 pursuant to the software instructions and/or from instructions. In an exemplary embodiment, the processor 51 may include a mobile optimized processor, such as optimized for power consumption and mobile applications.

In some embodiments, an auricular EEG monitoring system 100 may comprise one or more I/O interfaces 52 which can be used to provide user input and display system output data, such as operational status, from the auricular EEG monitoring system 100. The I/O interfaces 52 can include, for example, buttons, knobs, switches, LED indicator lights, LED display, LCD display, a serial port, a parallel port, a small computer system interface (SCSI), an infrared (IR) interface, a radio frequency (RF) interface, a universal serial bus (USB) interface, and the like.

In some embodiments, an auricular EEG monitoring system 100 may comprise a network interface 53 which may be contained in the EEG recording housing 11 and which may enable wired and/or wireless communication between one or more components, such as EEG recording module 20, processing unit 50, etc., with one or more client devices 400. Preferably, a network interface 53 may comprise a radio that may operate via WiFi and/or Bluetooth communication standards. In further embodiments, a network interface 53 may comprise a radio that may operate on a cellular band and may communicate with or receive a Subscriber Identity Module (SIM) card or other wireless network identifier. Any number of suitable wireless data communication protocols, techniques, or methodologies can be supported by a network interface 53, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Near-Field Communication (NFC); Frequency Hopping Spread Spectrum; Long Term Evolution (LTE); cellular/wireless/cordless telecommunication protocols (e.g. 3G/4G, etc.); wireless home network communication protocols; paging network protocols; magnetic induction; satellite data communication protocols; wireless hospital or health care facility network protocols such as those operating in the WMTS bands; GPRS; proprietary wireless data communication protocols such as variants of Wireless USB; and any other protocols for wireless communication. In further embodiments, a network interface 53 may enable wired network communication and may include, for example, an Ethernet card or adapter (e.g., 10BaseT, Fast Ethernet, Gigabit Ethernet, 10 GbE) or a wireless local area network (WLAN) card or adapter (e.g., 802.11a/b/g/n). The network interface 53 may include address, control, and/or data connections to enable appropriate communications on the network.

In some embodiments, a processing unit 50 may comprise a memory 55 that may include any of volatile memory elements (e.g., random access memory (RAM, such as DRAM, SRAM, SDRAM, etc.)), nonvolatile memory elements (e.g., ROM, hard drive, etc.), and combinations thereof. Moreover, the memory 55 may incorporate electronic, magnetic, optical, and/or other types of storage media. Note that the memory 55 may have a distributed architecture, where various components are situated remotely from one another, but can be accessed by the processor 51. Optionally, memory 55 can include one or more software programs, each of which includes an ordered listing of executable instructions for implementing logical functions. Optionally, the software in the memory system 55 includes a suitable operating system (O/S) 56 and program (s) 57. The operating system 56 essentially controls the execution of input/output interface 52 and other element functions, and provides scheduling, input-output control, file and data management, memory management, and communication control and related services. The operating system 56 may be, for example, LINUX (or another UNIX variant), Android (available from Google), Symbian OS, Microsoft Windows CE, Microsoft Windows 7 Mobile, iOS (available from Apple, Inc.), webOS (available from Hewlett Packard), Blackberry OS (Available from Research in Motion), and the like. The programs 57 may include various applications, add-ons, etc. configured to provide end user functionality of the device 100.

Further, many embodiments are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequences of actions described herein can be considered to be embodied entirely within any form of computer readable storage medium having stored therein a corresponding set of computer instructions that upon execution would cause an associated processor to perform the functionality described herein. Thus, the various aspects of the invention may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

The auricular EEG monitoring system 100 may comprise one or more auricular EEG recording modules 20. In some embodiments, an auricular EEG monitoring system 100 may comprise an auricular EEG recording module 20 that may be contained in an EEG recording housing 11. An auricular EEG recording module 20 may record the electrical activities of the brain (EEG signals) of the wearer 900 to generate EEG data. The EEG data may be analyzed by a processing unit 50, 401, to detect presence or cessation of EEG signals suggestive of neuropsychiatric disorders. The processing unit 50, 401 is further configured to analyze the EEG data to detect presence or cessation of EEG signals suggestive of impending neuropsychiatric disorders. These neuropsychiatric disorders include seizure, migraine, cluster headache, major depressive disorder, schizophrenia, bipolar disorder, etc.

Generally, amplifiers and filters 21 of an auricular EEG recording module 20 may pick up the electrical activities of the wearer's 900 brain via the plurality of EEG sensor electrodes 12, 13, 72, 73, 82, 83. An amplifier of amplifiers and filters 21 is responsible for amplifying the weak electrical signals received from the electrodes 12, 13, 72, 73, 82, 83. The brain's electrical signals are typically very faint, often in the 50 microvolts range. The amplifier boosts these signals to a level that can be accurately recorded and displayed. Modern EEG machines use sophisticated amplifiers that minimize noise and ensure signal clarity. Filters of amplifiers and filters 21 are used to remove unwanted noise and interference from the electrical signals. Common sources of noise include muscle contractions, electrical interference from other devices, and movement artifacts. EEG machines use various filters, such as high-pass, low-pass, and notch filters, to clean the signals, ensuring that the resulting EEG trace is clear and interpretable. An analog-to-digital converter (ADC) 22 may transform the analog electrical signals from the brain into digital data. This digital conversion is essential for processing, storing, and displaying the EEG data on a screen or print out. The ADC 22 ensures that the data is accurately digitized, preserving the integrity of the original signals. The ADC 22 may be in communication with a processing unit 50.

According to another embodiment consistent with the principles of the present invention, an automatic detection-remedy system 101 is disclosed (FIGS. 2, 3, 5-7, 11-13, and 18). In some embodiments, an automatic detection-remedy system 101 may comprise an auricular electroencephalo-gram (EEG) monitoring system 100 having one or more EEG recording modules 20, such as discussed above, that may be configured to record EEG data of the wearer 900. The automatic detection-remedy system 101 may include one or more transcutaneous auricular vagus nerve stimulation units (taVNS units) 30, such as a first taVNS unit 30 and a second taVNS unit 30, with each taVNS unit 30 having a stimulating electrode 31 configured to contact vagus innervated auricular skin of one of the wearer's ears 900. The vagus innervated auricular skin includes external ear canal 904, tragus 905, cymba-concha 906, cavum-concha 907 and small adjacent areas. The vagus innervated auricular skin that the stimulating electrode 31 is configured to contact may be selected from at least one of the following: external ear canal 904, tragus 905, cymba-concha 906, and cavum-concha 907. Preferably, an automatic detection-remedy system 101 may comprise a first taVNS unit 30, the first taVNS unit 30 having a first stimulating electrode 31 configured to contact vagus innervated auricular skin of the wearer's first ear 902. A processing unit 50, 401, may be in electronic communication with the auricular electroencephalogram (EEG) monitoring system 100 and with the one or more taVNS units 30. The processing unit 50, 401, may be configured to analyze EEG data recorded by the EEG monitoring system 100 to detect the presence or cessation of EEG signals suggestive of one or more neuropsychiatric disorders. When the presence of EEG signals suggestive of a neuropsychiatric disorder is detected by the processing unit 50, 401, the processing unit 50, 401, may be configured to immediately send signals to a taVNS unit 30 to cause the taVNS unit 30 to automatically start sending pre-determined electric stimuli to the vagus innervated auricular skin of the wearer's ear 902 to which the stimulating electrode 31 is in contact with. When cessation of EEG signals suggestive of the neuropsychiatric disorder is detected by the processing unit 50, 401, the processing unit 50, 401, may be further configured to immediately send signals to the taVNS unit 30 to cause the taVNS unit 30 to automatically stop sending pre-determined electric stimuli to the vagus innervated auricular skin of the wearer's ear 902 to which the stimulating electrode 31 is in contact with. The processing unit 50, 401, may be further configured to analyze the EEG data recorded by the EEG monitoring system 100 to detect the presence or cessation of EEG signals suggestive of one or more impending neuropsychiatric disorders. When the presence of EEG signals suggestive of an impending neuropsychiatric disorder is detected by the processing unit 50, 401, the processing unit 50, 401, may be configured to immediately send signals to a taVNS unit 30 to cause the taVNS unit 30 to automatically start sending pre-determined electric stimuli to the vagus innervated auricular skin of the wearer's ear 902 to which the stimulating electrode 31 is in contact with. When cessation of EEG signals suggestive of the impending neuropsychiatric disorder is detected by the processing unit 50, 401, the processing unit 50, 401, may be further configured to immediately send signals to the taVNS unit 30 to cause the taVNS unit 30 to automatically stop sending pre-determined electric stimuli to the vagus innervated auricular skin of the wearer's ear 902 to which the stimulating electrode 31 is in contact with.

An automatic detection-remedy system 101 may comprise one or more transcutaneous auricular vagus nerve stimulation (taVNS) units 30 ("taVNS unit 30") such as shown in FIG. 18. Preferably, an automatic detection-remedy system 101 may comprise a second taVNS unit 30, the second taVNS unit 30 having a second stimulating electrode 31 configured to contact vagus innervated auricular skin of the wearer's second ear 902. A processing unit 50, 401, may be in electronic communication with the second taVNS unit 30. When the presence of EEG signals suggestive of a neuropsychiatric disorder is detected by the processing unit 50, 401, the processing unit 50, 401, may be configured to immediately send signals to the second taVNS unit 30 to cause the second taVNS unit 30 to automatically start sending pre-determined electric stimuli to the vagus innervated auricular skin of the wearer's second ear 902 to which the second stimulating electrode 31 is in contact with. When cessation of EEG signals suggestive of the neuropsychiatric disorder is detected by the processing unit 50, 401, the processing unit 50, 401, may be further configured to immediately send signals to the second taVNS unit 30 to cause the second taVNS unit 30 to automatically stop sending pre-determined electric stimuli to the vagus innervated auricular skin of the wearer's second ear 902 to which the second stimulating electrode 31 is in contact with. When presence of EEG signals suggestive of an impending neuropsychiatric disorder is detected by the processing unit 50, 401, the processing unit 50, 401, may be further configured to immediately send signals to the second taVNS unit 30 to cause the second taVNS unit 30 to automatically start sending pre-determined electric stimuli to the vagus innervated auricular skin of the wearer's second ear 902 to which the second stimulating electrode 31 is in contact with. When cessation of EEG signals suggestive of the impending neuropsychiatric disorder is detected by the processing unit 50, 401, the processing unit 50, 401, may be further configured to immediately send signals to the second taVNS unit 30 to cause the second taVNS unit 30 to automatically stop sending pre-determined electric stimuli to the vagus innervated auricular skin of the wearer's second ear 902 to which the second stimulating electrode 31 is in contact with.

Each auricular EEG recording module 20 may be configured to record EEG data of the wearer 900 via plurality of EEG sensor electrodes 12, 13, 72, 73, 82, 83. The recorded EEG data may be transmitted or otherwise electronically communicated to a processing unit 50, 401. With the help of various EEG analysis algorithms (as known in the art), the processing unit 50, 401, may be configured to analyze the EEG data to detect presence or cessation of EEG signals suggestive of neuropsychiatric disorders. The processing unit 50, 401, may also be configured to analyze the EEG data to detect presence or cessation of EEG signals suggestive of impending neuropsychiatric disorders. These neuropsychiatric disorders include seizure, migraine, cluster headache, major depressive disorder, schizophrenia, bipolar disorder, etc.

In preferred embodiments, an automatic detection-remedy system 101 may comprise a novel integration of the auricular EEG monitoring system 100 and a transcutaneous auricular vagus nerve stimulation (taVNS) unit 30. The auricular EEG monitoring system 100 comprises one or more EEG recording modules 20. Each EEG recording module 20 preferably has a plurality of miniature EEG sensor electrodes 12, 13, 72, 73, 82, 83, that are configured to contact or be attached to separate areas selected from at least one of the following: the external ear canal 904, external ear 902, or peri-auricular area 903. The taVNS unit 30 preferably has a miniature stimulating electrode 31 that is configured to contact or be attached to vagus nerve innervated auricular skin of the wearer 900. The vagus innervated auricular skin includes external ear canal 904, tragus 905, cymba-concha 906, cavum-concha 907 and small adjacent areas. The vagus innervated auricular skin that the stimulating electrode 31 is configured to contact may be selected from at least one of the following: external ear canal 904, tragus 905, cymba-concha 906, and cavum-concha 907 of the wearer's ear 902. The EEG recording module 100 may be in electronic communication (e.g., through wire, Bluetooth, etc.) with a processing unit 50, 401. The taVNS unit 30 may also be in electronic communication with a processing unit 50, 401.

Figure 17:
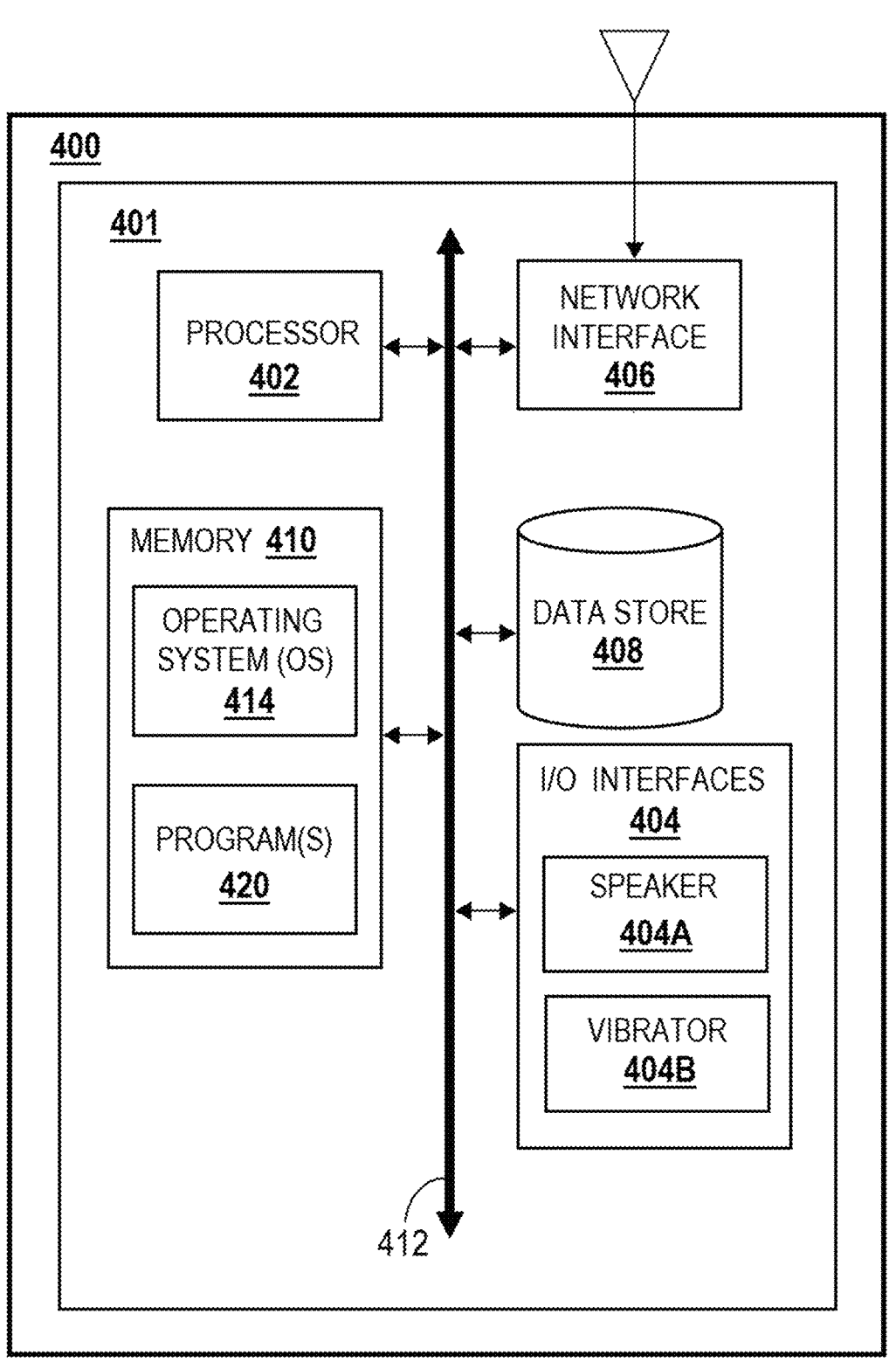
FIG. 17—FIG. 17 shows a block diagram illustrating some exemplary components of an example of a client device according to various embodiments described herein.

In some embodiments, an auricular EEG monitoring system 100 and/or an automatic detection-remedy system 101 may be in electronic communication with one or more client devices 400. In some embodiments, the auricular EEG monitoring system 100 may comprise one or more client devices 400. Referring to FIG. 17, in an exemplary embodiment, a block diagram illustrates a client device 400 of which may be a type of computing platform. A client device 400 can be a digital device that, in terms of hardware architecture, generally includes a processor 402, input/output (I/O) interfaces 404, a network interface 406, a data store 408, and memory 410. It may be appreciated by those of ordinary skill in the art that FIG. 17 depicts the client device 400 in an oversimplified manner, and a practical embodiment may include additional components and suitably configured processing logic to support known or conventional operating features that are not described in detail herein. The components (402, 404, 406, 408, and 410) are communicatively coupled via a local interface 412. The local interface 412 can be, for example but not limited to, one or more buses or other wired or wireless connections, as is known in the art. The local interface 412 can have additional elements, which are omitted for simplicity, such as controllers, buffers (caches), drivers, repeaters, and receivers, among many others, to enable communications.

The processor 402 is a hardware device for executing software instructions. The processor 402 can be any custom made or commercially available processor, a central processing unit (CPU), an auxiliary processor among several processors associated with the client device 400, a semiconductor-based microprocessor (in the form of a microchip or chip set), or generally any device for executing software instructions. When the client device 400 is in operation, the processor 402 is configured to execute software stored within the memory 410, to communicate data to and from the memory 410, and to generally control operations of the client device 400 pursuant to the software instructions. In an exemplary embodiment, the processor 402 may include a mobile optimized processor such as optimized for power consumption and mobile applications.

The I/O interfaces 404 can be used to receive data and user input and/or for providing system output. User input can be provided via a plurality of I/O interfaces 404, such as a keypad, a touch screen, speaker 404A, a camera, a microphone, a scroll ball, a scroll bar, buttons, barcode scanner, voice recognition, eye gesture, and the like. System output can be provided via a display screen such as a liquid crystal display (LCD), touch screen, and the like. The I/O interfaces 404 can also include, for example, a global positioning service (GPS) radio, a serial port, a parallel port, a small computer system interface (SCSI), an infrared (IR) interface, a radio frequency (RF) interface, a universal serial bus (USB) interface, and the like. The I/O interfaces 404 can include a graphical user interface (GUI) that enables a user to interact with the client device 400. Additionally, the I/O interfaces 404 may be used to output notifications to a user and can include a speaker 404A or other sound emitting device configured to emit audio notifications, a vibrational device or vibrator 404B configured to vibrate, shake, or produce any other series of rapid and repeated movements to produce haptic notifications, and/or a light emitting diode (LED) or other light emitting element which may be configured to illuminate to provide a visual notification.

The network interface 406 enables wireless communication to an external access device or network. Any number of suitable wireless data communication protocols, techniques, or methodologies can be supported by the network interface 406, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; Long Term Evolution (LTE); cellular/wireless/cordless telecommunication protocols (e.g. 3G/4G, etc.); wireless home network communication protocols; paging network protocols; magnetic induction; satellite data communication protocols; wireless hospital or health care facility network protocols such as those operating in the WMTS bands; GPRS; proprietary wireless data communication protocols such as variants of Wireless USB; and any other protocols for wireless communication.

The data store 408 may be used to store data and is therefore a type of memory. The data store 408 may include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 408 may incorporate electronic, magnetic, optical, and/or other types of storage media.

The memory 410 may include any of volatile memory elements (e.g., random access memory (RAM, such as DRAM, SRAM, SDRAM, etc.)), nonvolatile memory elements (e.g., ROM, hard drive, etc.), and combinations thereof. Moreover, the memory 410 may incorporate electronic, magnetic, optical, and/or other types of storage media. Note that the memory 410 may have a distributed architecture, where various components are situated remotely from one another, but can be accessed by the processor 402. The software in memory 410 can include one or more software programs 420, each of which includes an ordered listing of executable instructions for implementing logical functions. In the example of FIG. 17, the software in the memory system 410 includes a suitable operating system (O/S) 414 and programs 420.

The operating system 414 essentially controls the execution of other computer programs, and provides scheduling, input-output control, file and data management, memory management, and communication control and related services. The operating system 414 may be, for example, LINUX (or another UNIX variant), Android (available from Google), Symbian OS, Microsoft Windows CE, Microsoft Windows 7 Mobile, Microsoft Windows 10, iOS (available from Apple, Inc.), webOS (available from Hewlett Packard), Blackberry OS (Available from Research in Motion), and the like.

The programs 420 may include various applications, add-ons, etc. configured to provide end user functionality with the client device 400. For example, exemplary programs 420 may include, but not limited to, a web browser, social networking applications, streaming media applications, games, mapping and location applications, electronic mail applications, financial applications, and the like.

Figure 16:
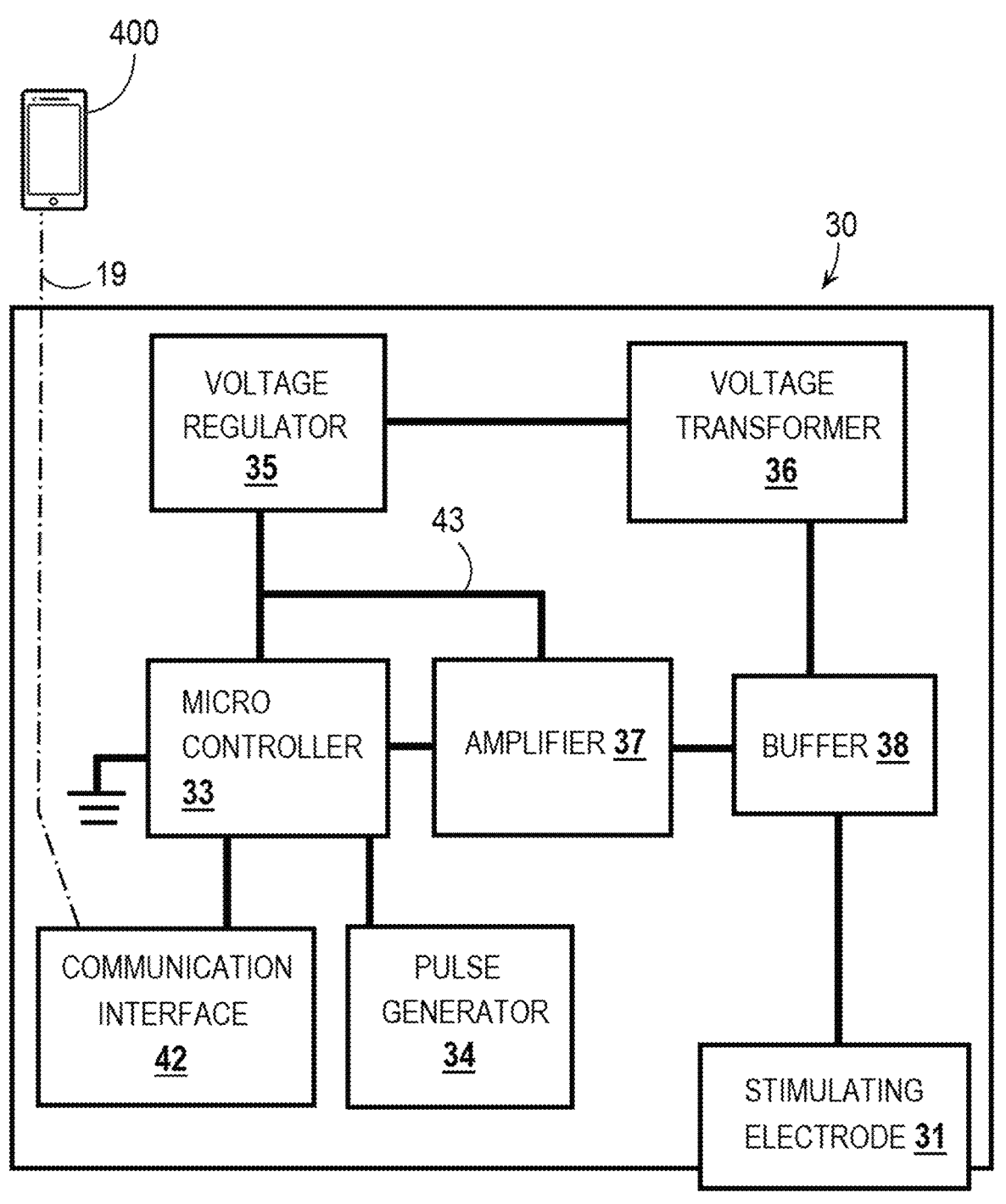
FIG. 16—FIG. 16 depicts a block diagram illustrating some exemplary components of an example of a transcutaneous auricular vagus nerve stimulation (taVNS) unit according to various embodiments described herein.

A taVNS unit 30 may comprise any device that is able to provide transcutaneous auricular vagus nerve stimulation to a user's body. As an example, and referring to FIG. 16, a taVNS unit 30 may comprise a microcontroller 33 that may be in communication with a pulse generator 34, voltage regulator 35, voltage transformer 36, amplifier 37, and buffer 38, and that may be configured to generate taVNS stimuli that may be transmitted to vagus nerve innervated auricular skin via a stimulating electrode 31.

Optionally, a taVNS unit 30 may comprise a communication interface 42 which may enable electronic communication 19 (e.g., wired and/or wireless communication) between the taVNS unit 30 and another electronic device, such as a client device 400, an auricular EEG monitoring system 100, etc. Preferably, a communication interface 42 may comprise a radio that may operate via WiFi and/or Bluetooth communication standards. In further embodiments, a communication interface 42 may be configured as a network interface 53 described above so that it may operate on any wireless and/or wired electronic communication 19 protocol that a network interface 53 may use.

One or more components (31, 33, 34, 35, 36, 37, 38, 42) of a taVNS unit 30 may be contained in a taVNS housing and may be in electronic communication via a local interface 43. A taVNS housing may be configured in any size and shape, and may be made from or comprise plastic, elastomer, silicone or any other material used in the field of personal medical devices. In some embodiments, a taVNS housing may be configured as an earbud-style structure 61 or as a behind-the-ear structure 63. Optionally, a taVNS housing may be coupled directly to an EEG recording housing 11 of an auricular EEG monitoring system 100 e.g., the taVNS housing and an EEG recording housing 11 may be integrally formed or molded together as a single unit. Optionally, a taVNS housing may be a standalone housing that may be remote from an EEG recording housing 11. In some embodiments, the taVNS unit 30 may include a stimulating electrode 31 which may be built within the taVNS housing of the taVNS unit 30 (so that the taVNS housing and stimulating electrode 31 may form a single unit). In further embodiments, a stimulating electrode 31 may be connected with the taVNS housing through a wire (so that the stimulating electrode 31 may be remote from the taVNS housing of the taVNS unit 30).

Figure 4:
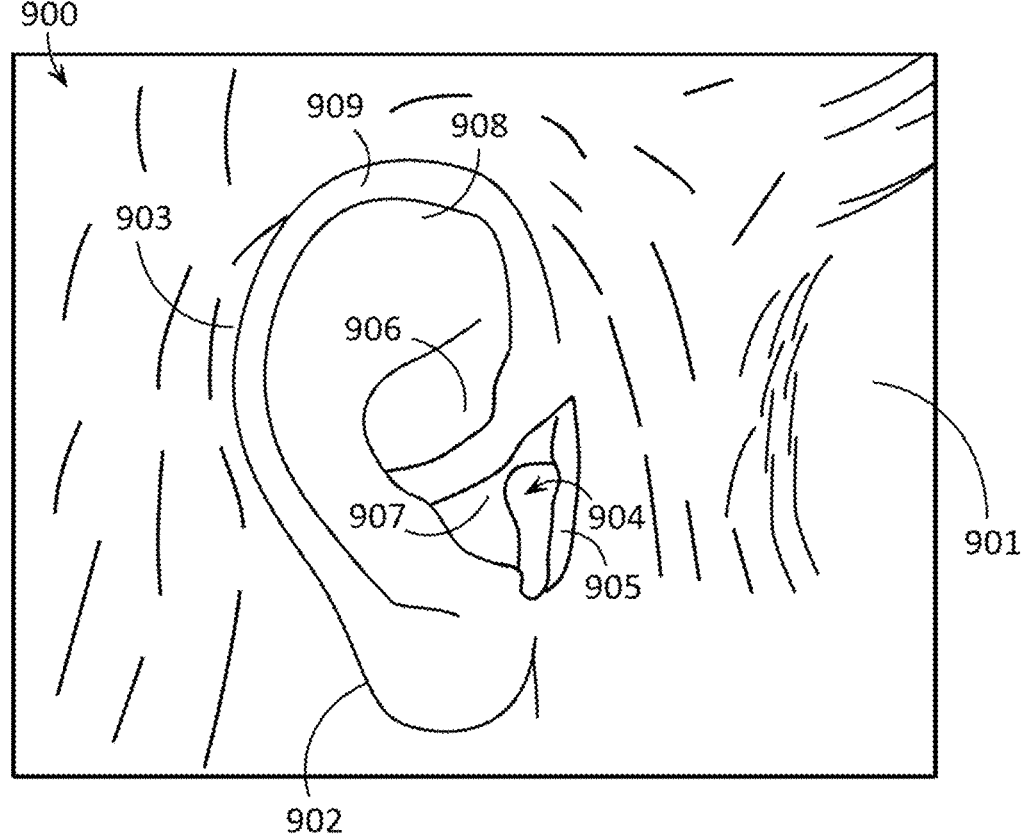
FIG. 4—FIG. 4 illustrates an elevation view of the anatomy of a human external ear, including the locations of tragus, cymba-concha, cavum-concha, triangular fossa, helix, lobule, external ear canal, etc.

The stimulating electrode 31 of an automatic detection-remedy system 101 may be attached to vagus nerve innervated auricular skin so that the stimuli output by the taVNS unit 30 may be transmitted to the vagus nerve innervated auricular skin via the stimulating electrode 31. Vagus innervated auricular skin includes external ear canal 904, tragus 905, cymba-concha 906, cavum-concha 907 and small adjacent areas, as shown in FIG. 4. Vagus nerve innervated auricular skin that the stimulating electrode 31 may be attached to may be selected from at least one of the following: tragus 905, cymba-concha 906, cavum-concha 907, and external ear canal 904. These areas are innervated by the auricular branch of the vagus nerve. Optionally, the taVNS unit 30 itself may also be attached to the tragus 905, cymba-concha 906, cavum-concha 907, or external ear canal 904. The tragus 905, concha region 906, 907, and external ear canal 904 are inherently stable for attachment of a taVNS unit 30 on a long-term basis.

When EEG signals suggestive of a neuropsychiatric disorder is detected, the processing unit 50, 401, may be configured to automatically send signals immediately to the one or more taVNS units 30 of the automatic detection-remedy system 101 to actuate the vagus nerve stimulation via stimulating electrode(s) 31, utilizing pre-determined stimulation parameters, such as shown in Table 1.

TABLE 1

| Example of taVNS unit 30 electric stimuli output parameters for neuropsychiatric disorders. | |
| --- | --- |
| Output | Parameter |
| Power supply | Direct current 3-9 volts |
| Pulse width | 0.05-1.0 milliseconds (ms) |
| Frequency | 0.5-200 Hz |
| Modes | Continuous wave or sparse-dense wave |
| Intensity | 0.1-15 milliamperes (mA) |

When the processing unit detects EEG signals suggestive of an impending neuropsychiatric disorder, the processing unit is also configured to automatically send signals to the taVNS unit immediately to actuate the vagus nerve stimulation, utilizing pre-determined stimulation parameters, such as shown in Table 2.

TABLE 2

| Example of taVNS unit 30 electric stimuli output parameters for impending neuropsychiatric disorders. | |
| --- | --- |
| Output | Parameter |
| Power supply | Direct current 3-9 volts |
| Pulse width | 0.05-0.9 milliseconds (ms) |
| Frequency | 0.5-150 Hz |
| Modes | Continuous wave or sparse-dense wave |
| Intensity | 0.1-10 milliamperes (mA) |

When a processing unit 50, 401, detects cessation of EEG signals suggestive of the neuropsychiatric disorder or cessation of EEG signals suggestive of the impending neuropsychiatric disorder, the processing unit 50, 401, may be configured to send signals to the taVNS unit 30 to automatically stop the vagus nerve stimulation. The settings or parameters for electric stimulation by the taVNS unit 30 are pre-determined to have the most effective parameter for each neuropsychiatric disorder. Similar or different stimulation parameters may be utilized for each neuropsychiatric disorder and for each impending neuropsychiatric disorder. (Tables 1-12). As disclosed herein, an automatic detection-remedy system 101 having the novel integration of an auricular EEG recording module 20 and a transcutaneous auricular vagus nerve stimulation (taVNS) unit 30 achieves very important dual functions, namely long-term EEG monitoring from the ear 902 and automatic instant therapeutic intervention by vagus nerve stimulation in response to specific EEG findings.

For most patients or wearers 900 with neuropsychiatric disorders, two auricular EEG recording modules 20, one coupled to each side of the external ear 902 or the peri-auricular area 903, will be preferred. In rare situations, only one auricular EEG recording module 20 may be enough if one-sided partial EEG can adequately detect a neuropsychiatric disorder. For most patients with neuropsychiatric disorders, two taVNS units 30 will be preferred, with one taVNS unit 30 coupled to each external ear 902 of the wearer 900. However, in rare situations when a patient cannot tolerate side effects from a taVNS unit 300 on one of the ears 902, a single taVNS unit 30 may be utilized in the other side/ear 902. This may be preferred if right-sided vagus nerve stimuli from taVNS unit 30 produces any bradycardia or other side effects. Bilateral vagal stimulation is usually more effective than unilateral vagal stimulation. However, vagal stimulation may be performed only on one side if the patient or wearer 900 responds well to one-sided stimulation.

In some embodiments, one or more components of an automatic detection-remedy system 100 may be housed in a hearing aid like or type of structure. The traditional hearing aids include in-the-ear type and behind-the-ear type and both types have close contact with the skin of concha 906, 907, tragus 905, external ear canal 904, and peri-auricular area 903. These areas are the optimal locations for attachment of the components of the present invention. (FIG. 4 shows anatomy of external ear.) Combining components of the present invention with a hearing aid will be a welcoming set-up for patients who already need hearing aids. For patients who do not need hearing aids, the earbud style structure 61, in-the-ear structures 62, or behind-the-ear structure 63 may be used for attachment of an automatic detection-remedy system 101 of the present invention. These locations and structures provide inherently secure and stable attachment. Another option for attachment for one or more components of an automatic detection-remedy system 101 is through ear-piercing studs or pins. For example, an ear-piercing stud or pin through the tragus 905 may be used for secure attachment of the automatic detection-remedy system 101.

Figure 6:
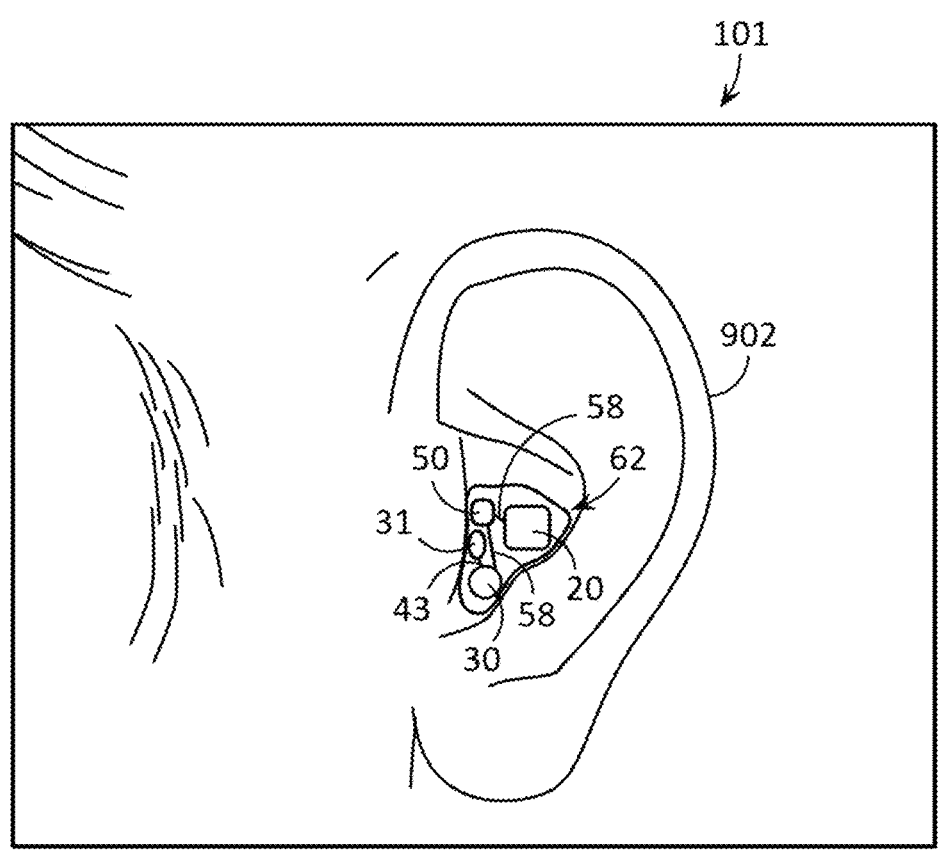
FIG. 6—FIG. 6 depicts a diagram of yet a further example of an automatic detection-remedy system according to various embodiments described herein.

In some embodiments, a processing unit 50 can be incorporated within an EEG recording housing 11 of the automatic detection-remedy system 101 and housed in a behind-the-ear structure 63 or in-the-ear structure 62 (in-the-ear hearing aid style shown in FIGS. 6, 12). If the processing unit 50 housed at a location very close to the auricular EEG recording module 20 and taVNS unit 30, they can be connected through wire type local interface 58, instead of through wireless communication. For example, if the processing unit 50 is housed within a behind-the-ear structure 63, the processing unit 50 can be connected with the EEG recording module 20 and the ta VNS 30 through wire type local interfaces 58. Alternatively, the processing unit 401 may be a component of a smart phone type of client device 400 or a health tracker with an app. The processing unit 50,

401, may also be an independent processing device, which is wearable or portable or handheld.

Figure 7:
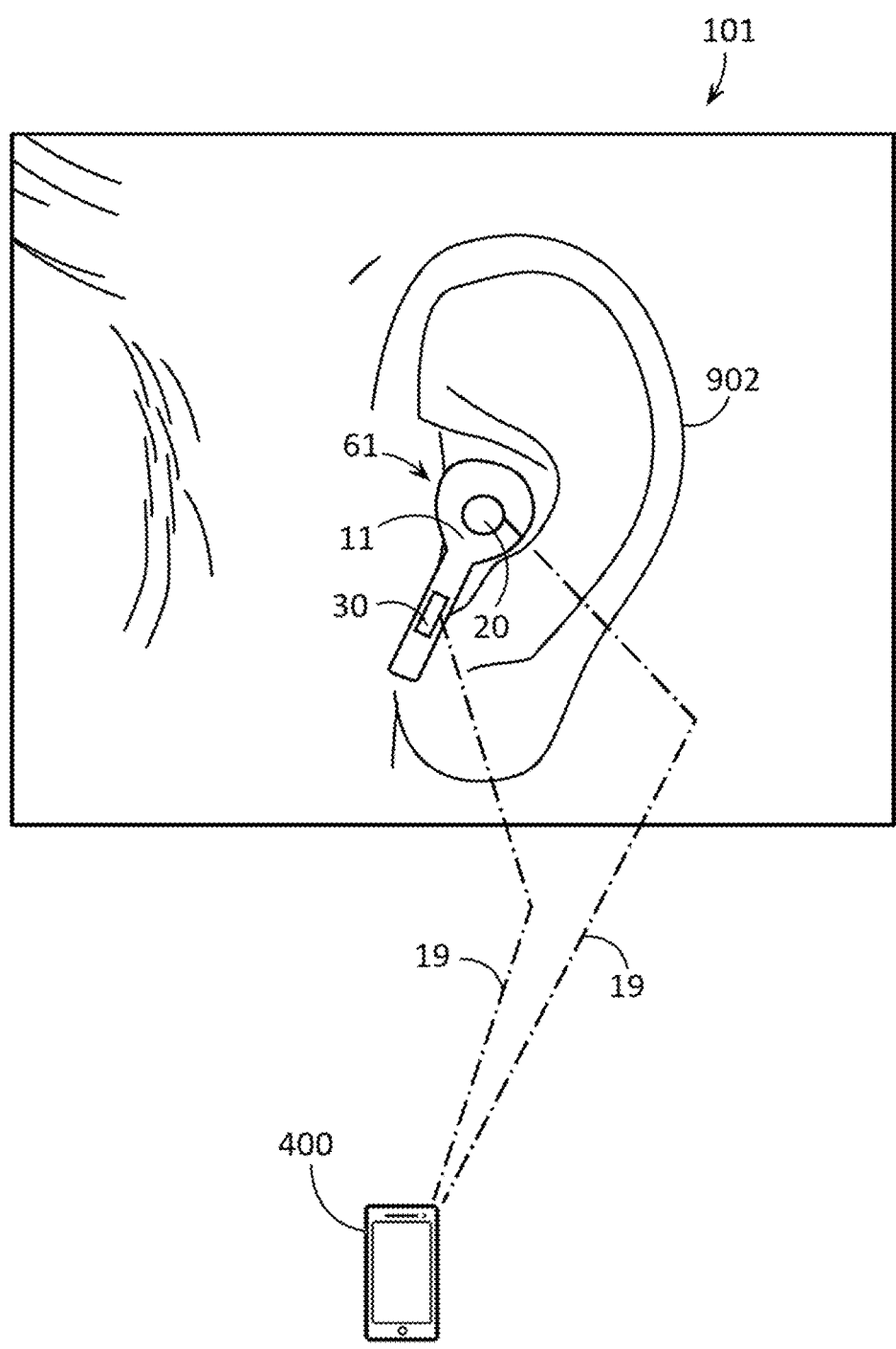
FIG. 7—FIG. 7 illustrates a diagram of yet another further example of an automatic detection-remedy system according to various embodiments described herein.

As aforementioned, in some embodiments of an automatic detection-remedy system 101, a taVNS unit 30, an auricular EEG recording module 20, and a processing unit 50 may be housed in an in-the-ear structure 62 (structure similar to an in-the ear hearing aid) or a behind-the-ear structure 63 (structure similar to a behind-the-ear hearing aid). In further embodiments, a taVNS unit 30, an auricular EEG recording module 20, and a processing unit 50 may be housed in an earbud style structure 61 (such as earphone, earbud or air-pod structures), as earbud style structures 61 are inherently stable for secure attachment. They can be easily removed temporarily for power source 16 (battery) re-charging and can be put back in place easily. Nowadays, earphones, air-pods and earbuds have become quite popular. They are nice-looking and well accepted by most people. (FIGS. 2, 7, and 11). These housing structures enable easy and convenient long-term monitoring and automatic therapeutic intervention of the brain functions and various neuropsychiatric disorders.

In preferred embodiments, the automatic detection-remedy system 101 may comprise an earbud style structure 61 having an EEG recording module 20 housed in the EEG recording housing 11 that is configured as an earbud style structure 61. A taVNS unit 30 may be housed in a taVNS housing that may be coupled to or integrally formed with the EEG recording housing 11 that is configured as an earbud style structure 61. All of the EEG sensor electrodes 12, 13, 72, 73, 82, 83, and the taVNS stimulating electrode 31 may be placed on the surface of the horizontal portion 25 of the earbud style structure 61. Preferably, the horizontal portion 25 of the earbud style structure 61 may be made with or may comprise an elastic flexible and adaptable material (such as silicone), in which the material for the earbud style structure 61 is configured to have appropriate elasticity, flexibility and adaptability such that when the horizontal portion 25 of the earbud-style structure 61 is inserted into a wearer's external ear canal 904, the horizontal portion 25 of the earbud style structure 61 will naturally adapt to the contour of wearer's external ear canal 904 and will snugly fill the interior of the wearer's external ear canal 904. This set-up and the elasticity, flexibility and adaptability of the material will allow all of these electrodes 12, 13, 72, 73, 82, 83, 31, to be naturally in close contact with the skin of the wearer's external ear canal 904 (FIG. 11). At the same time, the taVNS stimulating electrode 31 will also be naturally in close contact with vagus innervated auricular skin since external ear canal 904 is part of vagus innervated auricular skin. For the wearer 900, attaching and removing these electrodes 12, 13, 72, 73, 82, 83, 31, will be as easy as inserting and removing the earbud-style structure 61 from the wearer's external ear canal 904. There will be no need for a certified technologist to apply the electrodes. Applying adhesive material to secure these electrodes 12, 13, 72, 73, 82, 83, 31, will also be unnecessary. This is feasible due to the unique anatomical features of the human external ear canal 904, as illustrated in FIGS. 4, 7, and 11. This will create huge convenience for the wearer.

These advantages can be similarly achieved when the automatic detection-remedy system 101 comprises a behind-the-ear structure 63 for a housing (a housing similar to a behind-the-ear-hearing-aid-style structure). For example, the automatic detection-remedy system 101 may comprise a behind-the-ear structure 63 having an EEG recording module 20 housed in the EEG recording housing 11 that is configured as a behind-the-ear structure 63 (a behind-theear-hearing-aid-style structure). A taVNS unit 30 may be housed in a taVNS housing that may be coupled to or integrally formed with the EEG recording housing 11 that is configured as a behind-the-ear structure 63. The EEG recording module 20 may be housed in an EEG recording housing 11. The in-the-ear portion 27 may be made with elastic flexible and adaptable material (such as silicone), in which the material for the in-the-ear portion 27 is configured to have appropriate elasticity, flexibility and adaptability so that the in-the-ear portion 27 will naturally adapt to the contour of the wearer's external ear canal 904 and will also naturally fill the interior of the wearer's external ear canal 904 when it is inserted into the wearer's external ear canal 904. All of the EEG sensor electrodes 12, 13, 72, 73, 82, 83, may be placed on the surface of the in-the-ear portion 27 so that all of these electrodes 12, 13, 72, 73, 82, 83, may be naturally in close contact with the skin of the wearer's external ear canal 904 when the in-the-ear portion 27 is inserted into the wearer's external ear canal 904. The taVNS stimulating electrode 31 may also be placed on the surface of the in-the-ear portion 27 such that when the in-the-ear portion is inserted into the wearer's external ear canal 904, the stimulating electrode 31 will also be naturally in close contact with the skin of the wearer's external ear canal 904. At the same time, the taVNS stimulating electrode 31 will also be naturally in close contact with vagus innervated auricular skin since external ear canal 904 is part of vagus innervated auricular skin. For a wearer 900, attaching and removing these electrodes 12, 13, 72, 73, 82, 83, 31, will be as easy as inserting and removing the in-the-ear portion 26 from the wearer's external ear canal 904. There will be no need for a certified technologist to apply the electrodes 12, 13, 72, 73, 82, 83, 31. Applying adhesive material to secure these electrodes 12, 13, 72, 73, 82, 83, 31, will also be unneeded.

The aforementioned advantages can also be similarly achieved when an EEG recording housing 11 of an auricular EEG monitoring system 100 and/or an automatic detection-remedy system 101 may be shaped or configured as a tubular-shaped structure 66 and all of the EEG sensor electrodes 12, 13, 72, 73, 82, 83 and the stimulating electrode 31 are configured to be located at the surface 91 of the tubular-shaped structure 66. Preferably, the tubular-shaped structure 66 may be made with or may comprise elastic flexible and adaptable material (such as silicone), in which the material for the tubular-shaped structure 66 is configured to have appropriate elasticity flexibility and adaptability such that when the tubular-shaped structure 66 is inserted into a wearer's external ear canal 904, the tubular-shaped structure 66 will naturally adapt to the contour of wearer's external ear canal 904 and will snugly fill the interior of the wearer's external ear canal 904. This set-up and the elasticity flexibility and adaptability of the material will enable all of these electrodes 12, 13, 72, 73, 82, 83, 31 to be naturally in close contact with the skin of the wearer's external ear canal 904. The taVNS stimulating electrode 31 will also be naturally in close contact with the wearer's vagus innervated auricular skin since the skin of the external ear canal 904 is part of the vagus innervated auricular skin.

In some embodiments, a separate client device 400 may be used for housing of one or more of the components of an automatic detection-remedy system 101. For example, an EEG recording module 20 and the processing unit 401 may be housed remotely in a wearable client device 400, such as a smart watch-type structure. The EEG sensor electrodes 12, 13, 72, 73, 82, 83, and the taVNS unit 30 may be housed in either an earbud-type housing (earbud style structure 61) or an in-the-ear portion 27 of a behind-the-ear-hearing-aid-style housing (behind-the-ear structure 63). Wireless EEG sensor electrodes may be used for all of the EEG sensor electrodes 12, 13, 72, 73, 82, 83. (Wireless dry electrodes for in-ear EEG such as that described by Ryan Kaveh et al. in Nature Communications on Aug. 2, 2024. Wireless dry EEG electrodes are also available from Zeto, Inc. headquarter in Santa Clara, California.) There are well-known wired or wireless EEG amplifiers available, such as EEG Electroencephalogram Smart Amplifier (Part #: EEG100D), or preferably BioNomadix 2Ch Wireless EEG Amplifier (Part #: BN-EEG2), both being made by the same company BIOPAC Systems, Inc. (Goleta, California). By using wireless EEG electrodes and wireless EEG amplifier, the EEG recording module 20, together with the processing unit 401, may be housed remotely in a wearable client device 400 (such as a watch-type client device) and communicate wirelessly with all of the EEG sensor electrodes 12, 13, 72, 73, 82, 83.

There are many neuropsychiatric disorders that can be detected by EEG and which respond to modulating therapy with vagal nerve stimulation, including seizures, migraine, cluster headache, major depressive disorder, bipolar disorder, etc. While the automatic detection-remedy system 101 may be used to treat neuropsychiatric disorders which include seizure, migraine, cluster headache, major depressive disorder and bipolar disorder, the automatic detection-remedy system 101 may be used to treat other neuropsychiatric disorders.

In some embodiments, an auricular EEG monitoring system 100 and/or an automatic detection-remedy system 101 may comprise a speaker 15, 404A, and/or a vibrator 17, 404B, which may be configured to generate an audible and/or tactile notification to a wearer 900, or the wearer's healthcare provider 950, or other individual.

A speaker 15, 404A, may comprise a sound emitting device which can provide audible notification function. A speaker of a speaker 15, 404A, may comprise a buzzer, a piezoelectric sound producing device, a dielectric elastomer sound producing device, a buzzer, a moving coil loudspeaker, an electrostatic loudspeaker, an isodynamic loudspeaker, a piezo-electric loudspeaker, or any other device capable of producing one or more sounds.

In preferred embodiments, an auricular EEG monitoring system 100 and/or an automatic detection-remedy system 101 may comprise a speaker 15, 404A, that may be in electronic communication with a network interface 53, 406, and/or a processing unit 50, 401. The speaker 15, 404A, may be configured to generate an audible notification when the processing unit 50, 401, detects one or more of: the presence of EEG signals of the wearer 900 suggestive of a neuropsychiatric disorder; the presence of EEG signals of the wearer 900 suggestive of an impending neuropsychiatric disorder, the cessation of EEG signals of the wearer 900 suggestive of the neuropsychiatric disorder; and the cessation of EEG signals of the wearer 900 suggestive of the impending neuropsychiatric disorder.

A vibrator 17, 404B, may comprise a weight that may be rapidly moved by a long life brushless (BLDC) vibration motor, a coin or pancake vibration motor, an encapsulated vibration motor, an enclosed vibration motor, a pager motor, an eccentric rotating mass (ERM) motor, a linear resonant actuator (LRA), a printed circuit board (PCB) mounted vibration motor, or any other electrical device capable of producing a series of rapid and repeated movements.

In preferred embodiments, an auricular EEG monitoring system 100 and/or an automatic detection-remedy system

101 may comprise a vibrator 17, 404B, that may be in electronic communication with a network interface 53, 406, and/or a processing unit 50, 401. The vibrator 17, 404B, may be configured to generate a tactile notification when the processing unit 50, 401, detects one or more of: the presence of EEG signals of the wearer 900 suggestive of a neuropsychiatric disorder; the presence of EEG signals of the wearer 900 suggestive of an impending neuropsychiatric disorder, the cessation of EEG signals of the wearer 900 suggestive of the neuropsychiatric disorder; and the cessation of EEG signals of the wearer 900 suggestive of the impending neuropsychiatric disorder.

As perhaps best shown by FIG. 18, an illustrative example of some of the physical components which may be used with an auricular EEG monitoring system 100 and/or an automatic detection-remedy system 101, according to some embodiments are presented. An auricular EEG monitoring system 100 and an automatic detection-remedy system 101 may be configured to facilitate the transfer of data and information between one or more access points 103, client devices 400, and servers 300 over a data network 105. Client devices 400 and servers 300 may send data to and receive data from the data network 105 through a network connection 104 with an access point 103. A data store 308 accessible by the server 300 may contain one or more databases. The data may comprise any data recorded and generated by an auricular EEG monitoring system 100 and/or an automatic detection-remedy system 101.

In this example, an auricular EEG monitoring system 100 and/or an automatic detection-remedy system 101 may comprise or be in communication with at least one client device 400 (but preferably more than two client devices 400) configured to be operated by one or more users 900, 950. Client devices 400 may include mobile devices, such as laptops, tablet computers, personal digital assistants, smart phones, smart watches, and the like, that are equipped with a wireless network interface 406 capable of sending data to one or more servers 300 with access to one or more data stores 308 over a network 105, such as a wireless local area network (WLAN). Additionally, client devices 400 may include fixed devices, such as desktops, workstations, and the like, that are equipped with a wireless or wired network interface capable of sending data to one or more servers 300 with access to one or more data stores 308 over a wireless or wired local area network 105. The present invention may be implemented on at least one computing device, such as a client device 400 and/or server 300, programmed to perform one or more of the steps described herein. In some embodiments, more than one client device 400 and/or server 300 may be used, with each being programmed to carry out one or more steps of a method or process described herein.

A First Preferred Embodiment

In preferred embodiments, an automatic detection-remedy system 101 may comprise an auricular EEG monitoring system 100 having an auricular electroencephalogram (EEG) recording module 20, a transcutaneous auricular vagus nerve stimulation (taVNS) unit 30 and a processing unit 50, 401. The auricular EEG recording module 20 may have a plurality (at least two, but preferably more than two) of miniature EEG sensor electrodes 12, 13, 72, 73, 82, 83. The EEG sensor electrodes 12, 13, 72, 73, 82, 83, may be configured to contact separate areas selected from at least one of the following: external ear canal 904 of a first ear, external ear 902 of the first ear or peri-auricular area 903 around the first ear. The peri-auricular area 903 refers to the portion of the head around the auricle (pinna). The peri-auricular area 903 is typically hairless. The peri-auricular area includes a portion of the head in front of the auricle (pre-auricular area) and a portion of the head above and behind the auricle (post-auricular area). The pre-auricular area is small, about one inch wide and two inches long and curved along the anterior edge of the auricle. The post-auricular area is also small and is about one inch wide and about three inches long and curved along the superior and posterior edges of the auricle (pinna). The post-auricular area is where a behind-the-ear hearing aid is usually attached to. The pre-auricular area and the post-auricular area together is called "peri-auricular area" herein. (Anterior, posterior, superior, in front of and behind etc. all refer to the directions relative to the wearer's head when the wearer is in an upright position.) The EEG recording module 20 may be configured to record and generate EEG data of the wearer 900 using electrical activities of the wearer 900 that are picked up via all of the EEG sensor electrodes 12, 13, 72, 73, 82, 83. (FIGS. 1, 8-10). The taVNS unit 30 may comprise a miniature stimulating electrode 31. The stimulating electrode 31 may be configured to contact vagus innervated auricular skin of the wearer's 900 first ear. The vagus innervated auricular skin that the stimulating electrode 31 is configured to contact may be selected from at least one of the following: external ear canal 904, tragus 905, cymba-concha 906, and cavum-concha 907 of the wearer's first ear 902. (FIGS. 2, 11-13). The taVNS unit 30 may be configured to give electric stimuli through the stimulating electrode 31 to the vagus innervated auricular skin in a way similar to transcutaneous electric nerve stimulation (TENS) (taVNS and TENS as known in the art).

The auricular EEG recording module 20 may be in electronic communication with the processing unit 50, 401, through Bluetooth, wire or other electronic connection means or methods. The taVNS unit 30 may also be in electronic communication with the processing unit 50, 401, through Bluetooth, wire or other connection means. The EEG recording module 20 collects the wearer's EEG data and these data are transmitted to the processing unit 50, 401. With the help of various EEG analysis algorithms (as known in the art), the processing unit 50, 401, is configured to analyze the EEG data to detect presence of EEG signals of wearer 900 suggestive of neuropsychiatric disorders or impending neuropsychiatric disorders. The processing unit 50, 401, may also be configured to detect cessation of EEG signals of wearer 900 suggestive of the neuropsychiatric disorder or cessation of EEG signals suggestive of the impending neuropsychiatric disorder. Said neuropsychiatric disorders include seizure, migraine, cluster headache, major depressive disorder, and bipolar disorder.

When EEG signals suggestive of a neuropsychiatric disorder are detected by the processing unit 50, 401, the processing unit 50, 401, may be configured to automatically send signals to the taVNS unit 30 to actuate the taVNS unit 30 to send pre-determined electric stimuli immediately to the auricular branch of vagus nerve. The parameters of the electric stimuli, including the stimulating patterns, strength, duration, frequency and intervals, are pre-determined, such as shown in Table 1.

When the processing unit 50, 401, detects EEG signals suggestive of an impending neuropsychiatric disorder, the processing unit 50, 401, may also be configured to automatically send signals to the taVNS unit 30 to actuate the taVNS unit 30 to send pre-determined electric stimuli immediately to the auricular branch of vagus nerve via the stimulating electrode 31, such as shown in Table 2.

When the processing unit 50, 401, detects cessation of EEG signals suggestive of the neuropsychiatric disorder or cessation of EEG signals suggestive of the impending neuropsychiatric disorder, the processing unit 50, 401, is further configured to automatically send signals to the taVNS unit 30 to stop the electric stimuli to the vagus nerve. The settings or parameters of the electric stimuli, including the stimulating patterns, strength, duration, frequency and intervals, are pre-determined for different neuropsychiatric conditions. Each neuropsychiatric condition may respond to different parameters of the electric stimuli. Stimulus parameters were mentioned by various articles in the Background section of this invention. Examples of the stimulation parameters are listed in Tables 1 and 2.

For most patients with neuropsychiatric disorders, two auricular EEG recording modules 20, one on each side of the head 901 coupled to each external ears 902 or each peri-auricular area 903, will be preferred. In rare situations, only one auricular EEG recording module 20 might be enough for patients if their neuropsychiatric disorder can be adequately detected by a partial EEG on one side. For most patients with neuropsychiatric disorders, two taVNS units 30 will be preferred, with one taVNS unit 30 on each side of the head 901 coupled to an external ear 902 or external ear canal 904. In rare situations if the patient is unable to tolerate a taVNS unit 30 in one ear due to bradycardia or other side effects, only one taVNS unit 30 will be utilized and be placed in the other ear.

The auricular EEG recording module 20, the taVNS unit 30 and the processing unit 50, 401, can be housed together as a single structure and placed in the external ear canal 904, tragus 905, concha 906, 907, and/or peri-auricular area 903. Alternatively, the taVNS unit 30 and the EEG recording module 20 may be in separate structures and can be located adjacent to each other with both of them attached to the external ear canal 904, tragus 905, concha 906, 907, and/or peri-auricular area 903. Optionally, the taVNS housing may contain the taVNS unit 30 with its stimulating electrode 31. The stimulating electrode 31 may be incorporated inside the taVNS unit 30 itself or may be a separated element and connected with the taVNS unit 30 through a wire or local interface 43.

Preferably, the automatic detection-remedy system 101 further comprises a network interface 53, 406, in electronic communication with the processing unit 50, 401. The network interface 53, 406, may be configured to generate a notification (such as an audible notification via a speaker 15, 404A, or a tactile notification via a vibrator 17, 404B). When a neuropsychiatric disorder or an impending neuropsychiatric disorder is detected, the network interface 53, 406, may be configured to automatically generate a notification to a client device 400, such as to the client device 400 of the wearer 900 and/or the client device 400 of the wearer's healthcare provider 950 so that the wearer 900 or the wearer's healthcare provider 950 can take appropriate actions. Besides that, the taVNS unit 30 may be automatically actuated to start giving pre-determined electric stimuli to the vagus nerve. Thus, when a neuropsychiatric disorder or impending neuropsychiatric disorder is detected, in addition to receiving auricular vagus nerve stimulation automatically, the wearer 900 can take extra dose of medications or take other actions to alleviate the condition. An example of the notification device of a client device 400 is a speaker 404A, configured to generate audible warning notification when presence of a neuropsychiatric disorder or impending neuropsychiatric disorder is detected by the processing unit 50, 401. The notification function is well-known. Most smart watches and most health trackers have notification function.

In some embodiments, the auricular EEG recording module 20, the processing unit 50, 401, the taVNS unit 30 and the network interface 53 may be configured to be housed in one of the following structures: an earbud-style structure 61 or a behind-the-ear structure 63. The earbud-style structure 61 may be made with or may comprise elastic flexible and adaptable material. For the earbud-style structure 61, all of the EEG sensor electrodes 12, 13, 72, 73, 82, 83, and the stimulating electrode 31 for the taVNS unit 30 may be configured to be located on the surface of the horizontal portion 25 of the earbud-style structure 61. The material of the earbud-style structure 61 is configured to have appropriate elasticity, flexibility and adaptability such that when the earbud-style structure 61 is inserted into a wearer's external ear canal 904, all of the EEG sensor electrodes 12, 13, 72, 73, 82, 83, will be naturally in close contact with the skin of the wearer's external ear canal 904. Similarly, when the earbud-style structure 61 is inserted into the wearer's external ear canal 904, the taVNS stimulating electrode 31 will be naturally in close contact with the skin of the wearer's external ear canal 904 and also in close contact with the vagus innervated auricular skin since the external ear canal 904 is part of the vagus innervated auricular skin. This set-up will allow the wearer 900 to attach or to remove all of the EEG sensor electrodes 12, 13, 72, 73, 82, 83, and the stimulating electrodes 31 as easily as inserting or removing the earbud-style structure 61 into (or from) the wearer's 900 external ear canal 904. For the behind-the-ear structure 63, the in-the-ear portion 27 may be made with elastic flexible and adaptable material. All of the EEG sensor electrodes 12, 13, 72, 73, 82, 83, and the stimulating electrode 31 of the taVNS unit 30 may be located on the surface of the in-the-ear portion 27 as shown in FIG. 13. The material of the in-the-ear portion 27 is configured to have appropriate elasticity, flexibility and adaptability such that when the in-the-ear portion 27 is inserted into a wearer's external ear canal 904, all of these electrodes 12, 13, 72, 73, 82, 83, 31, will be naturally in close contact with the skin of the wearer's external ear canal 904 and the taVNS stimulating electrode 31 will be naturally in close contact with vagus innervated auricular skin. This set-up will allow the wearer 900 to attach or to remove all of the electrodes 12, 13, 72, 73, 82, 83, 31 as easily as inserting or removing the in-the-ear portion 27 into (or from) the wearer's 900 external ear canal 904.

In some embodiments, an EEG recording housing 11 of an auricular EEG monitoring system 100 and/or an automatic detection-remedy system 101 may be shaped or configured as a tubular-shaped structure 66 and all of the EEG sensor electrodes 12, 13, 72, 73, 82, 83 and the stimulating electrode 31 are configured to be located at the surface 91 of the tubular-shaped structure 66 and so that all of the EEG sensor electrodes 12, 13, 72, 73, 82, 83 and the stimulating electrode 31 are housed in the tubular-shaped structure 66. In preferred embodiments, one or more of the EEG sensor electrodes 12, 13, 72, 73, 82, 83, is/are configured to be located at the upper surface 91 (upper surface at approximately 90 degrees above horizontal level 92, as shown by electrodes 12, 13, in FIGS. 19, 22, 25) of the tubular-shaped structure 66. In preferred embodiments, one or more of the EEG sensor electrodes 12, 13, 72, 73, 82, 83, is/are configured to be located at between 0 and 90 degrees, and more preferably at approximately 45 degrees (plus or minus fifteen degrees) above the horizontal level 92 of the tubular structure 66 and is/are configured to face forward-upward direction 93 (e.g., as shown by electrodes 72, 82, in FIGS. 19, 21, 24). In preferred embodiments, one or more of the EEG sensor electrodes is/are configured to be located at between 90 and 180 degrees, and more preferably at approximately 135 degrees (plus or minus fifteen degrees) above the horizontal level 92 of the tubular structure 66 and is/are configured to face backward-upward direction 94 (e.g., as shown by electrodes 73, 83, in FIGS. 19, 23, 26) (Upper surface, horizontal level, forward, backward, and upward all refer to directions relative to the head 901 of the wearer 900 with the wearer in an upright position after the tubular-shaped structure 66 has been inserted into a wearer's external ear canal 904.) The tubular-shaped structure 66 is configured to be made of elastic flexible and adaptable material. The material of the tubular-shaped structure 66 is configured to have appropriate elasticity, flexibility and adaptability such that when the tubular-shaped structure 66 is inserted into a wearer's external ear canal 904, all of the EEG sensor electrodes 12, 13, 72, 73, 82, 83, and taVNS unit 30 stimulating electrode 31 will be naturally in close contact with the skin of the wearer's external ear canal 904. The taVNS stimulating electrode 31 will be naturally in close contact with vagus innervated auricular skin since external ear canal 904 is innervated by the auricular branch of the vagus nerve. This set-up will allow the wearer 900 to attach or to remove all of the EEG sensor electrodes 12, 13, 72, 73, 82, 83, and the stimulating electrodes 31 as easily as inserting or removing the tubular-shaped structure 66 into (or from) the wearer's 900 external ear canal 904.

Alternatively, a separate client device 400 may be used for housing of some of the components of the automatic detection-remedy system 101. For example, the EEG recording module 20 and the processing unit 50, 401, may be housed in a wearable client device 400, such as a watch-type structure. All of the EEG sensor electrodes 12, 13, 72, 73, 82, 83, and the taVNS unit 30 may be housed in either an earbud style structure 61 and/or an in-the-ear portion 27 of a behind-the-ear hearing-aid-style structure 63. Wireless EEG sensor electrodes may be used for all of the EEG sensor electrodes 12, 13, 72, 73, 82, 83. (Wireless dry EEG electrodes such as that described by Ryan Kaveh et al. in Nature Communications on Aug. 2, 2024. Wireless dry EEG electrodes are also available from Zeto, Inc. headquarter in Santa Clara, California.) There are well-known wired or wireless EEG amplifiers available, such as EEG Electroencephalogram Smart Amplifier (Part #: EEG100D), or preferably BioNomadix 2Ch Wireless EEG Amplifier (Part #: BN-EEG2), both being made by the same company BIOPAC Systems, Inc. (Goleta, California). By using wireless EEG sensor electrodes and wireless EEG amplifier, the EEG recording module 20 together with the processing unit 50, 401, may be housed in a watch-type client device 400 and communicate with all of the EEG sensor electrodes 12, 13, 72, 73, 82, 83, wirelessly.

There are many conventional smart watches or health trackers that contain monitoring devices 71 to monitor various body functions, including electrocardiogram (ECG), heart rate, blood oxygen, sleep, body temperature, and motion etc. (as known in the art). However, none of them can monitor the most important part of the human body, which is the brain. This automatic detection-remedy system 101 can easily combine with other monitoring devices 71 by placing their monitoring sensors in the external ear 902 or the external ear canal 904. Thus, this combined system 101 can monitor not only the brain (through EEG), it can also monitor other body functions, such as ECG, heart rate, blood oxygen, motion, sleep and body temperature, etc.

A Second Preferred Embodiment

In preferred embodiments, an automatic detection-remedy system 101 may be configured as an automatic auricular anti-seizure system, comprising an auricular electroencephalogram (EEG) recording module 20, a transcutaneous auricular vagus nerve stimulation (taVNS) unit 30 and a processing unit 50, 401. The auricular EEG recording module 20 may comprise a plurality of miniature EEG sensor electrodes 12, 13, 72, 73, 82, 83, configured to contact separate areas selected from at least one of the following: the external ear canal 904 of the wearer's first ear, external ear 902 of the wearer's first ear, or peri-auricular area 903 around the wearer's first ear. The EEG recording module 20 may be configured to record EEG of the wearer 900. The taVNS unit 30 may comprise a stimulating electrode 31. The stimulating electrode 31 may be configured to contact vagus innervated auricular skin of the wearer's first ear. The vagus innervated auricular skin that the stimulating electrode 31 is configured to contact may be selected from at least one of the following: the tragus 905, concha 906, 907 and external ear canal 904. The taVNS unit 30 may be configured to give electric stimuli to the vagus innervated auricular skin through its stimulating electrode 31 in a way similar to transcutaneous electric nerve stimulation (TENS).

The auricular EEG recording module 20 is in electronic communication with the processing unit 50, 401, through wire, Bluetooth or other connection means. The taVNS unit 30 is also in electronic communication with the processing unit 50, 401, through wire, Bluetooth or other connection means. The EEG recording module 20 may be configured to collect the wearer's EEG data and these data are transmitted to the processing unit 50, 401. With the help of various EEG analysis algorithms, the processing unit 50, 401, may be configured to analyze the EEG data to detect presence or cessation of EEG signals of wearer 900 suggestive of seizure. The processing unit 50, 401, may be further configured to analyze the EEG data to detect presence or cessation of EEG signals of wearer 900 suggestive of impending seizure.

When presence of EEG signals suggestive of seizure is detected by the processing unit 50, 401, the processing unit 50, 401, may be configured to automatically send signals to the taVNS unit 30 to actuate the taVNS unit 30 to send pre-determined electric stimuli immediately to the auricular branch of vagus nerve via stimulating electrode 31. The parameters of the electric stimuli for seizure, including the stimulating patterns, strength, duration, frequency and intervals, are pre-determined, such as shown in Table 3. (More examples of parameters were mentioned by various articles in the Background section of this application.)

TABLE 3

| Example of taVNS unit 30 electric stimuli output parameters for seizure (epilepsy). | |
| --- | --- |
| Output | Parameter |
| Power supply | Direct current 3-9 volts |
| Pulse width | 0.25-0.5 ms (range 0.13-1 ms) |
| Frequency | 10-25 Hz |
| Modes | Continuous wave or sparse-dense wave |
| Intensity | 0.25-1.75 mA |
| On/off time | 30 seconds (s) on/3 minutes (min) off (range 7 s-120 s on/18 s-30 min off) |
| Laterality | Bilateral or alternating between left and right |

When the processing unit 50, 401, detects presence of EEG signals suggestive of impending seizure, the processing unit 50, 401, may also be configured to automatically send signals to the taVNS unit 30 to actuate the taVNS unit 30 to send pre-determined electric stimuli immediately to the auricular branch of vagus nerve via stimulating electrode 31. The parameters of the electric stimuli for impending seizure are pre-determined, such as shown in Table 4.

TABLE 4

| Example of taVNS unit 30 electric stimuli output parameters for impending seizure (epilepsy) | |
| --- | --- |
| Output | Parameter |
| Power supply | Direct current 3-9 volts |
| Pulse width | 0.25-0.5 ms (range 0.13-1 ms) |
| Frequency | 10-25 Hz |
| Modes | Continuous wave or sparse-dense wave |
| Intensity | 0.25-1.25 mA |
| On/off time | 30 seconds (s) on/5 minutes (min) off (range 7 s-120 s on/18 s-60 min off) |
| Laterality | Bilateral or alternating between left and right |

When the processing unit 50, 401, detects cessation of EEG signals suggestive of seizure or cessation of EEG signals suggestive of impending seizure, the processing unit 50, 401, may be further configured to automatically send signals to the taVNS unit 30 to terminate the electric stimuli to the vagus nerve.

For most patients with seizures, two auricular EEG recording modules 20, one on each side of the head 901 coupled to each external ear 902 or each peri-auricular area 903, will be preferred. This is especially true for patients with generalized seizures or focal seizures which become secondarily generalized. In rare situations, only one auricular EEG recording module 20 may be utilized for patients with strictly localized seizures. For most patients with seizures, two taVNS units 30 will be utilized, with one taVNS unit 30 on each side of the head 901 coupled to each ear 902. In rare situations if the patient is unable to tolerate a taVNS unit 30 in one ear 902, only one taVNS unit 30 will be utilized and be placed in the other ear 902.

In some embodiments, the automatic detection-remedy system 101 configured as an automatic auricular anti-seizure system may further comprise a network interface 53, 406, configured to generate a notification (such as via a speaker 15, 404A, or a vibrator 17, 404B). One of the following structures can be adapted to house the components of this anti-seizure system: earbud style structure 61 (pod/bud), in-the-ear structure 62 (inserted), and behind-the-ear structure 63. The components which can be so housed in these structures include at least one of the following: the auricular EEG recording module 20, the taVNS unit 30, the processing unit 50, and notification device (e.g., speaker 15, vibrator 17, etc.), similar to descriptions hereinbefore.

A Third Preferred Embodiment

In preferred embodiments, an automatic detection-remedy system 101 may be configured as an automatic auricular anti-migraine system, comprising an auricular electroencephalogram (EEG) recording module 20, a transcutaneous auricular vagus nerve stimulation (taVNS) unit 30, and a processing unit 50, 401. The auricular EEG recording module 20 may comprise a plurality of miniature EEG sensor electrodes 12, 13, 72, 73, 82, 83, configured to contact separate areas selected from at least one of the following: the external ear canal 904 of the wearer's first ear, external ear 902 of the wearer's first ear, or peri-auricular area 903 around the wearer's first ear. The EEG recording module 20 may be configured to record EEG data of the wearer 900. The taVNS unit 30 may comprise a stimulating electrode 31. The stimulating electrode 31 may be configured to contact vagus innervated auricular skin of the wearer's first ear. The vagus innervated auricular skin that the stimulating electrode 31 is configured to contact may be selected from at least one of the following: the tragus 905, concha 906, 907, and external ear canal 904. The taVNS unit 30 may be configured to give electric stimuli to the vagus innervated auricular skin via its stimulating electrode 31, in a way similar to transcutaneous electric nerve stimulation (TENS).

The auricular EEG recording module 20 may be in electronic communication with the processing unit 50, 401, through wire, Bluetooth or other connection means. The taVNS unit 30 may also be in electronic communication with the processing unit 50, 401. The EEG recording module 20 may be configured to collect EEG data and these data are transmitted or otherwise electronically communicated to the processing unit 50, 401. With the help of various EEG analysis algorithms, the processing unit 50, 401, may be configured to analyze the EEG data to detect presence or cessation of EEG signals of wearer 900 suggestive of migraine. The processing unit 50, 401, may be further configured to analyze the EEG data to detect presence or cessation of EEG signals of wearer 900 suggestive of impending migraine.

When presence of EEG signals suggestive of migraine is detected by the processing unit 50, 401, the processing unit 50, 401, may be configured to automatically send signals to the taVNS unit 30 to actuate the taVNS unit 30 to send pre-determined electric stimuli immediately to the auricular branch of vagus nerve via stimulating electrode 31. The parameters of the electric stimuli for migraine, including the stimulating patterns, strength, duration, frequency and intervals, are pre-determined, such as shown in Table 5.

TABLE 5

| Example of taVNS unit 30 electric stimuli output parameters for migraine | |
| --- | --- |
| Output | Parameter |
| Power supply | Direct current 3-9 volts |
| Pulse width | 0.05-0.25 ms |
| Frequency | 1-25 Hz |
| Modes | Bi-phasic waveform |
| Intensity | 0.1-5.0 mA (Start at 0.1 mA, adjust at 0.1 mA increment till maximum tolerable intensity) |
| On/off time | 30 sec on/30 sec off |
| Sessions | 30-240 min/session, daily or 3 times/week, total duration 4-12 weeks |

When the processing unit 50, 401, detects presence of EEG signals suggestive of impending migraine, the processing unit 50, 401, may also be configured to automatically send signals to the taVNS unit 30 to actuate the taVNS unit 30 to send pre-determined electric stimuli immediately to the auricular branch of vagus nerve. The parameters of the electric stimuli for impending migraine are pre-determined, such as shown in Table 6.

TABLE 6

| Example of taVNS unit 30 electric stimuli output parameters for impending migraine | |
| --- | --- |
| Output | Parameter |
| Power supply | Direct current 3-9 volts |
| Pulse width | 0.05-0.25 ms |
| Frequency | 1-25 Hz |
| Modes | Bi-phasic waveform |
| Intensity | 0.1-3.0 mA (Start at 0.1 mA, adjust at 0.1 mA increment till maximum tolerable intensity) |
| On/off time | 30 sec on/30 sec off |
| Sessions | 30-200 min/session, daily or 3 times/week, total duration 4-8 weeks |

When the processing unit 50, 401, detects cessation of EEG signals suggestive of migraine or cessation of EEG signals suggestive of impending migraine, the processing unit 50, 401, may be further configured to automatically send signals to the taVNS unit 30 to stop the electric stimuli to the vagus nerve via stimulating electrode 31.

For most patients with migraine, two auricular EEG recording modules 20, one on each side of the head 901 coupled to each external ear 902 or each peri-auricular area 903, will be preferred. For most patients with migraine, two taVNS units 30 will be preferred, with one taVNS unit 30 on each side of the head 901 coupled to each external ear 902. In rare situations if the patient is unable to tolerate a taVNS unit 30 in one ear 902, only one taVNS unit 30 may be utilized and be placed in the other ear 902.

In some embodiments, the automatic detection-remedy system 101 configured as an automatic auricular anti-migraine system may further comprise a network interface 53, 406, configured to generate a notification (such as via a speaker 15, 404A, or a vibrator 17, 404B). One of the following structures can be adapted to house the components of this automatic auricular anti-migraine system: earbud style structure 61 (pod/bud), in-the-ear structure 62 (inserted), and behind-the-ear structure 63. The components which can be so housed in these structures include at least one of the following: the auricular EEG recording module 20, the taVNS unit 30, the processing unit 50, and notification device (e.g., speaker 15, vibrator 17, etc.) similar to descriptions hereinbefore.

A Fourth Preferred Embodiment

In some embodiments, an automatic detection-remedy system 101 may be configured as an automatic auricular anti-cluster headache system, comprising an auricular electroencephalogram (EEG) recording module 20, a transcutaneous auricular vagus nerve stimulation (taVNS) unit 30, and a processing unit 50, 401. The auricular EEG recording module 20 may comprise a plurality of (at least two, preferably more than two) miniature EEG sensor electrodes 12, 13, 72, 73, 82, 83, configured to contact separate areas selected from at least one of the following: the external ear canal 904 of the wearer's first ear, external ear 902 of the wearer's first ear, or peri-auricular area 903 around the wearer's first ear. The EEG recording module 20 may be configured to record EEG data of the wearer 400 via all of the EEG sensor electrodes 12, 13, 72, 73, 82, 83. The taVNS unit 30 may comprise a stimulating electrode 31. The stimulating electrode 31 may be configured to contact vagus innervated auricular skin of the wearer's first ear. The vagus innervated auricular skin that the stimulating electrode 31 is configured to contact may be selected from at least one of the following: the tragus 905, concha 906, 907, and external ear canal 904. The taVNS unit 30 may be configured to give electric stimuli via stimulating electrode 31 in a way similar to transcutaneous electric nerve stimulation (TENS).

The auricular EEG recording module 20 may be in electronic communication with the processing unit 50, 401, through Bluetooth, wire, or other connection means. The taVNS unit 30 may also be in electronic communication with the processing unit 50, 401. The EEG recording module 20 collects EEG data of the wearer and these EEG data are transmitted or otherwise communicated to the processing unit 50, 401. With the help of various EEG analysis algorithms, the processing unit 50, 401, may be configured to analyze the EEG data and detect presence or cessation of EEG signals of wearer 900 suggestive of cluster headache. The processing unit 50, 401, may be further configured to analyze the EEG data to detect presence or cessation of EEG signals of wearer 900 suggestive of impending cluster headache.

When presence of EEG signals suggestive of cluster headache is detected by the processing unit 50, 401, the processing unit 50, 401, may be configured to automatically send signals to the taVNS unit 30 to actuate the taVNS unit 30 to send pre-determined electric stimuli immediately to the auricular branch of vagus nerve via stimulating electrode 31. The parameters of the electric stimuli for cluster headache, including the stimulating patterns, strength, duration, frequency and intervals, are pre-determined, such as shown in Table 7.

TABLE 7

Example of taVNS unit 30 electric stimuli output parameters for cluster headache

| Output | Parameter |
| --- | --- |
| Power supply | Direct current 3-9 volts |
| Pulse width | 0.05-0.45 ms |
| Frequency | 10-30 Hz |
| Modes | Continuous wave or sparse-dense wave |
| Intensity | 0.1-5 mA |
| Sessions | 20-60 min/session, Duration 4 weeks |

When the processing unit 50, 401, detects presence of EEG signals suggestive of impending cluster headache, the processing unit 50, 401, may be configured to automatically send signals to the taVNS unit 30 to actuate the taVNS unit 30 to send pre-determined electric stimuli immediately to the auricular branch of vagus nerve. The electric stimuli parameters for impending cluster headache are pre-determined, such as shown in Table 8.

TABLE 8

Example of taVNS unit 30 electric stimuli output parameters for impending cluster headache

| Output | Parameter |
| --- | --- |
| Power supply | Direct current 3-9 volts |
| Pulse width | 0.05-0.45 ms |
| Frequency | 10-30 Hz |
| Modes | Continuous wave or sparse-dense wave |
| Intensity | 0.1-4.0 mA |
| Sessions | 20-60 min/session, Duration 3 weeks |

When the processing unit 50, 401, detects cessation of EEG signals suggestive of cluster headache or cessation of EEG signals suggestive of impending cluster headache, the processing unit 50, 401, may be further configured to automatically send signals to the taVNS unit 30 to terminate the electric stimuli to the vagus nerve provided via stimulating electrode 31.

For most patients with cluster headache, two auricular EEG recording modules 20, one on each side of the head 901 coupled to each external ear 902 or each peri-auricular area 903, will be preferred. For most patients with cluster headache, two taVNS units 30 will be preferred, with one taVNS unit 30 coupled to each external ear 902. In rare situations if the patient is unable to tolerate a taVNS unit 30 in one ear 902, only one taVNS unit 30 may be utilized and be placed in the other ear 902.

In some embodiments, the automatic detection-remedy system 101 configured as an automatic auricular anti-cluster headache system may further comprise a network interface 53, 406, configured to generate a notification (such as via a speaker 15, 404A, or a vibrator 17, 404B). One of the following structures can be adapted to house the components of this anti-cluster headache system: earbud style structure 61 (pod/bud), in-the-ear structure 62 (inserted), and behind-the-ear structure 63. The components which can be so housed in these structures include at least one of the following: the auricular EEG recording module 20, the ta VNS unit 30, the processing unit 50, and notification device (e.g., speaker 15, vibrator 17, etc.), similar to descriptions hereinbefore.

A Fifth Preferred Embodiment

In preferred embodiments, an automatic detection-remedy system 101 may be configured as an automatic auricular anti-major depressive disorder system, comprising an auricular electroencephalogram (EEG) recording module 20, a transcutaneous auricular vagus nerve stimulation (taVNS) unit 30, and a processing unit 50, 401. The auricular EEG recording module 20 may comprise a plurality of (at least two, preferably more than two) miniature EEG sensor electrodes 12, 13, 72, 73, 82, 83, configured to contact separate areas selected from at least one of the following: the external ear canal 904 of the wearer's first ear, external ear 902 of the wearer's first ear, or peri-auricular area 903 around the wearer's first ear. The EEG recording module 20 may be configured to record EEG data of the wearer 900 via all of the EEG sensor electrodes 12, 13, 72, 73, 82, 83. The taVNS unit 30 may comprise a miniature stimulating electrode 31. The stimulating electrode 31 may be configured to contact vagus innervated auricular skin of the wearer's first ear. The vagus innervated auricular skin that the stimulating electrode 31 is configured to contact may be selected from at least one of the following: the tragus 905, concha 906, 907, and external ear canal 904. The taVNS unit 30 may be configured to give electric stimuli via stimulating electrode 31, in a way similar to transcutaneous electric nerve stimulation (TENS).

The auricular EEG recording module 20 may be in electronic communication with the processing unit 50, 401, through wire, Bluetooth or other connection means. The taVNS unit 30 may also be in electronic communication with the processing unit 50, 401. The EEG recording module 20 collects the wearer's EEG data and these data are transmitted or otherwise communicated to the processing unit 50, 401. With the help of various EEG analysis algorithms, the processing unit 50, 401, may be configured to analyze the EEG data of the wearer 900 to detect presence or cessation of EEG signals suggestive of major depressive disorder. The processing unit 50, 401, may be further configured to analyze the EEG data of the wearer 900 to detect presence or cessation of EEG signals suggestive of impending major depressive disorder.

When presence of EEG signals suggestive of major depressive disorder is detected by the processing unit 50, 401, the processing unit 50, 401, may be configured to automatically send signals to the taVNS unit 30 to actuate the taVNS unit 30 to send pre-determined electric stimuli immediately to the auricular branch of vagus nerve via stimulating electrode 31. The parameters of the electric stimuli for major depressive disorder, including the stimulating patterns, strength, duration, frequency and intervals, are pre-determined, such as shown in Table 9.

TABLE 9

Example of taVNS unit 30 electric stimuli output
parameters for major depressive disorder

| Output | Parameter |
|---|---|
| Power supply | Direct current 3-9 volts |
| Pulse width | 0.2-1.0 ms |
| Frequency | 20-25 Hz |
| Modes | Continuous wave or sparse-dense wave |
| Intensity | 0.5-6.0 milliampere (mA) |
| On/off time | 30 sec on/30 sec off |
| Sessions | 60-240 min/day, 5-7 days/week, Duration 4-12 weeks |

When the processing unit 50, 401, detects presence of EEG signals suggestive of impending major depressive disorder, the processing unit 50, 401, may also be configured to automatically send signals to the taVNS unit 30 to actuate the taVNS unit 30 to send pre-determined electric stimuli immediately to the auricular branch of vagus nerve. The electric stimuli parameters for impending major depressive disorder are pre-determined, such as shown in Table 10.

TABLE 10

Example of taVNS unit 30 electric stimuli output parameters
for impending major depressive disorder

| Output | Parameter |
|---|---|
| Power supply | Direct current 3-9 volts |
| Pulse width | 0.2-1.0 ms |
| Frequency | 20-25 Hz |
| Modes | Continuous wave or sparse-dense wave |
| Intensity | 0.5-4.0 milliampere (mA) |
| On/off time | 30 sec on/30 sec off |
| Sessions | 60-220 min/day, 5-7 days/week, Duration 4-8 weeks |

When the processing unit 50, 401, detects cessation of EEG signals suggestive of major depressive disorder or cessation of EEG signals suggestive of impending major depressive disorder, the processing unit 50, 401, may be further configured to automatically send signals to the taVNS unit 30 to terminate the electric stimuli to the vagus nerve.

For most patients with major depressive disorder, two auricular EEG recording modules 20, one on each side of the head 901 coupled to each external ear 902 or each peri-auricular area 903, will be preferred. For most patients with major depressive disorder, two taVNS units 30 will be preferred, with one taVNS units 30 on each side of the head 901 coupled to each external ear 902. In rare situations if the patient is unable to tolerate a taVNS unit 30 in one ear 902, only one taVNS unit 30 will be utilized and be placed in the other ear 902.

In some embodiments, the automatic detection-remedy system 101 configured as an automatic auricular anti-major depressive disorder system may further comprise a network interface 53, 406, configured to generate a notification (such as via a speaker 15, 404A, or a vibrator 17, 404B). One of the following structures can be adapted to house the components of this anti-major depressive disorder system: earbud style structure 61 (pod/bud), in-the-ear structure 62 (inserted), and behind-the-ear structure 63. The components which can be so housed in these structures include at least one of the following: the auricular EEG recording module 20, the taVNS unit 30, the processing unit 50, and notification device (e.g., speaker 15, vibrator 17, etc.), similar to descriptions hereinbefore.

A Sixth Preferred Embodiment

In preferred embodiments, an automatic detection-remedy system 101 may be configured as an automatic auricular anti-bipolar disorder system, comprising an auricular electroencephalogram (EEG) recording module 20, a transcutaneous auricular vagus nerve stimulation (taVNS) unit 30, and a processing unit 50, 401. The auricular EEG recording module 20 may comprise a plurality of miniature EEG sensor electrodes 12, 13, 72, 73, 82, 83, configured to contact separate areas selected from at least one of the following: the external ear canal 904 of the wearer's first ear, external ear 902 of the wearer's first ear, or peri-auricular area 903 around the wearer's first ear. The EEG recording module 20 may be configured to record EEG data of the wearer 900 via EEG sensor electrodes 12, 13, 72, 73, 82, 83. The taVNS unit 30 includes a miniature stimulating electrode 31. The stimulating electrode 31 may be configured to contact vagus innervated auricular skin of the wearer's first ear. The vagus innervated auricular skin that the stimulating electrode 31 is configured to contact may be selected from at least one of the following: the tragus 905, concha 906, 907, and external ear canal 904. The taVNS unit 30 may be configured to give electric stimuli via stimulating electrode 31 in a way similar to transcutaneous electric nerve stimulation (TENS).

The auricular EEG recording module 20 may be in electronic communication with the processing unit 50, 401. The taVNS unit 30 may also be in electronic communication with the processing unit 50, 401. The EEG recording module 20 may collect the wearer's EEG data and these data are transmitted or otherwise communicated to the processing unit 50, 401. With the help of various EEG analysis algorithms, the processing unit 50, 401, may be configured to analyze the EEG data of the wearer 900 and detect presence or cessation of EEG signals suggestive of bipolar disorder. The processing unit 50, 401, may be further configured to analyze the EEG data of the wearer 900 and detect presence or cessation of EEG signals suggestive of impending bipolar disorder.

When presence of EEG signals suggestive of bipolar disorder is detected by the processing unit 50, 401, the processing unit 50, 401, may be configured to automatically send signals to the taVNS unit 30 to actuate the taVNS unit 30 to send pre-determined electric stimuli immediately to the auricular branch of vagus nerve via stimulating electrode 31. The parameters of the electric stimuli for bipolar disorder, including the stimulating patterns, strength, duration, frequency and intervals, are pre-determined, such as shown in Table 11.

TABLE 11

Example of taVNS unit 30 electric stimuli
output parameters for bipolar disorder

| Output | Parameter |
|---|---|
| Power supply | Direct current 3-9 volts |
| Pulse width | 0.25-1.0 ms |
| Frequency | 20-30 Hz |
| Modes | Continuous wave or sparse-dense wave |
| Intensity | 0.13-6.0 milliampere (mA) |
| On/off time | 30 sec on/60 sec off |
| Sessions | 30-180 min/day, 5-7 days/week, Duration 2-6 months |

When the processing unit 50, 401, detects presence of EEG signals suggestive of impending bipolar disorder, the processing unit 50, 401, may also be configured to automatically send signals to the taVNS unit 30 to actuate the taVNS unit 30 to send pre-determined electric stimuli immediately to the auricular branch of vagus nerve. The electric stimuli parameters for impending bipolar disorder are pre-determined such as shown in Table 12.

TABLE 12

Example of taVNS unit 30 electric stimuli output
parameters for impending bipolar disorder

| Output | Parameter |
|---|---|
| Power supply | Direct current 3-9 volts |
| Pulse width | 0.25-1.0 ms |
| Frequency | 20-30 Hz |
| Modes | Continuous wave or sparse-dense wave |
| Intensity | 0.13-4.0 milliampere (mA) |
| On/off time | 30 sec on/60 sec off |
| Sessions | 30-160 min/day, 5-7 days/week, Duration 2-4 months |

When the processing unit 50, 401, detected cessation of EEG signals suggestive of bipolar disorder or cessation of EEG signals suggestive of impending bipolar disorder, the processing unit 50, 401, may be further configured to automatically send signals to the taVNS unit 30 to terminate the electric stimuli to the vagus nerve.

For most patients with bipolar disorder, two auricular EEG recording modules 20, one on each side of the head 901 coupled to each external ear 902 or each peri-auricular area 903, will be preferred. For most patients with bipolar disorder, two taVNS units 30 will be preferred, with one taVNS unit 30 coupled to each external ear 902. In rare situations if the patient is unable to tolerate a taVNS unit 30 in one ear 902, only one taVNS unit 30 will be utilized and be placed in the other ear 902.

In some embodiments, the automatic detection-remedy system 101 configured as an automatic auricular anti-bipolar disorder system may further comprise a network interface 53, 406, configured to generate a notification (such as via a speaker 15, 404A, or a vibrator 17, 404B). One of the following structures can be adapted to house the components of this anti-bipolar disorder system: earbud style structure 61 (pod/bud), in-the-ear structure 62 (inserted), and behind-the-ear structure 63. The components which can be so housed in these structures include at least one of the following: the auricular EEG recording module 20, the taVNS unit 30, the processing unit 50, and notification device (e.g., speaker 15, vibrator 17, etc.), similar to descriptions hereinbefore.

A Seventh Preferred Embodiment

In preferred embodiments, an auricular EEG monitoring system 100 may comprise an auricular electroencephalogram (EEG) recording module 20 configured to be coupled to a wearer's first ear 902 or the peri-auricular area 903 around the wearer's first ear. The EEG recording module 20 includes a plurality of EEG sensor electrodes 12, 13, 72, 73, 82, 83. These EEG sensor electrodes 12, 13, 72, 73, 82, 83, are configured to contact separate areas selected from at least one of the following: the external ear canal 904 of the wearer's first ear, external ear 902 of the wearer's first ear, or peri-auricular area 903 around the wearer's first ear. The auricular EEG monitoring system 100 may further comprise a processing unit 50, 401. The auricular EEG recording module 20 may be in electronic communication with the processing unit 50, 401, through wire, Bluetooth or other connection means. The auricular EEG recording module 20 may be configured to collect EEG data of the wearer 900 via all of the EEG sensor electrodes 12, 13, 72, 73, 82, 83. These EEG data are transmitted or otherwise communicated to the processing unit 50, 401. With the help of various EEG analysis algorithms, the processing unit 50, 401, may be configured to analyze the EEG data of the wearer 900 for detection of EEG signals suggestive of one or more neuropsychiatric disorders or one or more impending neuropsychiatric disorders. The processing unit 50, 401, may be further configured to detect cessation of EEG signals suggestive of the neuropsychiatric disorder(s) or cessation of EEG signals suggestive of the impending neuropsychiatric disorder(s). The neuropsychiatric disorders may include seizure, migraine, cluster headache, major depressive disorder, and bipolar disorder.

The auricular EEG monitoring system 100 may further comprise a network interface 53, 403, configured to generate a notification. The network interface 53, 403, may be in electronic communication with the processing unit 50, 401. When the processing unit 50, 401, detects presence of EEG signals of a wearer 900 suggestive of one or more neuropsychiatric disorders or presence of EEG signals suggestive of one or more impending neuropsychiatric disorders, the network interface 53, 403, may be configured to send warning notification to a notification device (e.g., speaker 15, 404A, vibrator 17, 404B, etc.) for the wearer 900 of the auricular EEG monitoring system 100 and the wearer's healthcare provider 950 to take appropriate actions. One example of the notification device is a speaker 15, 404A, configured to generate audible warning notification when presence of EEG signals suggestive of a neuropsychiatric disorder or presence of EEG signals suggestive of an impending neuropsychiatric disorder is detected. Another example of a notification device is a vibrator 17, 404B, configured to generate tactile notification when presence of EEG signals suggestive of a neuropsychiatric disorder or impending neuropsychiatric disorder is detected.

The auricular EEG recording module 20, the processing unit 50, 401, and the network interface 53 may be configured to be housed in one of the following structures: earbud style structure 61 (pod/bud), in-the-ear structure 62 (inserted), and behind-the-ear structure 63. The earbud style structure 61 would be particularly preferred for housing purpose. All of the EEG sensor electrodes 12, 13, 72, 73, 82, 83, may be placed on the surface of the horizontal portion 25 of the earbud style structure 61. Preferably the earbud style structure 61 may be made with or may comprise an elastic flexible and adaptable material, in which the material for the earbud style structure 61 is configured to have appropriate elasticity, flexibility and adaptability such that when the earbud style structure 61 is inserted into a wearer's external ear canal 904, it will naturally adapt to the contour of the wearer's external ear canal 904 and may snugly fill the interior of the wearer's external ear canal 904. (FIG. 8). This set-up and the flexibility, elasticity and adaptability of the material will enable all of these EEG sensor electrodes 12, 13, 72, 73, 82, 83, to be naturally in close contact with the skin of the wearer's external ear canal 904 when it is inserted into the wearer's external ear canal 904. Attaching and removing all of these EEG sensor electrodes 12, 13, 72, 73, 82, 83, will be as easy as inserting and removing the earbud style structure 61 from the wearer's external ear canal 904. There will be no need for a certified technologist to apply or remove all of the EEG sensor electrodes 12, 13, 72, 73, 82, 83. Applying adhesive material to secure all of these EEG sensor electrodes 12, 13, 72, 73, 82, 83, will also be unnecessary. This is due to the unique anatomical features of the human external ear canal 904, as illustrated in FIG. 8. This will offer huge convenience for the wearer 900. These advantages can be similarly achieved when using a housing adapted from the in-the-ear portion 27 of a behind-the-ear structure 63 (behind-the-ear-hearing-aid-style structure) by placing all of the EEG sensor electrodes 12, 13, 72, 73, 82, 83, on the surface of the in-the-ear portion 27 and by using flexible elastic and adaptable material for the in-the-ear portion 27, in which the material for the in-the-ear portion is configured to have appropriate flexibility, elasticity and adaptability such that when the in-the-ear portion 27 is inserted into a wearer's external ear canal 904, it will naturally adapt to the contour of the wearer's external ear canal 904 and may snugly fill the interior of the wearer's external ear canal 904. Therefore, all of the EEG sensor electrodes 12, 13, 72, 73, 82, 83, will be naturally in close contact with the skin of the wearer's external ear canal 904 when the in-the-ear portion 27 is inserted into the wearer's external ear canal 904.

In some embodiments, an EEG recording housing 11 of an auricular EEG monitoring system 100 may be shaped or configured as a tubular-shaped structure 66 and all of the EEG sensor electrodes 12, 13, 72, 73, 82, 83 are configured to be located at the surface 91 of the tubular-shaped structure 66 and so that all of the EEG sensor electrodes 12, 13, 72, 73, 82, 83, are housed in the tubular-shaped structure 66. In preferred embodiments, one or more of the EEG sensor electrodes 12, 13, 72, 73, 82, 83, is/are configured to be located at the upper surface 91 (upper surface at approximately 90 degrees above horizontal level 92, as shown by electrodes 12, 13, in FIGS. 19, 22, 25) of the tubular-shaped structure 66. In preferred embodiments, one or more of the EEG sensor electrodes 12, 13, 72, 73, 82, 83, is/are configured to be located at between 0 and 90 degrees, and more preferably at approximately 45 degrees (plus or minus fifteen degrees) above the horizontal level 92 of the tubular-shaped structure 66 and is/are configured to face forward-upward direction 93 (e.g., as shown by electrodes 72, 82, in FIGS. 19, 21, 24). In preferred embodiments, one or more of the EEG sensor electrodes 12, 13, 72, 73, 82, 83, is/are configured to be located at between 90 and 180 degrees, and more preferably at approximately 135 degrees (plus or minus fifteen degrees) above the horizontal level 92 of the tubular structure 66 and is/are configured to face backward-upward direction 94 (e.g., as shown by electrodes 73, 83, in FIGS. 19, 23, 26). (Upper surface, horizontal level, forward, backward and upward all refer to directions relative to the head 901 of the wearer 900 with the wearer in upright position after the tubular-shaped structure 66 has been inserted into a wearer's external ear canal 904.) The tubular-shaped structure 66 is configured to be made of elastic flexible and adaptable material, in which the material of the tubular-shaped structure 66 is configured to have appropriate elasticity, flexibility and adaptability such that when the tubular-shaped structure 66 is inserted into a wearer's external ear canal 904, all of the EEG sensor electrodes 12, 13, 72, 73, 82, 83, will be naturally in close contact with the skin of the wearer's external ear canal 904. This set-up will allow the wearer 900 to attach or to remove all of the EEG sensor electrodes 12, 13, 72, 73, 82, 83, as easily as inserting or removing the tubular-shaped structure 66 into (or from) the wearer's 900 external ear canal 904.

In some embodiments, an auricular EEG monitoring system 100 may further comprise a second auricular EEG recording module 20. The first EEG recording module 20 may be configured to be coupled to the wearer's first ear 902 or the peri-auricular area 903 around the wearer's first ear; and the second EEG recording module 20 may be configured to be coupled to the wearer's second ear 902 or the peri-auricular area 903 around the wearer's second ear. The second EEG recording module 20 may comprise a plurality (at least two, but preferably more than two) of EEG sensor electrodes 12, 13, 72, 73, 82, 83, configured to contact separate areas selected from at least one of the following: external ear canal 904 of the wearer's second ear, external ear 902 of the wearer's second ear, and/or peri-auricular area 903 around the wearer's second ear. The second EEG recording module 20 may be in electronic communication with the processing unit 50, 401, through Bluetooth or other connection means. The second auricular EEG recording module 20 may be configured to collect EEG data of the wearer 900 via all of its EEG sensor electrodes 12, 13, 72, 73, 82, 83. These EEG data may be transmitted to the processing unit 50, 401. With the help of various EEG analysis algorithms, the processing unit 50, 401, may be configured to analyze the EEG data of the wearer 900 for detection of presence of EEG signals suggestive of one or more neuropsychiatric disorders or presence of EEG signals suggestive of one or more impending neuropsychiatric disorders. The processing unit 50, 401, may be further configured to detect cessation of EEG signals suggestive of the neuropsychiatric disorder or cessation of the EEG signals suggestive of the impending neuropsychiatric disorder. With bilateral EEG data collection, this auricular EEG monitoring system 100 will be able to more widely collect EEG data from both sides of the wearer's brain to help more accurately detect presence or cessation of EEG signals suggestive of neuropsychiatric disorders and presence or cessation of EEG signals suggestive of impending neuropsychiatric disorders.

There are many conventional smart watches or health trackers that contain monitoring devices 71 to monitor various body functions, including electrocardiogram (ECG), heart rate, blood oxygen, sleep, body temperature, and motion, etc. (as known in the art). However, none of them can monitor the most important part of the human body, which is the brain. This auricular EEG monitoring system 100, can easily combine with other monitoring devices 71 by placing their monitoring sensors in the external ear 902 or the external ear canal 904. Thus, this combined system 100 can monitor not only the brain (through EEG), it can also monitor other body functions, such as ECG, heart rate, blood oxygen, motion, sleep, and body temperature, etc.

While some exemplary shapes and sizes have been provided for elements of the auricular EEG monitoring system 100 and automatic detection-remedy system 101 it should be understood to one of ordinary skill in the art that the elements described herein may be configured in a plurality of sizes and shapes including "T" shaped, "X" shaped, square shaped, rectangular shaped, cylinder shaped, cuboid shaped, hexagonal prism shaped, triangular prism shaped, or any other geometric or non-geometric shape, including combinations of shapes. It is not intended herein to mention all the possible alternatives, equivalent forms or ramifications of the invention. It is understood that the terms and proposed shapes used herein are merely descriptive, rather than limiting, and that various changes, such as to size and shape, may be made without departing from the spirit or scope of the invention.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. An automatic detection-remedy system, comprising:

an auricular electroencephalogram (EEG) monitoring system, comprising a first EEG recording module having a plurality of EEG sensor electrodes, wherein the first EEG recording module is in electronic communication with each EEG sensor electrode of the first EEG recording module, wherein each EEG sensor electrode of the first EEG recording module is configured to contact separate areas of a wearer's skin selected from at least one of the following: external ear canal of a first ear of the wearer, external ear of the wearer's first ear, and peri-auricular area around the wearer's first ear, and wherein the first EEG recording module is configured to record EEG data of the wearer;

a first transcutaneous auricular vagus nerve stimulation unit (first taVNS unit), the first taVNS unit having a first stimulating electrode configured to contact vagus innervated auricular skin of the wearer's first ear, wherein the vagus innervated auricular skin that the first stimulating electrode is configured to contact is selected from at least one of the following: external ear canal of the wearer's first ear, tragus of the wearer's first ear, cymba concha of the wearer's first ear and cavum concha of the wearer's first ear; and a processing unit in electronic communication with the auricular EEG monitoring system and the first taVNS unit;

wherein the processing unit is configured to analyze the EEG data recorded by the auricular EEG monitoring system to detect the presence or cessation of EEG signals suggestive of seizure; wherein when presence of EEG signals suggestive of seizure is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with; and wherein when cessation of EEG signals suggestive of seizure is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with;

wherein the processing unit is configured to analyze the EEG data recorded by the auricular EEG monitoring system to detect presence or cessation of EEG signals suggestive of migraine; wherein when presence of EEG signals suggestive of migraine is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with; and wherein when cessation of EEG signals suggestive of migraine is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with; and wherein the processing unit is configured to analyze the EEG data recorded by the auricular EEG monitoring system to detect presence or cessation of EEG signals suggestive of cluster headache; wherein when presence of EEG signals suggestive of cluster headache is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with; and wherein when cessation of EEG signals suggestive of cluster headache is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with.

2. The automatic detection-remedy system of claim 1, wherein the processing unit is further configured to analyze the EEG data recorded by the auricular EEG monitoring system to detect presence or cessation of EEG signals suggestive of impending seizure, wherein when presence of EEG signals suggestive of impending seizure is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, and wherein when cessation of EEG signals suggestive of impending seizure is detected by the processing unit, the processing unit is configured to immediately send signals to the first taVNS unit to automatically stop sending pre-determined electric stimuli to the vagus innervated auricular skin of the wearer's first ear to which the first stimulating electrode is in contact with;

wherein the processing unit is further configured to analyze the EEG data recorded by the auricular EEG monitoring system to detect presence or cessation of EEG signals suggestive of impending migraine, wherein when presence of EEG signals suggestive of impending migraine is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, and wherein when cessation of EEG signals suggestive of impending migraine is detected by the processing unit, the processing unit is configured to immediately send signals to the first taVNS unit to automatically stop sending pre-determined electric stimuli to the vagus innervated auricular skin of the wearer's first ear to which the first stimulating electrode is in contact with; and wherein the processing unit is further configured to analyze the EEG data recorded by the auricular EEG monitoring system to detect presence or cessation of EEG signals suggestive of impending cluster headache, wherein when presence of EEG signals suggestive of impending cluster headache is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, and wherein when cessation of EEG signals suggestive of impending cluster headache is detected by the processing unit, the processing unit is configured to immediately send signals to the first taVNS unit to automatically stop sending pre-determined electric stimuli to the vagus innervated auricular skin of the wearer's first ear to which the first stimulating electrode is in contact with.

3. An automatic detection-remedy system, comprising:

an auricular electroencephalogram (EEG) monitoring system, comprising a first EEG recording module having a plurality of EEG sensor electrodes, wherein the first EEG recording module is in electronic communication with each EEG sensor electrode of the first EEG recording module, wherein each EEG sensor electrode of the first EEG recording module is configured to contact separate area of a wearer's skin selected from at least one of the following: an external ear canal of a first ear of the wearer, an external ear of the wearer's first ear, and a peri-auricular area around the wearer's first ear, and wherein the first EEG recording module is configured to record EEG data of the wearer;

a first transcutaneous auricular vagus nerve stimulation unit (first taVNS unit), the first taVNS unit having a first stimulating electrode configured to contact vagus innervated auricular skin of the wearer's first ear, wherein the vagus innervated auricular skin that the first stimulating electrode is configured to contact is selected from at least one of the following: the external ear canal of the wearer's first ear, tragus of the wearer's first ear, cymba concha of the wearer's first ear and cavum concha of the wearer's first ear;

a network interface; and a processing unit, wherein the processing unit is in electronic communication with the auricular EEG monitoring system and the first ta VNS unit;

wherein the processing unit is configured to analyze the EEG data recorded by the auricular EEG monitoring system to detect presence or cessation of EEG signals suggestive of one or more neuropsychiatric disorders;

wherein when presence of EEG signals suggestive of the one or more neuropsychiatric disorders is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with;

wherein when cessation of EEG signals suggestive of the one or more neuropsychiatric disorders is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with;

wherein the processing unit is further configured to analyze the EEG data recorded by the auricular EEG monitoring system to detect presence or cessation of EEG signals suggestive of one or more impending neuropsychiatric disorders;

wherein when presence of EEG signals suggestive of the one or more impending neuropsychiatric disorders is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with;

wherein when cessation of EEG signals suggestive of the one or more impending neuropsychiatric disorders is detected by the processing unit, the processing unit is configured to immediately send signals to the first taVNS unit to automatically stop sending pre-determined electric stimuli to the vagus innervated auricular skin of the wearer's first ear to which the first stimulating electrode is in contact with; and wherein the network interface is in electronic communication with the processing unit, wherein the network interface is configured to generate a notification to a client device when the processing unit detects presence of EEG signals suggestive of the one or more neuropsychiatric disorders, wherein the network interface is further configured to generate a notification to the client device when the processing unit detects presence of EEG signals suggestive of the one or more impending neuropsychiatric disorders, wherein the network interface is configured to generate a notification to the client device when the processing unit detects cessation of EEG signals suggestive of the one or more neuropsychiatric disorders, and wherein the network interface is further configured to generate a notification to the client device when the processing unit detects cessation of EEG signals suggestive of the one or more impending neuropsychiatric disorders.

4. The automatic detection-remedy system of claim 3, wherein the one or more neuropsychiatric disorders comprises seizure, wherein when presence of EEG signals suggestive of seizure is detected by the processing unit, the processing unit is configured to immediately send signals to the first taVNS unit to automatically start sending predetermined electric stimuli to the vagus innervated auricular skin of the wearer's first ear to which the first stimulating electrode is in contact with, wherein when cessation of EEG signals suggestive of seizure is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with, wherein when presence of EEG signals suggestive of impending seizure is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, and wherein when cessation of EEG signals suggestive of impending seizure is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with.

5. The automatic detection-remedy system of claim 3, wherein the one or more neuropsychiatric disorders comprises migraine, wherein when presence of EEG signals suggestive of migraine is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, wherein when cessation of EEG signals suggestive of migraine is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with, wherein when presence of EEG signals suggestive of impending migraine is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, and wherein when cessation of EEG signals suggestive of impending migraine is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with.

6. The automatic detection-remedy system of claim 3, wherein the one or more neuropsychiatric disorders comprises cluster headache, wherein when presence of EEG signals suggestive of cluster headache is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, wherein when cessation of EEG signals suggestive of cluster headache is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with, wherein when presence of EEG signals suggestive of impending cluster headache is detected by the processing unit, the processing unit is configured to immediately send signals to the first taVNS unit to automatically start sending predetermined electric stimuli to the vagus innervated auricular skin of the wearer's first ear to which the first stimulating electrode is in contact with, and wherein when cessation of EEG signals suggestive of impending cluster headache is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with.

7. The automatic detection-remedy system of claim 3, wherein the one or more neuropsychiatric disorders comprises major depressive disorder, wherein when presence of EEG signals suggestive of major depressive disorder is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, wherein when cessation of EEG signals suggestive of major depressive disorder is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with, wherein when presence of EEG signals suggestive of impending major depressive disorder is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, and wherein when cessation of EEG signals suggestive of impending major depressive disorder is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with.

8. The automatic detection-remedy system of claim 3, wherein the one or more neuropsychiatric disorders comprises bipolar disorder, wherein when presence of EEG signals suggestive of bipolar disorder is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, wherein when cessation of EEG signals suggestive of bipolar disorder is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with, wherein when presence of EEG signals suggestive of impending bipolar disorder is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, and wherein when cessation of EEG signals suggestive of impending bipolar disorder is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with.

9. The automatic detection-remedy system of claim 3, wherein all of the EEG sensor electrodes of the first EEG recording module and the first stimulating electrode of the first taVNS unit are configured to be housed within an earbud-style structure, wherein the earbud-style structure is coupled with the wearer's first ear, wherein all of the EEG sensor electrodes of the first EEG recording module and the first stimulating electrode of the first taVNS unit are configured to be located on a surface of a horizontal portion of the earbud-style structure, wherein the earbud-style structure comprises elastic flexible and adaptable material, and wherein the elastic flexible and adaptable material of the earbud-style structure is configured to have appropriate elasticity flexibility and adaptability such that all of the EEG sensor electrodes of the first EEG recording module and the first taVNS stimulating electrode are naturally in close contact with the skin of the external ear canal of the wearer's first ear and such that the first taVNS stimulating electrode is naturally in close contact with vagus innervated auricular skin of the wearer's first ear when the earbud-style structure is inserted into the external ear canal of the wearer's first ear.

10. The automatic detection-remedy system of claim 3, wherein all of the EEG sensor electrodes of the first EEG recording module and the first stimulating electrode of the first taVNS unit are configured to be housed within a behind-the-ear-hearing-aid-style structure, wherein the behind-the-ear-hearing-aid-style structure is coupled with the wearer's first ear, wherein the behind-the-ear-hearing-aid-style structure comprises a behind-the-ear portion and an in-the-ear portion, wherein all of the EEG sensor electrodes of the first EEG recording module and the first stimulating electrode of the first taVNS unit are configured to be located on a surface of the in-the-ear portion, wherein the in-the-ear portion comprises elastic flexible and adaptable material, and wherein the elastic flexible and adaptable material of the in-the-ear portion is configured to have appropriate elasticity flexibility and adaptability such that all of the EEG sensor electrodes of the first EEG recording module and the first taVNS stimulating electrode are naturally in close contact with the skin of the external ear canal of the wearer's first ear and such that the first taVNS stimulating electrode is naturally in close contact with vagus innervated auricular skin of the wearer's first ear when the in-the-ear portion is inserted into the external ear canal of the wearer's first ear.

11. The automatic detection-remedy system of claim 3, further comprising a speaker in electronic communication with the network interface, wherein the speaker is configured to generate an audible notification when the processing unit detects the presence of EEG signals suggestive of the one or more neuropsychiatric disorders, wherein the speaker is configured to generate an audible notification when the processing unit detects the presence of EEG signals suggestive of the one or more impending neuropsychiatric disorders, wherein the speaker is configured to generate an audible notification when the processing unit detects cessation of EEG signals suggestive of the one or more neuropsychiatric disorders, and wherein the speaker is further configured to generate an audible notification when the processing unit detects cessation of EEG signals suggestive of the one or more impending neuropsychiatric disorders.

12. The automatic detection-remedy system of claim 3, further comprising a vibrator in electronic communication with the network interface, wherein the vibrator is configured to generate a tactile notification when the processing unit detects the presence of EEG signals suggestive of the one or more neuropsychiatric disorders, wherein the vibrator is configured to generate a tactile notification when the processing unit detects the presence of EEG signals suggestive of the one or more impending neuropsychiatric disorders, wherein the vibrator is configured to generate a tactile notification when the processing unit detects cessation of EEG signals suggestive of the one or more neuropsychiatric disorders, and wherein the vibrator is further configured to generate a tactile notification when the processing unit detects cessation of EEG signals suggestive of the one or more impending neuropsychiatric disorders.

13. The automatic detection-remedy system of claim 3, wherein the auricular EEG monitoring system further comprises a second EEG recording module, wherein the second EEG recording module includes a plurality of EEG sensor electrodes configured to contact separate areas of the wearer's skin selected from at least one of the following: external ear canal of a second ear of the wearer, external ear of the wearer's second ear, and a peri-auricular area around the wearer's second ear, wherein each EEG sensor electrode of the second EEG recording module is in electronic communication with the second EEG recording module, wherein the second EEG recording module is configured to record EEG data of the wearer, and wherein the second EEG recording module is in electronic communication with the processing unit.

14. The automatic detection-remedy system of claim 3, wherein the automatic detection-remedy system further comprises a second transcutaneous auricular vagus nerve stimulation unit (second taVNS unit), wherein the second taVNS unit comprises a second stimulating electrode configured to contact vagus innervated auricular skin of the wearer's second ear, wherein the vagus innervated auricular skin that the second stimulating electrode is configured to contact is selected from at least one of the following: external ear canal of the wearer's second ear, tragus of the wearer's second ear, cymba concha of the wearer's second ear and cavum concha of the wearer's second ear, wherein the second taVNS unit is in electronic communication with the processing unit, wherein when presence of EEG signals suggestive of the one or more neuropsychiatric disorders is detected by the processing unit, the processing unit is further configured to immediately send signals to the second taVNS unit to automatically start sending pre-determined electric stimuli to the vagus innervated auricular skin of the wearer's second ear to which the second stimulating electrode is in contact with, wherein when cessation of EEG signals suggestive of the one or more neuropsychiatric disorders is detected by the processing unit, the processing unit is configured to immediately send signals to the second taVNS unit to automatically stop the electric stimuli to the vagus innervated auricular skin of the wearer's second ear to which the second stimulating electrode is in contact with, wherein when presence of EEG signals suggestive of the one or more impending neuropsychiatric disorders is detected by the processing unit, the processing unit is further configured to immediately send signals to the second taVNS unit to automatically start sending pre-determined electric stimuli to the vagus innervated auricular skin of the wearer's second ear to which the second stimulating electrode is in contact with, and wherein when cessation of EEG signals suggestive of the one or more impending neuropsychiatric disorders is detected by the processing unit, the processing unit is configured to immediately send signals to the second taVNS unit to automatically stop the electric stimuli to the vagus innervated auricular skin of the wearer's second ear to which the second stimulating electrode is in contact with.

15. An automatic detection-remedy system, comprising:
a first transcutaneous auricular vagus nerve stimulation unit (first taVNS unit), the first taVNS unit having a first stimulating electrode configured to contact vagus innervated auricular skin of a first ear of a wearer;
an auricular electroencephalogram (EEG) monitoring system, comprising a first EEG recording module having a plurality of EEG sensor electrodes, wherein the first EEG recording module is in electronic communication with each EEG sensor electrode of the first EEG recording module, wherein the first EEG recording module is configured to record EEG data of the wearer, wherein all of the EEG sensor electrodes of the first EEG recording module and the first stimulating electrode of the first taVNS unit are configured to be housed in a tubular-shaped structure, wherein the tubular-shaped structure is coupled with the first ear of the wearer, wherein all of the EEG sensor electrodes of the first EEG recording module and the first stimulating electrode of the first taVNS unit are configured to be located on a surface of the tubular-shaped structure, wherein one or more EEG sensor electrode(s) are located at the upper surface of the tubular-shaped structure, wherein one or more EEG sensor electrode(s) are located 30-60 degrees above the horizontal level of the tubular-shaped structure and are facing forward-upward, wherein one or more EEG sensor electrode(s) are located at 120-150 degrees above the horizontal level of the tubular-shaped structure and are facing backward-upward, wherein the tubular-shaped structure comprises an elastic flexible and adaptable material, and wherein the elastic flexible and adaptable material of the tubular shaped structure is configured to have appropriate elasticity flexibility and adaptability such that all of the EEG sensor electrodes of the first EEG recording module and the first stimulating electrode of the first taVNS unit are naturally in close contact with the skin of the external ear canal of the wearer's first ear and such that the first ta VNS stimulating electrode is naturally in close contact with vagus innervated auricular skin when the tubular-shaped structure is inserted into the external ear canal of the wearer's first ear; and a processing unit in electronic communication with the auricular EEG monitoring system and the first taVNS unit, wherein the processing unit is configured to analyze the EEG data recorded by the auricular EEG monitoring system to detect presence or cessation of EEG signals suggestive of one or more neuropsychiatric disorders, wherein when presence of EEG signals suggestive of the one or more neuropsychiatric disorders is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, and wherein when cessation of EEG signals suggestive of the one or more neuropsychiatric disorders is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with.

16. The automatic detection-remedy system of claim 15, wherein the processing unit is further configured to analyze the EEG data recorded by the auricular EEG monitoring system to detect presence or cessation of EEG signals suggestive of one or more impending neuropsychiatric disorders, wherein when the presence of EEG signals suggestive of the one or more impending neuropsychiatric disorders is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, and wherein when cessation of EEG signals suggestive of the one or more impending neuropsychiatric disorders is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with.

17. The automatic detection-remedy system of claim 16, further comprises a second EEG recording module, wherein the second EEG recording module includes a plurality of EEG sensor electrodes configured to contact separate areas selected from at least one of the following: external ear canal of the wearer's second ear, external ear of the wearer's second ear, and peri-auricular area around the wearer's second ear; wherein the second EEG recording module is in electronic communication with each EEG sensor electrode of the second EEG recording module, wherein the second EEG recording module is configured to record EEG data of the wearer; and wherein the second EEG recording module is in electronic communication with the processing unit.

18. The automatic detection-remedy system of claim 16, wherein the one or more neuropsychiatric disorders comprise seizure, wherein when presence of EEG signals suggestive of seizure is detected by the processing unit, the processing unit is configured to immediately send signals to the first taVNS unit to automatically start sending predetermined electric stimuli to the vagus innervated auricular skin of the wearer's first ear to which the first stimulating electrode is in contact with, wherein when cessation of EEG signals suggestive of seizure is detected by the processing unit, the processing unit is configured to immediately send signals to the first taVNS unit to automatically stop sending pre-determined electric stimuli to the vagus innervated auricular skin of the wearer's first ear to which the first stimulating electrode is in contact with, wherein when presence of EEG signals suggestive of impending seizure is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, and wherein when cessation of EEG signals suggestive of impending seizure is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with.

19. The automatic detection-remedy system of claim 16, wherein the one or more neuropsychiatric disorders comprise migraine, wherein when presence of EEG signals suggestive of migraine is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, wherein when cessation of EEG signals suggestive of migraine is detected by the processing unit, the processing unit is configured to immediately send signals to the first taVNS unit to automatically stop sending pre-determined electric stimuli to the vagus innervated auricular skin of the wearer's first ear to which the first stimulating electrode is in contact with, wherein when presence of EEG signals suggestive of impending migraine is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, and wherein when cessation of EEG signals suggestive of impending migraine is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with.

20. The automatic detection-remedy system of claim 16, wherein the one or more neuropsychiatric disorders comprise cluster headache, wherein when presence of EEG signals suggestive of cluster headache is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, wherein when cessation of EEG signals suggestive of cluster headache is detected by the processing unit, the processing unit is configured to immediately send signals to the first taVNS unit to automatically stop sending pre-determined electric stimuli to the vagus innervated auricular skin of the wearer's first ear to which the first stimulating electrode is in contact with, wherein when presence of EEG signals suggestive of impending cluster headache is detected by the processing unit, the processing unit is configured to immediately send signals to the first taVNS unit to automatically start sending predetermined electric stimuli to the vagus innervated auricular skin of the wearer's first ear to which the first stimulating electrode is in contact with, and wherein when cessation of EEG signals suggestive of impending cluster headache is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with.

21. The automatic detection-remedy system of claim 16, wherein the one or more neuropsychiatric disorders comprise major depressive disorder, wherein when presence of EEG signals suggestive of major depressive disorder is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, wherein when cessation of EEG signals suggestive of major depressive disorder is detected by the processing unit, the processing unit is configured to immediately send signals to the first taVNS unit to automatically stop sending pre-determined electric stimuli to the vagus innervated auricular skin of the wearer's first ear to which the first stimulating electrode is in contact with, wherein when presence of EEG signals suggestive of impending major depressive disorder is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, and wherein when cessation of EEG signals suggestive of impending major depressive disorder is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with.

22. The automatic detection-remedy system of claim 16, wherein the one or more neuropsychiatric disorders comprise bipolar disorder, wherein when presence of EEG signals suggestive of bipolar disorder is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, wherein when cessation of EEG signals suggestive of bipolar disorder is detected by the processing unit, the processing unit is configured to immediately send signals to the first taVNS unit to automatically stop sending pre-determined electric stimuli to the vagus innervated auricular skin of the wearer's first ear to which the first stimulating electrode is in contact with, wherein when presence of EEG signals suggestive of impending bipolar disorder is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, and wherein when cessation of EEG signals suggestive of impending bipolar disorder is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with.

23. The automatic detection-remedy system of claim 16, further comprising a network interface in electronic communication with the processing unit, wherein the network interface is configured to generate a notification to a client device when the processing unit detects presence of EEG signals suggestive of the one or more neuropsychiatric disorders, wherein the network interface is configured to generate a notification to the client device when the processing unit detects presence of EEG signals suggestive of the one or more impending neuropsychiatric disorders, wherein the network interface is configured to generate a notification to the client device when the processing unit detects cessation of EEG signals suggestive of the one or more neuropsychiatric disorders, and wherein the network interface is further configured to generate a notification to the client device when the processing unit detects cessation of EEG signals suggestive of the one or more impending neuropsychiatric disorders.

24. An automatic detection-remedy system, comprising:
an auricular electroencephalogram (EEG) monitoring system, comprising a first EEG recording module, wherein the first EEG recording module includes a plurality of EEG sensor electrodes, wherein the first EEG recording module is in electronic communication with each EEG sensor electrode of the first EEG recording module, wherein each EEG sensor electrode is configured to contact separate area of a wearer's skin selected from at least one of the following: external ear canal of a first ear of the wearer, external ear of the wearer's first ear, and peri-auricular area around the wearer's first ear, and wherein the first EEG recording module is configured to record EEG data of the wearer;
a first transcutaneous auricular vagus nerve stimulation unit (first taVNS unit), the first taVNS unit having a first stimulating electrode configured to contact vagus innervated auricular skin of the wearer's first ear, wherein the vagus innervated auricular skin that the first stimulating electrode is configured to contact is selected from at least one of the following: external ear canal of the wearer's first ear, tragus of the wearer's first ear, cymba concha of the wearer's first ear and cavum concha of the wearer's first ear; and a processing unit in electronic communication with the auricular EEG monitoring system and the first taVNS unit;

wherein the processing unit is configured to analyze the EEG data recorded by the EEG monitoring system to detect presence or cessation of EEG signals suggestive of major depressive disorder; wherein when presence of EEG signals suggestive of major depressive disorder is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with; wherein when cessation of EEG signals suggestive of major depressive disorder is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with; and wherein the processing unit is configured to analyze the EEG data recorded by the EEG monitoring system to detect presence or cessation of EEG signals suggestive of bipolar disorder; wherein when presence of EEG signals suggestive of bipolar disorder is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with; and wherein when cessation of EEG signals suggestive of bipolar disorder is detected by the processing unit, the processing unit is further configured to immediately send signals to the first taVNS unit to automatically stop sending pre-determined electric stimuli to the vagus innervated auricular skin of the wearer's first ear to which the first stimulating electrode is in contact with.

25. The automatic detection-remedy system of claim 24, wherein the processing unit is further configured to analyze the EEG data recorded by the EEG monitoring system to detect presence or cessation of EEG signals suggestive of impending major depressive disorder, wherein when presence of EEG signals suggestive of impending major depressive disorder is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, and wherein when cessation of EEG signals suggestive of impending major depressive disorder is detected by the processing unit, the processing unit is configured to immediately send signals to the first taVNS unit to automatically stop sending pre-determined electric stimuli to the vagus innervated auricular skin of the wearer's first ear to which the first stimulating electrode is in contact with; and wherein the processing unit is further configured to analyze the EEG data recorded by the EEG monitoring system to detect presence or cessation of EEG signals suggestive of impending bipolar disorder, wherein when presence of EEG signals suggestive of impending bipolar disorder is detected by the processing unit, the processing unit is configured to immediately send signals to the first taVNS unit to automatically start sending pre-determined electric stimuli to the vagus innervated auricular skin of the wearer's first ear to which the first stimulating electrode is in contact with, and wherein when cessation of EEG signals suggestive of impending bipolar disorder is detected by the processing unit, the processing unit is configured to immediately send signals to the first taVNS unit to automatically stop sending pre-determined electric stimuli to the vagus innervated auricular skin of the wearer's first ear to which the first stimulating electrode is in contact with.

26. An auricular electroencephalogram (EEG) monitoring system, comprising:

a first EEG recording module, wherein the first EEG recording module includes a plurality of EEG sensor electrodes, wherein the first EEG recording module is in electronic communication with each EEG sensor electrode of the first EEG recording module, wherein the first EEG recording module is configured to record EEG data of the wearer, wherein all of the EEG sensor electrodes of the first EEG recording module are configured to be housed in a tubular-shaped structure, wherein the tubular-shaped structure is coupled with a first ear of a wearer, wherein all of the EEG sensor electrodes of the first EEG recording module are configured to be located on a surface of the tubular-shaped structure, wherein one or more EEG sensor electrode(s) are located at the upper surface of the tubular-shaped structure, wherein one or more EEG sensor electrode(s) are located 30-60 degrees above the horizontal level of the tubular-shaped structure and are facing forward-upward, wherein one or more EEG sensor electrode(s) are located 120-150 degrees above the horizontal level of the tubular-shaped structure and are facing backward-upward, wherein the tubular-shaped structure comprises an elastic flexible and adaptable material, and wherein the elastic flexible and adaptable material of the tubular shaped structure is configured to have appropriate elasticity flexibility and adaptability such that all of the EEG sensor electrodes of the first EEG recording module are naturally in close contact with the skin of the external ear canal of the wearer's first ear when the tubular-shaped structure is inserted into the external ear canal of the wearer's first ear;

a network interface, wherein the network interface is configured to generate a notification to at least one of: a client device of the wearer and a client device of the wearer's healthcare provider; and a processing unit in electronic communication with the first EEG recording module and the network interface, wherein the processing unit is configured to analyze the EEG data recorded by the first EEG recording module to detect presence or cessation of EEG signals suggestive of one or more neuropsychiatric disorders, wherein when the presence of EEG signals suggestive of the one or more neuropsychiatric disorders is detected by the processing unit, the processing unit is configured to immediately send signals to the network interface to generate a notification to at least one of: the client device of the wearer and the client device of the wearer's healthcare provider, and wherein when cessation of EEG signals suggestive of the one or more neuropsychiatric disorders is detected by the processing unit, the processing unit is further configured to immediately send signals to the network interface to generate a notification to at least one of: the client device of the wearer and the client device of the wearer's healthcare provider.

27. The Auricular EEG monitoring system of claim 26, wherein the processing unit is configured to analyze the EEG data recorded by the first EEG recording module to detect presence or cessation of EEG signals suggestive of seizure or impending seizure; wherein when presence of EEG signals suggestive of seizure is detected by the processing unit, the processing unit is configured to immediately send signals to the network interface to automatically send a notification to at least one of: a client device of the wearer and a client device of the wearer's healthcare provider; wherein when cessation of EEG signals suggestive of seizure is detected by the processing unit, the processing unit is configured to immediately send signals to the network interface to automatically send a notification to at least one of: the client device of the wearer and the client device of the wearer's healthcare provider, wherein when presence of EEG signals suggestive of impending seizure is detected by the processing unit, the processing unit is configured to immediately send signals to the network interface to automatically send a notification to at least one of: the client device of the wearer and the client device of the wearer's healthcare provider; wherein when cessation of EEG signals suggestive of impending seizure is detected by the processing unit, the processing unit is further configured to immediately send signals to the network interface to automatically send a notification to at least one of: the client device of the wearer and the client device of the wearer's healthcare provider;

wherein the processing unit is configured to analyze the EEG data recorded by the first EEG recording module to detect presence or cessation of EEG signals suggestive of migraine or impending migraine; wherein when presence of EEG signals suggestive of migraine is detected by the processing unit, the processing unit is configured to immediately send signals to the network interface to automatically send a notification to at least one of: a client device of the wearer and a client device of the wearer's healthcare provider; wherein when cessation of EEG signals suggestive of migraine is detected by the processing unit, the processing unit is configured to immediately send signals to the network interface to automatically send a notification to at least one of: the client device of the wearer and the client device of the wearer's healthcare provider, wherein when presence of EEG signals suggestive of impending migraine is detected by the processing unit, the processing unit is configured to immediately send signals to the network interface to automatically send a notification to at least one of: the client device of the wearer and the client device of the wearer's healthcare provider; wherein when cessation of EEG signals suggestive of impending migraine is detected by the processing unit, the processing unit is further configured to immediately send signals to the network interface to automatically send a notification to at least one of: the client device of the wearer and the client device of the wearer's healthcare provider;

wherein the processing unit is configured to analyze the EEG data recorded by the first EEG recording module to detect presence or cessation of EEG signals suggestive of cluster headache or impending cluster headache; wherein when presence of EEG signals suggestive of cluster headache is detected by the processing unit, the processing unit is configured to immediately send signals to the network interface to automatically send a notification to at least one of: a client device of the wearer and a client device of the wearer's healthcare provider; wherein when cessation of EEG signals suggestive of cluster headache is detected by the processing unit, the processing unit is configured to immediately send signals to the network interface to automatically send a notification to at least one of: the client device of the wearer and the client device of the wearer's healthcare provider, wherein when presence of EEG signals suggestive of impending cluster headache is detected by the processing unit, the processing unit is configured to immediately send signals to the network interface to automatically send a notification to at least one of: the client device of the wearer and the client device of the wearer's healthcare provider; wherein when cessation of EEG signals suggestive of impending cluster headache is detected by the processing unit, the processing unit is further configured to immediately send signals to the network interface to automatically send a notification to at least one of: the client device of the wearer and the client device of the wearer's healthcare provider;

wherein the processing unit is configured to analyze the EEG data recorded by the first EEG recording module to detect presence or cessation of EEG signals suggestive of major depressive disorder or impending major depressive disorder; wherein when presence of EEG signals suggestive of major depressive disorder is detected by the processing unit, the processing unit is configured to immediately send signals to the network interface to automatically send a notification to at least one of: a client device of the wearer and a client device of the wearer's healthcare provider; wherein when cessation of EEG signals suggestive of major depressive disorder is detected by the processing unit, the processing unit is configured to immediately send signals to the network interface to automatically send a notification to at least one of: the client device of the wearer and the client device of the wearer's healthcare provider, wherein when presence of EEG signals suggestive of impending major depressive disorder is detected by the processing unit, the processing unit is configured to immediately send signals to the network interface to automatically send a notification to at least one of: the client device of the wearer and the client device of the wearer's healthcare provider; wherein when cessation of EEG signals suggestive of impending major depressive disorder is detected by the processing unit, the processing unit is further configured to immediately send signals to the network interface to automatically send a notification to at least one of: the client device of the wearer and the client device of the wearer's healthcare provider; and wherein the processing unit is configured to analyze the EEG data recorded by the first EEG recording module to detect presence or cessation of EEG signals suggestive of bipolar disorder or impending bipolar disorder; wherein when presence of EEG signals suggestive of bipolar disorder is detected by the processing unit, the processing unit is configured to immediately send signals to the network interface to automatically send a notification to at least one of: a client device of the wearer and a client device of the wearer's healthcare provider; wherein when cessation of EEG signals suggestive of bipolar disorder is detected by the processing unit, the processing unit is configured to immediately send signals to the network interface to automatically send a notification to at least one of: the client device of the wearer and the client device of the wearer's healthcare provider, wherein when presence of EEG signals suggestive of impending bipolar disorder is detected by the processing unit, the processing unit is configured to immediately send signals to the network interface to automatically send a notification to at least one of: the client device of the wearer and the client device of the wearer's healthcare provider; wherein when cessation of EEG signals suggestive of impending bipolar disorder is detected by the processing unit, the processing unit is further configured to immediately send signals to the network interface to automatically send a notification to at least one of: the client device of the wearer and the client device of the wearer's healthcare provider.

28. The auricular EEG monitoring system of claim 26, further comprises a second EEG recording module, wherein the second EEG recording module includes a plurality of EEG sensor electrodes configured to contact separate areas of the wearer's skin selected from at least one of the following: external ear canal of a second ear of the wearer, external ear of the wearer's second ear, and a peri-auricular area around the wearer's second ear, wherein each EEG sensor electrode of the second EEG recording module is in electronic communication with the second EEG recording module, wherein the second EEG recording module is configured to record EEG data of the wearer, wherein the second EEG recording module is in electronic communication with the processing unit, and wherein the processing unit is configured to analyze the EEG data recorded by the first and the second EEG recording modules to detect presence or cessation of EEG signals suggestive of seizure, migraine, cluster headache, major depressive disorder and bipolar disorder.

29. The auricular EEG monitoring system of claim 26, wherein the processing unit is further configured to analyze the EEG data recorded by the first EEG recording module to detect presence or cessation of EEG signals suggestive of one or more impending neuropsychiatric disorders, wherein when the presence of EEG signals suggestive of the one or more impending neuropsychiatric disorders is detected by the processing unit, the processing unit is configured to immediately send signals to the network interface to generate a notification to at least one of: the client device of the wearer and the client device of the wearer's healthcare provider, and wherein when cessation of EEG signals suggestive of the one or more impending neuropsychiatric disorders is detected by the processing unit, the processing unit is further configured to immediately send signals to the network interface to generate a notification to at least one of: the client device of the wearer and the client device of the wearer's healthcare provider.

* * * * *